US012565526B2

(12) United States Patent
Hashemi et al.

(10) Patent No.: US 12,565,526 B2

(45) Date of Patent: Mar. 3, 2026

(54) FORMULATIONS OF ANTI-RSV ANTIBODIES AND METHODS OF USE THEREOF

(71) Applicant: Merck Sharp & Dohme LLC, Rahway, NJ (US)

(72) Inventors: Venus Hashemi, Manalapan, NJ (US); Arnab De, Burlington, MA (US); Chakravarthy Nachu Narasimhan, Scotch Plains, NJ (US)

(73) Assignee: Merck Sharpe & Dohme LLC, Rahway, NJ (US)

( * ) Notice: Subject to any disclaimer, the term of this patent is extended or adjusted under 35 U.S.C. 154(b) by 1068 days.

(21) Appl. No.: 17/285,156

(22) PCT Filed: Oct. 14, 2019

(86) PCT No.: PCT/US2019/056027

§ 371 (c)(1),
(2) Date: Apr. 14, 2021

(87) PCT Pub. No.: WO2020/081408

PCT Pub. Date: Apr. 23, 2020

(65) Prior Publication Data

US 2021/0324052 A1     Oct. 21, 2021

Related U.S. Application Data

(60) Provisional application No. 62/747,418, filed on Oct. 18, 2018.

(51) Int. Cl.
| | |
|---|---|
| *C07K 16/10* | (2006.01) |
| *A61K 47/12* | (2006.01) |
| *A61K 47/18* | (2017.01) |
| *A61K 39/00* | (2006.01) |

(52) U.S. Cl.
CPC .......... *C07K 16/1027* (2013.01); *A61K 47/12* (2013.01); *A61K 47/183* (2013.01); *A61K 2039/54* (2013.01); *A61K 2039/545* (2013.01); *C07K 2317/565* (2013.01); *C07K 2317/94* (2013.01)

(58) Field of Classification Search
CPC .......... C07K 16/1027; C07K 2317/565; C07K 2317/94; C07K 16/24; A61K 47/12; A61K 47/183; A61K 2039/54; A61K 2039/545; A61K 9/0019; A61K 39/39591; A61K 9/19; A61K 47/26; A61K 47/547; A61K 47/22; A61P 31/14
See application file for complete search history.

(56) References Cited

U.S. PATENT DOCUMENTS

| | | |
|---|---|---|
| 4,401,820 A | 8/1983 | Chibata et al. |
| 4,816,567 A | 3/1989 | Cabilly et al. |
| 5,262,296 A | 11/1993 | Ogawa et al. |
| 5,762,905 A | 6/1998 | Burton et al. |
| 6,171,586 B1 | 1/2001 | Lam et al. |
| 6,267,958 B1 | 7/2001 | Andya et al. |
| 6,329,511 B1 | 12/2001 | Vasquez et al. |
| 6,818,216 B2 | 11/2004 | Young et al. |
| 6,875,432 B2 | 4/2005 | Liu et al. |
| 7,247,707 B2 | 7/2007 | Besman et al. |
| 7,364,736 B2 | 4/2008 | Boyle et al. |
| 7,374,762 B2 | 5/2008 | Amphlett et al. |
| 7,375,193 B2 | 5/2008 | Baca et al. |
| 7,563,869 B2 | 7/2009 | Honjo et al. |
| 7,592,004 B2 | 9/2009 | Kaisheva et al. |
| 7,615,213 B2 | 11/2009 | Kasaian et al. |
| 7,635,473 B2 | 12/2009 | Warne et al. |
| 7,662,384 B2 | 2/2010 | Ramakrishnan et al. |
| 7,666,413 B2 | 2/2010 | Liu et al. |
| 7,691,379 B2 | 4/2010 | Allan et al. |
| 7,705,132 B2 | 4/2010 | Rehder et al. |
| 7,740,842 B2 | 6/2010 | Arvinte et al. |
| 7,833,525 B2 | 11/2010 | Shenoy et al. |
| 7,959,922 B2 | 6/2011 | Bakker et al. |
| 7,960,516 B2 | 6/2011 | Matheus et al. |
| 7,993,645 B2 | 8/2011 | Benson et al. |
| 7,998,477 B2 | 8/2011 | Yakovlevsky et al. |
| 8,034,906 B2 | 10/2011 | Borhani et al. |
| 8,067,547 B2 | 11/2011 | Ewert et al. |
| 8,142,776 B2 | 3/2012 | Liu et al. |
| 8,168,760 B2 | 5/2012 | Borhani et al. |
| 8,216,583 B2 | 7/2012 | Kruase et al. |
| 8,221,759 B2 | 7/2012 | Pilkington et al. |

(Continued)

FOREIGN PATENT DOCUMENTS

| | | |
|---|---|---|
| AU | 2010200784 A1 | 3/2010 |
| CA | 2918888 A1 | 1/2015 |

(Continued)

OTHER PUBLICATIONS

Kheddo et al. (International Journal of Pharmaceutics, 473: 126-133, 2014).*

Chauhan, Veeren M., Advancements in the co-formulation of biologic therapeutics, Journal of Controlled Release, 2020, pp. 397-405, vol. 327.

Davar, Diwakar et al., PD-1 Blockade in Advanced Melanoma in Patients with Hepatitis C and/or HIV, Case Reports in Oncological Medicine, 2015, 1-5, 2015: 737389.

Cleland, Jeffrey L. et al., A Specific Molar Ratio of Stabilizer to Protein is Required for Storage Stability of a Lyophilized Monoclonal Antibody, Journal of Pharmaceutical Sciences, 90(3), 310-321, 2001.

(Continued)

*Primary Examiner* — Nelson B Moseley, II

(74) *Attorney, Agent, or Firm* — Tamaria Dewdney; Andrew W. Custer

(57) ABSTRACT

The present invention relates to stable formulations comprising antibodies or antigen-binding fragments thereof that bind to respiratory syncytial virus (RSV). Also provided are methods of preventing and/or treating RSV-related diseases with the formulations of the invention.

17 Claims, 21 Drawing Sheets

Specification includes a Sequence Listing.

(56)  References Cited

U.S. PATENT DOCUMENTS

| | | | |
|---|---|---|---|
| 8,263,080 B2 | 9/2012 | Katsikis et al. | |
| 8,293,883 B2 | 10/2012 | Presta | |
| 8,568,720 B2 | 10/2013 | Morichika et al. | |
| 8,580,297 B2 | 11/2013 | Essler et al. | |
| 8,703,126 B2 | 4/2014 | Liu et al. | |
| 8,747,847 B2 | 6/2014 | Rotem-Yehudar et al. | |
| 8,933,075 B2 | 1/2015 | Wang et al. | |
| 9,220,776 B2 | 12/2015 | Sharma et al. | |
| 9,273,123 B2 | 3/2016 | Shenoy et al. | |
| 9,278,131 B2 | 3/2016 | Dauty et al. | |
| 9,592,297 B2 | 3/2017 | Xiang et al. | |
| 9,605,051 B2 | 3/2017 | Soane et al. | |
| 9,713,641 B2 | 7/2017 | Hicklin et al. | |
| 9,782,470 B2 | 10/2017 | Bhambhani et al. | |
| 9,926,371 B2 | 3/2018 | Liu et al. | |
| 9,963,500 B2 | 5/2018 | Vora et al. | |
| 10,072,072 B2 | 9/2018 | Vora et al. | |
| 10,188,730 B2 | 1/2019 | Liang | |
| 10,787,518 B2 | 9/2020 | Bernett et al. | |
| 2003/0138417 A1 | 7/2003 | Kaisheva et al. | |
| 2004/0091490 A1 | 5/2004 | Johnson et al. | |
| 2005/0101770 A1 | 5/2005 | Presta | |
| 2005/0175986 A1* | 8/2005 | Gross | C07K 16/1027 |
| | | | 435/339 |
| 2006/0029599 A1 | 2/2006 | Kaisheva et al. | |
| 2006/0057702 A1 | 3/2006 | Rosenthal et al. | |
| 2006/0088523 A1 | 4/2006 | Andya et al. | |
| 2006/0210557 A1 | 9/2006 | Luisi et al. | |
| 2006/0210567 A1 | 9/2006 | Collins et al. | |
| 2006/0246004 A1 | 11/2006 | Adams et al. | |
| 2006/0286103 A1 | 12/2006 | Kolhe et al. | |
| 2007/0009526 A1 | 1/2007 | Benson et al. | |
| 2007/0009541 A1 | 1/2007 | Amphlett et al. | |
| 2007/0048315 A1 | 3/2007 | Presta | |
| 2007/0053900 A1 | 3/2007 | Liu et al. | |
| 2007/0059803 A1 | 3/2007 | Oppmann et al. | |
| 2007/0065437 A1 | 3/2007 | Elson et al. | |
| 2007/0184050 A1 | 8/2007 | Ishikawa et al. | |
| 2007/0190047 A1 | 8/2007 | Brych et al. | |
| 2008/0003220 A1 | 1/2008 | Gokarn | |
| 2008/0050375 A1 | 2/2008 | Davies et al. | |
| 2008/0057070 A1 | 3/2008 | Long et al. | |
| 2008/0112953 A1 | 5/2008 | Mcauley et al. | |
| 2008/0124326 A1 | 5/2008 | Rehder et al. | |
| 2008/0152658 A1 | 6/2008 | Dagan et al. | |
| 2008/0213282 A1 | 9/2008 | Jacob | |
| 2008/0248048 A1 | 10/2008 | Fish et al. | |
| 2008/0254026 A1 | 10/2008 | Long et al. | |
| 2008/0286270 A1 | 11/2008 | Oliver et al. | |
| 2008/0311119 A1 | 12/2008 | Maloney et al. | |
| 2009/0042315 A1 | 2/2009 | Li et al. | |
| 2009/0060906 A1 | 3/2009 | Barry et al. | |
| 2009/0130119 A1 | 5/2009 | Abate et al. | |
| 2009/0162352 A1 | 6/2009 | Adler et al. | |
| 2009/0181027 A1 | 7/2009 | Dal Monte et al. | |
| 2009/0208492 A1 | 8/2009 | O'Connor et al. | |
| 2009/0217401 A1 | 8/2009 | Korman et al. | |
| 2009/0285802 A1 | 11/2009 | Igawa et al. | |
| 2009/0291076 A1 | 11/2009 | Morichika et al. | |
| 2009/0304706 A1 | 12/2009 | Lu et al. | |
| 2009/0311253 A1 | 12/2009 | Ghayur et al. | |
| 2010/0021461 A1 | 1/2010 | Burke et al. | |
| 2010/0137213 A1 | 6/2010 | Fernandez et al. | |
| 2010/0209434 A1 | 8/2010 | Bishop et al. | |
| 2010/0209437 A1 | 8/2010 | Elson et al. | |
| 2010/0266617 A1 | 10/2010 | Carven et al. | |
| 2010/0272731 A1 | 10/2010 | Presta et al. | |
| 2010/0278822 A1 | 11/2010 | Fraunhofer et al. | |
| 2010/0286038 A1 | 11/2010 | Antochshuk et al. | |
| 2010/0303827 A1 | 12/2010 | Sharma et al. | |
| 2010/0316638 A1 | 12/2010 | Gurny et al. | |
| 2011/0014203 A1 | 1/2011 | Nilsson et al. | |
| 2011/0059079 A1 | 3/2011 | Babuka et al. | |
| 2011/0060290 A1 | 3/2011 | Bonk et al. | |
| 2011/0086038 A1 | 4/2011 | Hope et al. | |
| 2011/0123550 A1 | 5/2011 | Shibayama et al. | |
| 2011/0171217 A1 | 7/2011 | Badkar et al. | |
| 2011/0226650 A1 | 9/2011 | Gokarn et al. | |
| 2011/0229490 A1 | 9/2011 | Li et al. | |
| 2011/0256135 A1 | 10/2011 | Fraunhofer et al. | |
| 2011/0300135 A1 | 12/2011 | Lobo et al. | |
| 2011/0318343 A1 | 12/2011 | Kaisheva et al. | |
| 2012/0039876 A1 | 2/2012 | Oliver et al. | |
| 2012/0076784 A1 | 3/2012 | Matheus et al. | |
| 2012/0128687 A1 | 5/2012 | Adler et al. | |
| 2012/0183531 A1 | 7/2012 | Lucas et al. | |
| 2012/0231972 A1 | 9/2012 | Golyshin et al. | |
| 2013/0022625 A1 | 1/2013 | Igawa et al. | |
| 2013/0058958 A1 | 3/2013 | Bowen et al. | |
| 2013/0108651 A1 | 5/2013 | Carven et al. | |
| 2013/0186797 A1 | 7/2013 | Walsh | |
| 2014/0044708 A1 | 2/2014 | Dauty et al. | |
| 2014/0044727 A1 | 2/2014 | Monck et al. | |
| 2014/0178401 A1 | 6/2014 | Nabozny et al. | |
| 2014/0206845 A1 | 7/2014 | Kameoka et al. | |
| 2014/0227250 A1 | 8/2014 | Li et al. | |
| 2014/0234296 A1 | 8/2014 | Sharma et al. | |
| 2014/0314714 A1 | 10/2014 | Honjo et al. | |
| 2014/0348841 A1 | 11/2014 | Schebye et al. | |
| 2015/0071936 A1 | 3/2015 | Mendiratta et al. | |
| 2015/0086537 A1 | 3/2015 | Adler et al. | |
| 2015/0086559 A1* | 3/2015 | Mueller | A61K 9/19 |
| | | | 424/139.1 |
| 2015/0100030 A1 | 4/2015 | Dix et al. | |
| 2015/0110783 A1 | 4/2015 | Lu et al. | |
| 2015/0258209 A1 | 9/2015 | Benz et al. | |
| 2015/0290325 A1 | 10/2015 | Kashi et al. | |
| 2015/0307606 A1 | 10/2015 | Basarkar et al. | |
| 2015/0359900 A1 | 12/2015 | Wang et al. | |
| 2016/0022814 A1 | 1/2016 | Petit et al. | |
| 2016/0045615 A1 | 2/2016 | Li et al. | |
| 2016/0090419 A1 | 3/2016 | Morichika et al. | |
| 2016/0166685 A1 | 6/2016 | Cheung et al. | |
| 2016/0176963 A1 | 6/2016 | Maurer et al. | |
| 2016/0222116 A1 | 8/2016 | Korman | |
| 2016/0355589 A1 | 12/2016 | Williams et al. | |
| 2017/0051039 A1 | 2/2017 | Gombotz et al. | |
| 2017/0056347 A1 | 3/2017 | Glick et al. | |
| 2017/0097333 A1 | 4/2017 | Bhagwat et al. | |
| 2017/0121394 A1* | 5/2017 | Vora | A61P 31/14 |
| 2017/0210792 A1 | 7/2017 | Mason et al. | |
| 2017/0210812 A1 | 7/2017 | Wong et al. | |
| 2017/0216433 A1 | 8/2017 | Li et al. | |
| 2017/0306025 A1 | 10/2017 | Du et al. | |
| 2017/0360929 A1 | 12/2017 | Sinha et al. | |
| 2018/0215808 A1* | 8/2018 | Vora | C07K 16/1027 |
| 2018/0237524 A1 | 8/2018 | Reichert et al. | |
| 2018/0251548 A1 | 9/2018 | Sabzevari et al. | |
| 2018/0333493 A1 | 11/2018 | Shenoy | |
| 2018/0339045 A1 | 11/2018 | Li et al. | |
| 2019/0330363 A1 | 10/2019 | Jansson et al. | |
| 2020/0055938 A1 | 2/2020 | Desai et al. | |
| 2020/0147213 A1 | 5/2020 | Sharma et al. | |
| 2020/0206350 A1 | 7/2020 | Chu et al. | |
| 2020/0262922 A1 | 8/2020 | Bhattacharya et al. | |
| 2021/0155913 A1 | 5/2021 | Park | |
| 2021/0317215 A1 | 10/2021 | Reichert et al. | |
| 2021/0363270 A1 | 11/2021 | Park | |
| 2022/0002410 A1 | 1/2022 | Antochshuk et al. | |
| 2022/0233693 A1 | 7/2022 | Huang et al. | |
| 2022/0378916 A1 | 12/2022 | Chu et al. | |
| 2025/0074985 A1 | 3/2025 | Bhattacharya et al. | |

FOREIGN PATENT DOCUMENTS

| CA | 2956000 A1 | 2/2016 |
|---|---|---|
| EP | 1324776 B1 | 4/2001 |
| EP | 1801123 A2 | 6/2007 |
| EP | 2116265 A2 | 11/2009 |
| EP | 2275119 B1 | 9/2013 |
| EP | 3117837 A1 | 6/2017 |
| EP | 3785701 A1 | 3/2021 |
| RU | 2560701 C2 | 8/2015 |
| RU | 2015123476 A | 10/2015 |

(56)                    References Cited

FOREIGN PATENT DOCUMENTS

| | | | |
|---|---|---|---|
| RU | 2589691 C2 | 7/2016 |
| WO | 1989011297 A1 | 11/1989 |
| WO | 199704801 A1 | 2/1997 |
| WO | 2000053631 A1 | 9/2000 |
| WO | 2001018051 A2 | 3/2001 |
| WO | 2001030393 A2 | 3/2001 |
| WO | 2002072636 A2 | 9/2002 |
| WO | 2002102303 A2 | 12/2002 |
| WO | 03009817 A2 | 2/2003 |
| WO | 2003009817 A1 | 2/2003 |
| WO | 2003039485 A2 | 5/2003 |
| WO | 2003086310 A2 | 10/2003 |
| WO | 2004007520 A2 | 1/2004 |
| WO | 2004055164 A2 | 7/2004 |
| WO | 2004056875 A1 | 7/2004 |
| WO | 2004071517 A2 | 8/2004 |
| WO | 2004081190 A2 | 9/2004 |
| WO | 2005120571 A2 | 12/2005 |
| WO | 2006121168 A1 | 11/2006 |
| WO | 2007019232 A2 | 2/2007 |
| WO | 2007024846 A2 | 3/2007 |
| WO | 2007092772 A2 | 8/2007 |
| WO | 2007110339 A1 | 10/2007 |
| WO | 2007147019 A2 | 12/2007 |
| WO | 2008076321 A1 | 6/2008 |
| WO | 2008079290 A2 | 7/2008 |
| WO | 2008086395 A2 | 7/2008 |
| WO | WO-2008079246 A2 * | 7/2008 | .............. A61P 1/04 |
| WO | 2008103473 A1 | 8/2008 |
| WO | 2008153610 A2 | 12/2008 |
| WO | 2008156712 A1 | 12/2008 |
| WO | 2008157409 A1 | 12/2008 |
| WO | 2009009407 A1 | 1/2009 |
| WO | 2009043933 A1 | 4/2009 |
| WO | 2009084659 A1 | 7/2009 |
| WO | 2009120684 A1 | 10/2009 |
| WO | 2009126688 A2 | 10/2009 |
| WO | 2010032220 A1 | 3/2010 |
| WO | 2010062372 A2 | 6/2010 |
| WO | 2010069858 A1 | 6/2010 |
| WO | 2010102241 A1 | 9/2010 |
| WO | 2010129469 A1 | 11/2010 |
| WO | 2011012637 A1 | 2/2011 |
| WO | 2011012637 A2 | 2/2011 |
| WO | 2011017070 A1 | 2/2011 |
| WO | 2011024862 A1 | 3/2011 |
| WO | 2011029892 A2 | 3/2011 |
| WO | 2011056772 A1 | 5/2011 |
| WO | 2011080209 A2 | 7/2011 |
| WO | 2011089062 A2 | 7/2011 |
| WO | 2011139718 A1 | 11/2011 |
| WO | 2012018538 A2 | 2/2012 |
| WO | 2012135035 A1 | 10/2012 |
| WO | 2012165917 A1 | 12/2012 |
| WO | 2013063468 A1 | 5/2013 |
| WO | 2013167720 A1 | 11/2013 |
| WO | 2014004436 A2 | 1/2014 |
| WO | 2014036071 A1 | 3/2014 |
| WO | 2014036076 A1 | 3/2014 |
| WO | 2015011199 A1 | 1/2015 |
| WO | 2015038777 A1 | 3/2015 |
| WO | 2015038782 A1 | 3/2015 |
| WO | 2015038811 A2 | 3/2015 |
| WO | 2015038818 A2 | 3/2015 |
| WO | 2015048520 A1 | 4/2015 |
| WO | 2015143343 A2 | 9/2015 |
| WO | 2016024228 A1 | 2/2016 |
| WO | 2016028672 A1 | 2/2016 |
| WO | 2016070051 A2 | 5/2016 |
| WO | 2016100882 A1 | 6/2016 |
| WO | 2016118654 A1 | 7/2016 |
| WO | 2016140717 A1 | 9/2016 |
| WO | 2016168716 A1 | 10/2016 |
| WO | 2016176504 A1 | 11/2016 |
| WO | 2016200782 A1 | 12/2016 |
| WO | 2017021526 A1 | 2/2017 |
| WO | 2017030823 A2 | 2/2017 |
| WO | 2017040864 A1 | 3/2017 |
| WO | 2017048824 A1 | 3/2017 |
| WO | 2017053748 A2 | 3/2017 |
| WO | 2017054646 A1 | 4/2017 |
| WO | 2017079150 A1 | 5/2017 |
| WO | 2017089895 A1 | 6/2017 |
| WO | 2017112621 A1 | 6/2017 |
| WO | 2017131496 A1 | 8/2017 |
| WO | 2017198741 A1 | 11/2017 |
| WO | 2018091729 A2 | 5/2018 |
| WO | 2018158332 A1 | 9/2018 |
| WO | 2018160722 A1 | 9/2018 |
| WO | 2018183928 A1 | 10/2018 |
| WO | 2018187057 A1 | 10/2018 |
| WO | 2018204343 A1 | 11/2018 |
| WO | 2018204368 A1 | 11/2018 |
| WO | 2018204374 A1 | 11/2018 |
| WO | 2018204405 A1 | 11/2018 |
| WO | 2018222722 A2 | 12/2018 |
| WO | 2020028011 A1 | 2/2020 |
| WO | 2020197230 A1 | 10/2020 |
| WO | 2021118930 A2 | 6/2021 |

OTHER PUBLICATIONS

Krishnan, Development of Formulations for Therapeutic Monoclonal Antibodies and Fc Fusion Proteins, Chugai Exhibit 2014, 2010, pp. 1-48.
Pertsev, I.M. et al., Pharmaceutical and Biomedical Aspects of Drugs, Kharkov Publishing House UkrFA, 1999, 253-254, Chapter 11.
Bittner, Beate et al., Subcutaneous Administration of Biotherapeutics: An Overview of Current Challenges and Opportunities, BioDrugs, 32, 425-440, 2018.
Request for entry into the European phase dated Jun. 9, 2022 for PCTUS2021051641, 22 pages.
Shpilberg, O. et al., Subcutaneous administration of rituximab (MabThera) and trastuzumab (Herceptin) using hyaluronidase, British Journal of Cancer, 109, 1556-1561, 2013.
Kang, Jichao et al., Rapid formulation development for monoclonal antibodies, Bio Process International, 2016, 40-45, 14(4).
Gervasi, V., et al., Parenteral protein formulations: An overview of approved products within the European Union, European Journal of Pharmaceutics and Biopharmaceutics, vol. 131, p. 8-24, 2018.
Li, Z., et al., Coadsorption of a Monoclonal Antibody and Nonionic Surfactant at the SiO2/Water Interface, ACS Applied Materials & Interfaces, vol. 10, No. 51, p. 44257-44266, Dec. 26, 2018.
Wade, A., et al., Antioxidant characteristics of L-histidine, Journal of Nutritional Biochemistry, vol. 9, No. 6, p. 308-315, 1998.
Abrahams, Gabriel Jan et al., BLAST ing away preconceptions in crystallization trials, Acta Crystallographica Section F Structural Biology Communications, 2019, 184-192, 75(3,4).
Ahamed, Tangir, Phase Behavior of an Intact Monoclonal Antibody, Biochemical Journal, 2007, 610-619, 93.
Altschul, Stephen F., A Protein Alignment Scoring System Sensitive at All Evolutionary Distances, J Mol Evol, 1993, 290-300, 36.
Armstrong, NA, Sucrose, Handbook of Pharmaceutical Excipients, 2009, 703-707, 6th Edition.
Banks et al., Removal of cysteinylation from an unpaired sulfhydryl in the variable region of a recombinant monoclonal IgG1 antibody improves homogeneity, stability, and biological activity, J Pharm Sci, 2008, 775-790, 97(2).
Banks, Douglas D. et al., The Effect of Sucrose Hydrolysis on the Stability of Protein Therapeutics during Accelerated Formulation Studies, J. Pharm. Sci., 2009, 4501-4510, 98(12).
Basu et al., Protein crystals for the delivery of biopharmaceuticals, Expert Opinion on Biological Therapy, 2004, pp. 301-317, vol. 4(3).
Bernstein, J., Bioavailability, Polymorphism of molecular crystals, 2007, 324-330 (translated pp. 1-9), Ch. 7.3.2.
Bernstein, J., Bioavailability, Polymorphism of molecular crystals, 2007, 324-330, Ch. 7.3.2.

(56) References Cited

OTHER PUBLICATIONS

Bhambhani, Akhilesh, Formulation Design and High-Throughput Excipient Selection Based on Structural Integrity and Conformational Stability of Dilute and Highly Concentrated IgG1 Monoclonal Antibody Solutions, Journal of Pharmaceutical Sciences, 2012, 1120-1135, vol. 101, No. 3.

Borwankar, A.U. et al., Viscosity Reduction of a Concentrated Monoclonal Antibody with Arginine·HCI and Arginine·Glutamate, Ind. Eng. Chem. Res., 2016, 11225-11234, 55(43).

Bowman, Edward P. et al., Rationale and safety of anti-interleukin-23 and anti-interleukin-17A therapy, Curr Opin Infect Dis, 2006, 245-252, 19(3).

Carpenter, John F. et al., Rational Design of Stable Lyophilized Protein Formulations: Some Practical Advice, Pharmaceutical Research, 1997, 969-975, 14(8).

Carpenter, John F., Application of infrared spectroscopy to development of stable lyophilized protein formations, European Journal of Pharmaceutics and Biopharmaceutics, 1998, 231-238, 45.

Chang, B.S. and Hershenson, S., Practical approaches to protein formulation development in "Rationale Design of stable protein formulations—theory and practice", Kluwer Academic/Plenum Publishers, 2002, 1-25.

Chauvin et al., TIGIT and PD-1 impair tumor antigen-specific CD8 T cells in melanoma patients, Journal of Clinical Investigation, 2015, pp. 2046-2058, vol. 125(5).

Chen, et al., Influence of histidine on the stability and physical properties of a fully human antibody in aqueous and solid forms, 2003, 1952-1960, 20(12), Pharm Res.

Cordoba et al., Non-enzymatic hinge region fragmentation of antibodies in solution, 2005, 115-121, 818(2), J Chromatogr B Analyt Technol Biomed Life Sci.

Costantino, Henry R., The Secondary Structure and Aggregation of Lyophilized Tetanus Toxoid, Journal of Pharmaceutical Sciences, 1996, 1290-1293, vol. 85, No. 12.

Cua, Daniel J. et al., TGF-beta, a 'double agent' in the immune pathology war, Nat. Immunol., 2006, 557-559, 7(6).

Cudney, R., Protein Crystallization and Dumb Luck, The Rigaku Journal, 1999, 1-7, vol. 16, No. 1.

Database CAPLUS [Online] Chemical Abstracts; Jan. 1, 1976 (Jan. 1, 1976), Pfeilsticker Konrad et al: "Studies on the behavior of ethylene oxide in food fumigation, part IX.", XP055786686, retrieved from STN Database accession No. 1976:163013 CAPLUS * N-[2-(2-hydroxyethoxy)ethyl]-L-Tyrosine RN 58970-48-2 * (1 Page).

Daugherty et al., Formulation and delivery issues for monoclonal antibody therapeutics, Advanced Drug Delivery Reviews, 2006, pp. 686-706, vol. 58, No. 5-6.

Daugherty, Ann L. et al., Formulation and Delivery Issues for Monoclonal Antibody Therapeutics, Current Trends in Monoclonal Antibody Development and Manufacturing, 2010, 103-129, Chapter 8.

Davagnino, Juan et al., Acid hydrolysis of monoclonal antibodies, J. Immunol. Methods, 1995, 177-180, 185(2).

Davies et al., Structural Determinants of Unique Properties of Human IgG4-Fc, Journal of Molecular Biology, 2014, pp. 630-644, vol. 426(3).

Dayhoff, M.O., A Model of Evolutionary Change in Proteins, Atlas of Protein Sequence and Structure, 1978, 345-352, 22.

Dear et al., Contrasting the Influence of Cationic Amino Acids on the Viscosity and Stability of a Highly Concentrated Monoclonal Antibody, Pharm. Res., 2017, 193-207, vol. 34.

Dembo, Amir, Limit Distribution of Maximal Non-Aligned Two-Sequence Segmental Score, The Annals of Probability, 1994, 2022-2039, vol. 22, No. 4.

Dougall, W.C. et al., TIGIT and CD96: new checkpoint receptor targets for cancer immunotherapy, Immunological Reviews, 2017, 112-120, 276.

European Medicines Agency, European Public Assessment Report (EPAR) Avastin, Scientific Discussion. Jan. 24, 2006, pp. 1-61.

European Search Report, application No. 12763896.03, mailed Nov. 5, 2014, 6 pages.

Falconer, Robert J. et al., Stabilization of a monoclonal antibody during purification and formulation by addition of basic amino acid excipients, J Chem Technol Biorechnol, 2011, 942-948, 86.

FDA label for Amjevita (Adalimumab), Sep. 2016, p. 1-61.

FDA label for Arzerra (Ofatumumab), Oct. 2009, p. 1-13.

FDA label for Avastin (Bevacizumab), Sep. 2011, p. 1-25.

FDA label for Bavencio (Avelumab), Mar. 2017, p. 1-20.

FDA label for Campath or Lemtrada (Alemtuzumab), Sep. 2014, p. 1-18.

FDA label for Cimzia (Certolizumab), Jan. 2017, p. 1-40.

FDA label for Drazalex (Daratumumab), Nov. 2016, p. 1-26.

FDA label for Humira (Adalimumab), Jan. 2008, p. 1-34.

FDA label for Kadcyla (Ado-Trastuzumab Emtansine), Aug. 29, 2013, p. 1-26.

FDA label for Mylotarg (Gemtuzumab Ozogamicin), Aug. 2005, p. 1-21.

FDA label for Opdivo (Nivolumab), Dec. 2017, p. 1-73.

FDA label for Praxbind (Idarucizumab), Oct. 2015, p. 1-10.

FDA label for Prolia (Denosumab), Sep. 2011, p. 1-20.

FDA label for Prostascint (Capromab Pendetide), Jun. 2012, p. 1-16.

FDA label for Protrazza (Necitumumab), Nov. 2015, p. '1-12.

FDA label for Raxibacumab, Dec. 2012, p. 1-14.

FDA label for Reopro (Abciximab), dated Nov. 4, 1997, p. 1-17.

FDA label for Repatha (Evolocumab), Aug. 2015, p. 1-34.

FDA label for Rituxan (Rituximab), Feb. 2010, p. 1-35.

FDA label for Simulect (Basiliximab), May 1998, p. 1-7.

FDA label for Soliris (Eculizumab), Sep. 2011, p. 1-24.

FDA label for Tysabri (Natalizumab), Jan. 2012, p. 1-32.

FDA label for Vectibix (Panitumumab), Jun. 2017, p. 1-31.

FDA label for Zevalin (Ibritumomab Tiuxetan), Sep. 2009, p. 1-11.

FDA label of Adcetris, Nov. 2014, pp. 1-19.

FDA label of Benlysta, Mar. 2012, pp. 1-22.

FDA label of Blincyto, Dec. 2014, pp. 1-24.

FDA label of Cinqair, Mar. 2016, pp. 1-16.

FDA label of Empliciti, Nov. 2015, pp. 1-22.

FDA label of Entyvio, May 2014, pp. 1-21.

FDA label of Erbitux, Jan. 2012, pp. 1-31.

FDA label of Fasenra, Nov. 2017, pp. 1-8.

FDA label of Ilaris, Mar. 2012, pp. 1-13.

FDA label of Kevzara, May 2017, pp. 1-45.

FDA label of Nucala, Nov. 2015, pp. 1-28.

FDA label of Ocrevus, Mar. 2017, pp. 1-18.

FDA label of Raptiva, Mar. 2009, pp. 1-36.

FDA label of Remicade, Feb. 2011, pp. 1-47.

FDA label of Siliq, Feb. 2017, pp. 1-22.

FDA label of Sylvant, 2014, pp. 1-16.

FDA label of Taltz Mar. 2016, pp. 1-25.

FDA label of Xolair, 2007, pp. 1-20.

FDA label of Zinbryta, May 2016, pp. 1-32.

FDA label of Zinplava, Oct. 2016, pp. 1-11.

Fukuda, Masakazu et al., Thermodynamic and Fluorescence Analyses to Determine Mechanisms of IgG1 Stabilization and Destabilization by Arginine, Pharm. Res., 2014, 992-1001, 31.

Garber, Ellen et al., A broad range of Fab stabilities within a host of therapeutic IgGs, Biochemical and Biophysical Research Communications, 2007, 751-757, 355.

Ghosh et al., Natalizumab for active Crohns disease, New England J. Med., 2003, pp. 24-32, 348.

Giege, et al., Crystallogenesis of Biological Macromolecules: Facts and Perspectives, Acta Cryst., 1994, pp. 339-350, D50.

Gikanga, Benson et al., Manufacturing of High-Concentration Monoclonal Antibody Formulations via Spray Drying—the Road to Manufacturing Scale, PDS J Pharm Sci and Tech, 2015, 59-73, 69.

Gish, Warren, Identification of protein coding regions by database similarity search, Nature Genetics, 1993, 266-272, 3.

Gizzi, Patrick et al., Molecular Tailored Histidine-Based Complexing Surfactants: From Micelles to Hydrogels, Eur. J. Org. Chem., 2009, 3953-3963, N/A.

Guo, Zheng et al., Structure-Activity Relationship for Hydrophobic Salts as Viscosity-Lowering Excipients for Concentrated Solutions of Monoclonal Antibodies, Pharm Res, 2012, 3102-3109, 29.

(56)          References Cited

OTHER PUBLICATIONS

Harris et al., Comparison of the conformations of two intact monoclonal antibodies with hinges, Immunological Reviews, 1998, pp. 35-43, vol. 163.

Harris et al., Crystallization of Intact Monoclonal Antibodies, Proteins: Structure, Function, and Genetics, 1995, pp. 285-289, vol. 23, No. 2.

Harris, Reed J. et al., Identification of multiple sources of charge heterogeneity in a recombinant antibody, Journal of Chromatography B, 2001, 233-245, 752(2).

He et al., Humanization and Pharmacokinetics of a Monoclonal Antibody with Specificity for both E- and P-Selectin, J. Immunol., 1998, pp. 1029-1035, 160.

Hermans, J. et al., Physicochemical Parameters Affecting the Electrospray Ionization Efficiency of Amino Acids after Acylation, Analytical Chemistry, 2017, 9159-9166, 89(17).

Herold, Anti-CD3 Monoclonal Antibody in New-Onset Type 1 Diabetes Mellitus, New England Journal of Medicine, 2002, pp. 1692-1698, 346.

International Search Report of the International Searching Authority for International Application No. PCT/US2013/073825, mailed Feb. 7, 2014 (3 pages).

Introduction to the textbook which contains D16, Nicholas W. Warne, 2010.

Ionescu, Roxana et al., Kinetics of Chemical Degradation in Monoclonal Antibodies: Relationship between Rates at the Molecular and Peptide Levels, Anal. Chem., 2010, 3198-3206, 82(8).

Izutsu, Ken-Ichi et al., Excipient crystallinity and its protein-structure—stabilizing effect during freeze-drying, Journal of Pharmacy and Pharmacology, 2002, 1033-1039, 54.

Jezek, Jan et al., Viscosity of concentrated therapeutic protein compositions, Advanced Drug Delivery Reviews, 2011, 1107-1117, 63.

Jones, Andrew J.S., Analysis of Polypeptides and proteins, Advanced Drug Delivery Reviews, 1993, 29-90, 10.

Kaithamana, Shashi, Induction of Experimental Autoimmune Graves' Disease in BALB/c Mice, The Journal of Immunology, 1999, 5157-5164, 163.

Keytruda (Merck & Co., Inc., Whitehouse Station, NJ USA; initial U.S. approval 2014, updated Sep. 2017) 49 pages.

Kheddo, Priscilla et al., The effect of arginine glutamate on the stability of monoclonal antibodies in solution, Int. J. Pharmaceutics, 2014, 126-133, 473.

Kohler et al., Continuous Cultures of Fused Cells Secreting Antibody of Predefined Specificity, Nature, 1975, pp. 495-497, vol. 256.

Kundrot, C.E., Which strategy for a protein crystallization project?, Cellular Molecular Life Science, 2004, 525-536, 61.

Lam, Xanthe M. et al., Antioxidants for Prevention of Methionine Oxidation in Recombinant Monoclonal Antibody HER2, J. Pharm. Sci., 1997, 1250-1255, 86(11).

Langowski, John L. et al., IL-23 promotes tumour incidence and growth, Nature, 2006, 461-465, 442(7101).

Langrish, Claire L. et al., IL-12 and IL-23: master regulators of innate and adaptive immunity, Immunol. Rev., 2004, 96-105, 202.

Le Doussal et al., Enhanced in vivo targeting of an asymmetric bivalent hapten to double-antigen-positive mouse B cells with monoclonal antibody conjugate cocktails, J. Immunol., 1991, pp. 169-175, 146.

Liu, Dingjiang et al., Structure and Stability Changes of Human IgG1 Fc as a Consequence of Methionine Oxidation, Biochemistry, 2008, 5088-5100, 47(18).

Liu, Hongcheng et al., Heterogeneity of Monoclonal Antibodies, J. Pharm. Sci., 2008, 2426-2447, 97(7).

Liu, Jun et al., Reversible Self-Association Increases the Viscosity of a Concentrated Monoclonal Antibody in Aqueous Solution, Journal of Pharmaceutical Sciences, 2005, 1928-1940, 94(9).

Mach, Henryk et al., Addressing new analytical challenges in protein formulation development, European Journal of Pharmaceutics and Biopharmaceutics, 2011, 196-207, 78.

Manzini, B. et al., Polymer-supported syntheses of oxo-crown ethers and derivatives containing a-amino-acid residues, Reactive & Functional Polymers, 2008, 1297-1306, 68(9).

McCoy et al., Phaser crystallographic software, Journal of Applied Crystallography, 2007, pp. 658-674, vol. 40.

McDermott, et al., PD-1 as a potential target in cancer therapy, Cancer Medicine, 2013, pp. 662-673, WO.

Menne, Kerstin M.L., A comparison of signal sequence prediction methods using a test set of signal peptides, Bioinformatics Applications Note, 2000, 741-742, 16.

Milgrom et al., Treatment of allergic asthma with monoclonal anti IgE antibody, New England Journal Med., 1999, pp. 1966-1973, 341.

Morissette, Sherry L. et al., High-throughput crystallization: polymorphs, salts, co-crystals and solvates of pharmaceutical solids, Advanced Drug Delivery Reviews, 2004, 275-300, 56.

Murakami, Monica S., Cell Cycle Regulation, Oncogenes, and Antineoplastic Drugs, The Molecular Basis of Cancer, 1995, 3-17, Chapter 1.

Ollmann Saphire et al., Crystal Structure of a Neutralizing Human IgG Against HIV-1: A Template for Vaccine Design, Science, 2001, pp. 1155-1159, vol. 293.

Pearlman, Rodney, Analysis of Protein Drugs, Peptide and Protein Drug Delivery, 1991, 247-301, Chapter 6.

Perchiacca, Joseph M. et al., Aggregation-resistant domain antibodies engineered with charged mutations near the edges of the complementarity-determining regions, Protein Engineering, Design & Selection, 2012, 591-601, 25(10).

Poole, Raewyn M., Pembrolizumab: First Global Approval, Drugs, 2014, 1973-1981, 74(16).

Portielje, IL-12: a promising adjuvant for cancer vaccination, Cancer Immunol Immunother, 2003, 133-144, 52.

Presta, Leonard G. et al., Selection, design, and engineering of therapeutic antibodies, J. Allergy Clin. Immunol., 2005, 731-736, 116(4).

Presta, Leonard G., Engineering of therapeutic antibodies to minimize immunogenicity and optimize function, Advanced Drug Delivery Reviews, 2006, 640-656, 58.

Prestrelski, Steven J., Optimization of Lyophilization Conditions for Recombinant Human Interleukin-2 by Dried State Conformational Analysis Using Fourier-Transform Infrared Spectroscopy, Pharmaceutical Research, 1995, 1250-1259, vol. 12, No. 9.

Prolia prescribing information, Jun. 2010.

Qing, G. et al., Chiral Effect at Protein/Graphene Interface: A Bioinspired Perspective To Understand Amyloid Formation, Journal of the American Chemical Society, 2014, 10736-10742, 136(30).

Reich, Gabriele. Chapter 10: "Pharmaceutical Formulation and Clinical Application". D19 is a chapter from the textbook "Handbook of Therapeutic Antibodies, vol. 1", published by Wiley & Sons in 2007.

Reichert, et al., Monoclonal antibody successes in the clinic, Nature Biotechnology, 2005, pp. 1073-1078, vol. 23.

Reissner, K. J. et al., Deamidation and isoaspartate formation in proteins: unwanted alterations or surreptitious signals?, Cell. Mol. Life Sci., 2003, 1281-1295, 60.

Remmele, Richard L., Interleukin-1 Receptor (IL-1R) Liquid Formulation Development Using Differential Scanning Calorimetry, Pharmaceutical Research, 1998, 200-208, vol. 15, No. 2.

Rustandi, Richard R. et al., Applications of CE SDS gel in development of biopharmaceutical-antibody-based products, Electrophoresis, 2008, 3612-3620, 29(17).

Sane, Samir U. et al., Raman Spectroscopic Characterization of Drying-Induced Structural Changes in a Therapeutic Antibody: Correlating Structural Changes with Long-Term Stability, Journal of Pharmaceutical Sciences, 2004, 1005-1018, 93(4).

Scapin et al., Structure of full-length human anti-PD1 therapeutic IgG4 antibody pembrolizumab, Nature Structural & Molecular Biology, 2015, pp. 953-958, vol. 22, No. 12.

Seifert, Tina et al., Chroman-4-one- and Chromone-Based Sirtuin 2 Inhibitors with Antiproliferative Properties in Cancer Cells, Journal of Medicinal Chemistry, 2014, 9870-9888, 57.

Shahrokh, Zahra, Approaches to Analysis of Aggregates and Demonstrating Mass Balance in Pharmaceutical Protein (Basic Fibro-

(56) References Cited

OTHER PUBLICATIONS blast Growth Factor) Formulations, Journal of Pharmaceutical Sciences, 1994, 1645-1650, vol. 83, No. 12.

Sharma et al., Preparation, purification and crystallization of antibody Fabs and single-chain Fv domains, Immunology Methods Manual: The Comprehensive Sourcebook of Techniques, 1997, pp. 15-37, vol. 1.

Shire, Steven J. et al., Formulation and manufacturing of biologics, Current Opinion in Biotechnology, 2009, 708-714, 20.

Shire, Steven J., et al., Challenges in the Development of High Protein Concentration Formulations, Journal of Pharmaceutical Sciences, 2004, 1390-1402, 93(6).

Sigma-Aldrich, Co., Products for Life Science Research, 2001, 1-47, N/A.

Slamon et al., Use of chemotherapy plus a monoclonal antibody against HER2 for metastatic breast cancer that overexpresses HER2, New England J. Med., 2001, pp. 783-792, 344.

Sluzky, Victoria, Chomatographic Methods for Quantitative Analysis of Native, Denatured, and Aggregated Basic Fibroblast Growth Factor in Solution Formulations, Pharmaceutical Research, 1994, 485-490, vol. 11, No. 4.

Study NCT01295827 posted in Feb. 2011 on ClinicalTrials.gov (see p. 6 "First Posted"), 14 pages.

Sumit Goswami, Developments and Challenges for mAb-based Therapeutics, Antibodies, 2013, 452-500, 2.

Sworn statement of Chakravarthy Nachu Narasimhan, 2 pages.

Te Booy, Marcel, Evaluation of the Physical Stability of Freeze-Dried Sucrose-Containing Formulations by Differential Scanning Calorimetry, Pharmaceutical Research, 1992, 109-114, vol. 9, No. 1.

Tomar, Dheeraj S., Molecular basis of high viscosity in concentrated antibody solutions: Strategies for high concentration drug product development, mAbs, 2016, 216-228, vol. 8, No. 2.

Topalian et al., Survival, Durable Tumor Remission, and Long-Term Safety in Patients With Advanced Melanoma Receiving Nivolumab, Clinical Journal of Oncology, 2014, pp. 1020-1030, vol. 32, No. 10.

Tysabri prescribing information, Nov. 2004.

Uchiyama, Susumu, Liquid formulation for antibody drugs, Biochimica et Biophysica Acta, 2014, 2041-2052, 1844.

Usami, A., The effect of pH, hydrogen peroxide and temperature on the stability of human monoclonal antibody, Journal of Pharmaceutical and Biomedical Analysis, 1996, 1133-1140, 14.

Vermeer, Arnoldus W. P. et al., The Thermal Stability of Immunoglobulin: Unfolding and Aggregation of a Multi-Domain Protein, Biophysical Journal, 2000, 394-404, 78(1).

Vlasak, Josef et al., Fragmentation of monoclonal antibodies, MABS, 2011, 253-263, 3(3).

Vlasak, Josef et al., Identification and characterization of asparagine deamidation in the light chain CDR1 of a humanized IgG1 antibody, Anal. Biochem., 2009, 145-154, 392(2).

Von Heijne et al., A new method for predkting signal sequence cleavage sites, Nucleic Acids Res., 1986, pp. 4683-4690, 14.

Walily, EL, Simultaneous determination of tenoxicam and 2-aminopyridine using derivative spectrophotometry and high-performance liquid chromatography, Journal of Pharmaceutical and Biomedical Analysis, 1997, 1923-1928, 15.

Wang, B. et al., Amino acid endcapped poly(p-dioxanone): synthesis and crystallization, J Polym Res, 2013, 1-9, 20(4).

Wang, Shujing et al., Viscosity-Lowering Effect of Amino Acids and Salts on Highly Concentrated Solutions of Two IgG1 Monoclonal Antibodies, Mol. Pharmaceutics, 2015, 4478-4487, 12.

Warne, Development of high concentration protein biopharmaceuticals: the use of platform approaches in formulation development, 2011, 208-212, 78(2), Eur J Pharm Biopharm.

Warne, Nicholas W., Formulation Development of Phase 1-2 Biopharmaceuticals: An Efficient and Timely Approach, John Wiley & Sons, Inc., 2010, 147-159, Chapter 6.

Weber, Patricia C., Overview of Protein Crystallization Methods, Methods in Enzymology, 1997, 13-22, 276.

Webster, Simon, Predicting Long-Term Storage Stability of Therapeutic Proteins, Pharmaceutical Technology, 2013, 1-7, 37(11).

Wei, Ziping et al., Identification of a Single Tryptophan Residue as Critical for Binding Activity in a Humanized Monoclonal Antibody against Respiratory Syncytial Virus, Anal. Chem., 2007, 2797-2805, 79(7).

Wiekowski, Maria T. et al., Ubiquitous Transgenic Expression of the IL-23 Subunit p19 Induces Multiorgan Inflammation, Runting, Infertility, and Premature Death, J. Immunol., 2001, 7563-7570, 166(12).

Written Opinion, International Application No. PCT/US12/31063, date of mailing Jun. 22, 2012.

Yang, M. et al., Crystalline monoclonal antibodies for subcutaneous delivery, Proceedings of the the National Academy of Sciences, Jun. 10, 2003, 6934-6939, 100-12.

Yu, Lei et al., Investigation of N-terminal glutamate cyclization of recombinant monoclonal antibody in formulation development, J. Pharm Biomed. Anal., 2006, 455-463, 42(4).

Zang, Yuguo, Towards Protein Crystallization as a Process Step in Downstream Processing of Therapeutic Antibodies: Screening and Optimization at Microbatch Scale, PLoS One, 2011, 1-8, 6(9).

Zhang, J. et al., Synthesis and characterization of heterotelechelic poly(ethylene glycol)s with amino acid at one end and hydroxyl group at another end, Journal of Applied Polymer Science, 2008, 2432-2439, 110(4).

Zhou, Shuxia et al., Biotherapeutic Formulation Factors Affecting Metal Leachables from Stainless Steel Studied by Design of Experiments, AAPS PharmSciTech, 2012, 284-294, 13(1).

Sikalidis, Angelos K., Amino Acids and Immune Response: A Role for Cysteine, Glutamine, Phenylalanine, Tryptophan and Arginine in T-cell Function and Cancer?, Pathol. Oncol. Res, 2015, 9-17, 21.

Tyagi, R. et al., The use of chemical modification and chemical crosslinking to stabilize proteins (enzymes), Biochemistry, 1998, 395-407, 63(3).

Yakubke, H.D. et al., Amino acids, peptides, proteins, M: Mir, 1985, 456, N/A.

FDA insert for Keytruda (pembrolizumab). May 2017. (Year: 2017) 46 pages.

Telipepalli, Srivalli N. et al., Structural Characterization of IgG1 mAb Aggregates and Particles Generated Under Various Stress Conditions, J Pharm Sci, 103(3), 796-809, 2014.

Morar-Mitrica, Sorina et al., Development of a stable low-dose aglycosylated antibody formulation to minimize protein loss during intravenous administration, mAbs, 7:4, 792-803, 2015.

Chang, Byeong et al., Physical Instability in Peptide and Protein Pharmaceuticals, Formulation and Process Development Strategies for Manufacturing Biopharmaceuticals, 2010, 69-104, Chapter 3.

Grillo, Adeolla O., Late Stage Formulation Development and Characterization of Biopharmaceuticals, Formulation and Process Development Strategies for Manufacturing Biopharmaceuticals, 2010, 161-171, Chapter 7.

Joshi, Sangeeta B. et al., An Empirical Phase Diagram/ High Throughput Screening Approach to the Characterization and Formulation of Biopharmaceuticals, Formulation and Process Development Strategies for Manufacturing Biopharmaceuticals, 2010, 173-205, Chapter 8.

Krishnan, Sampathkumar et al., Development of Formulations for Therapeutic Monoclonal Antibodies and Fc Fusion Proteins, Formulation and Process Development Strategies for Manufacturing Biopharmaceuticals, 2010, 383-427, Chapter 16.

Manning, Mark Cornell et al., Prediction of Protein Aggregation Propensities from Primary Sequence Information, Formulation and Process Development Strategies for Manufacturing Biopharmaceuticals, 2010, 329-347, Chapter 14.

Nayar, Rajiv et al., Efficient Approaches to Formulation Development of Biopharmaceuticals, Formulation and Process Development Strategies for Manufacturing Biopharmaceuticals, 2010, 309-328, Chapter 13.

Perez-Ramirez, Bernardo et al., Preformulation Research: Assessing Protein Solution Behavior Early During Therapeutic Development, Formulation and Process Development Strategies for Manufacturing Biopharmaceuticals, 2010, 119-146, Chapter 5.

(56)          References Cited

OTHER PUBLICATIONS

Shire, Steven J. et al., High Concentration Antibody Formulations, Formulation and Process Development Strategies for Manufacturing Biopharmaceuticals, 2010, 349-381, Chapter 15.

Topp, Elizabeth M. et al., Chemical Instability in Peptide and Protein Pharmaceuticals, Formulation and Process Development Strategies for Manufacturing Biopharmaceuticals, 2010, 41-67, Chapter 2.

Agarkhed, Meera et al., Effect of Polysorbate 80 Concentration on Thermal and Photostability of a Monoclonal Antibody, AAPS Pharm Sci Tech, 14(1), 1-9, 2013.

Falconer, Robert J., Advances in liquid formulations of parenteral therapeutic proteins, Biotechnology Advances, 2019, 1-9, 37(7):107412.

Hada, Shavron et al., Evaluation of antioxidants in protein formulation against oxidative stress using various biophysical methods, International Journal of Biological Macromolecules, 82, (2016), pp. 192-200.

Wang et al., Antibody structure, instability, and formulation, J. Pharm. Sci., 96(1), 1-26, 2007.

Buchbinder, E.I. et al., CTLA-4 and PD-1 Pathways Similarities, Differences, and Implications of Their Inhibition, American Journal of Clinical Oncology, 39(1), 98-106, 2016.

Challener, Cynthia A., For Lyophilization, Excipients Really Do Matter, BioPharm International, 30(1), 32-35, 2017.

Das, Rituparna et al., Combination Therapy with Anti-CTLA-4 and Anti-PD-1 Leads to Distinct Immunologic Changes In Vivo, J Immunol, 194(3), 950-959, 2015.

Ji, J.A. et al., Methionine, Tryptophan, and Histidine Oxidation in a Model Protein, PTH: Mechanisms and Stabilization, J Pharm Sci, 98(12), 4485-4500, 2009.

Manning, Mark Cornell et al., Stability of Protein Pharmaceuticals: An Update, Pharmaceutical Research, 27(4), 544-575, 2010.

Niedziela-Majka, Anita et al., High-Throughput Screening of Formulations to Optimize the Thermal Stability of a Therapeutic Monoclonal Antibody, Journal of Biomolecular Screening, 20(4), 552-559, 2015.

Singh, Surinder M. et al., Effect of Polysorbate 20 and Polysorbate 80 on the Higher Order Structure of a Monoclonal Antibody and its Fab and Fc Fragments Probed Using 2D NMR Spectroscopy, J Pharm Sci, 106(12), 3486-3498, 2017.

Viola, Margarida et al., Subcutaneous delivery of monoclonal antibodies: How do we get there?, Journal of Controlled Release, 286, 301-314, 2018.

Shukla, Diwakar et al., Interaction of Arginine with Proteins and the Mechanism by Which It Inhibits Aggregation, J. Phys. Chem. B., 114, 13426-13438, 2010.

* cited by examiner

FORMULATIONS OF ANTI-RSV ANTIBODIES AND METHODS OF USE THEREOF

CROSS REFERENCE TO RELATED APPLICATIONS

The present application is the 371 national phase application of International Application No. PCT/US2019/056027, filed Oct. 14, 2019, which claims the benefit of U.S. Provisional Application No. 62/747,418, filed Oct. 18, 2018, hereby incorporated by reference in its entirety.

FIELD OF THE INVENTION

The invention relates to stable formulations comprising antibodies or antigen-binding fragments thereof that bind to respiratory syncytial virus (RSV). Also provided are methods of preventing and/or treating RSV-related diseases with the formulations of the invention.

REFERENCE TO SEQUENCE LISTING SUBMITTED ELECTRONICALLY

The sequence listing of the present application is submitted electronically via EFS-Web as an ASCII formatted sequence listing with a file name "24641WOPCT-SEQLIST.TXT", creation date of Oct. 9, 2019, and a size of 9.19 KB. This sequence listing submitted via EFS-Web is part of the specification and is herein incorporated by reference in its entirety.

BACKGROUND OF THE INVENTION

Paramyxoviruses are enveloped negative-strand RNA viruses that are significant human and animal pathogens. Human Respiratory Syncytial Virus (hRSV, RSV) belongs to the family Paramyxoviridae, subfamily Pneumovirinae. Two subtypes, type A and type B, have been identified and are a major cause of severe and sometimes even fatal respiratory infections in children less than 6 months of age. Adults with underlying diseases, such as COPD, asthma, and cancer, and adults with immunocompromised status, including HIV or post transplantation, are also at risk of developing severe RSV infection. Fifteen percent of annual hospitalizations in adults over 50 years due to acute respiratory infection are caused by RSV. In the United States, RSV causes more than 100,000 hospitalizations annually, and it is estimated to cause about 160,000 deaths globally each year. Currently there is no vaccine for RSV, and a trial with a formalin-inactivated virus was associated with increased disease severity in infants upon infection with RSV. Other family members including Human Metapneumo Virus (hMPV) and Human Parainfluenza Virus (hPIV) are also responsible for acute respiratory illness similar to hRSV.

The hRSV genome is a single-stranded negative-sense RNA molecule of approximately 15 kb that encodes 11 proteins. Two of these proteins are the main surface glycoproteins of the virion. These are (i) the attachment (G) protein, which mediates virus binding to cells, and (ii) the fusion (F) protein, which promotes both fusion of the viral and cell membranes at the initial stages of the infectious cycle and fusion of the membrane of infected cells with those of adjacent cells to form characteristic syncytia. The attachment protein G binds cellular surface receptors and interacts with the F protein. This interaction triggers a conformational change in the F protein to induce membrane fusion, thereby releasing the viral ribonucleoprotein complex into the host cell cytoplasm.

Monoclonal antibodies against the F protein or the G protein have been shown to have neutralizing effects in vitro and prophylactic effects in vivo. See, e.g., Beeler and Coelingh 1989, J. Virol. 63:2941-50; Garcia-Barreno et al., 1989, J. Virol. 63:925-32; Taylor et al., 1984, Immunology 52: 137-142; Walsh et al., 1984, Infection and Immunity 43:756-758; and U.S. Pat. Nos. 5,842,307 and 6,818,216. Other hRSV antibodies are described in International Patent Application Nos. WO94/06448 and WO92/04381 and U.S. Pat. Nos. 8,221,759 and 9,963,500.

Antibodies for use in human subjects must be stored prior to use and transported to the point of administration. Reproducibly attaining a desired level of antibody drug in a subject requires that the drug be stored in a formulation that maintains the bioactivity of the drug. The need exists for stable formulations of anti-RSV antibodies for pharmaceutical use, e.g., for preventing and/or treating RSV-related diseases. Preferably, such formulations will exhibit a long shelf-life, be stable when stored and transported, and will be amenable to administration at high concentrations, e.g. for use in subcutaneous administration, as well as low concentrations, e.g. for intravenous administration.

The formulations of the invention are useful for subcutaneous delivery to a patient in need thereof. In order to deliver maximum therapeutic benefits to patients, it is desirable that formulations for subcutaneous (SC) delivery comprise a high antibody concentration (75-200 mg/ml). A high concentration of API is often required for SC formulations due to the historical bioavailability of 50-60% for SC injections and the expected dose range of an antibody product. However, high concentration of antibody, or antigen-binding fragment thereof, may contribute to other properties of the product which would be undesirable, e.g. low injectability due to increased viscosity and higher than physiological osmolality and increased aggregation. Therefore, it is preferred that an antibody product intended for SC administration balances the effects of concentration while maintaining a level of drug that will provide the highest therapeutic benefit. An ideal product comprises a high protein concentration, low viscosity, an osmolality similar to physiological conditions, and a low level of aggregation under typical storage conditions. Increased viscosity at high protein concentration may not only make it difficult to extract the product from its container with a syringe, but also to inject the necessary dose into a patient from the syringe (syringeability). Advantageously, embodiments of the invention provide formulations that comprise a high concentration of antibody, or antigen-binding fragment thereof, and a viscosity level that is acceptable for subcutaneous delivery. Additionally, the formulations of the invention do not lead to high levels of aggregation, as shown in more detail throughout the Examples.

SUMMARY OF THE INVENTION

The present disclosure provides an anti-RSV antibody formulation, comprising: a) about 50 mg/mL to about 250 mg/mL of an anti-RSV antibody, or antigen-binding fragment thereof, b) about 5 mM to about 20 mM buffer; c) a stabilizer selected from the group consisting of: (i) about 6% to about 8% weight/volume (w/v) non-reducing sugar; (ii) about 25 mM to about 75 mM each of L-arginine, or a pharmaceutically acceptable salt of L-arginine, L-proline, or a pharmaceutically acceptable salt of L-proline; L-lysine, or a pharmaceutically acceptable salt of L-lysine; L-glutamate, or a pharmaceutically acceptable salt of L-glutamate, or a mixture of the amino acids described herein, and (iii) about 25 µM to 75 µM of a chelator; d) about 0.01% to about 0.10% non-ionic surfactant; and e) about 1 mM to about 20 mM anti-oxidant.

In another embodiment, the disclosure provides an anti-RSV antibody formulation, comprising: a) about 50 mg/mL to about 150 mg/mL of an anti-RSV antibody, or antigen-binding fragment thereof, b) about 5 mM to about 20 mM histidine; c) about 6% to about 8% weight/volume (w/v) sucrose; d) an excipient selected from about 25 mM to about 75 mM of L-arginine or a pharmaceutically acceptable salt of L-arginine, about 25 mM to about 75 mM L-lysine or a pharmaceutically acceptable salt of L-lysine, a mixture of about 25 mM to about 75 mM L-arginine and about 25 to about 75 mM L-glutamate, and a mixture of about 25 mM to about 75 mM of L-arginine(HCl) and about 25 to about 75 mM L-lysine(HCl); e) about 25 µM to 75 M of DTPA; f) about 0.01% to about 0.10% polysorbate 80; and optionally g) about 1 mM to about 20 mM L-methionine.

In another embodiment, the disclosure provides an anti-RSV antibody formulation, comprising: a) about 100 mg/mL of an anti-RSV antibody, or antigen-binding fragment thereof, b) about 10 mM histidine; c) about 7% weight/volume (w/v) sucrose; d) an excipient selected from about 50 mM L-arginine(HCl), about 50 mM L-lysine(HCl), a mixture of about 25 mM L-arginine and about 25 mM L-glutamate, and a mixture of about 25 mM L-arginine(HCl) and about 25 mM L-lysine(HCl); e) about 50 µM DTPA; f) about 0.02% polysorbate 80; and optionally g) about 1 mM to 20 mM L-methionine.

In another embodiment, the disclosure provides an anti-RSV antibody formulation, comprising: a) 100 mg/mL of an anti-RSV antibody, or antigen-binding fragment thereof, b) 10 mM histidine; c) 7% weight/volume (w/v) sucrose; d) an excipient selected from 50 mM L-arginine(HCl), 50 mM L-lysine(HCl), a mixture of 25 mM L-arginine and 25 mM L-glutamate, and a mixture of 25 mM L-arginine(HCl) and 25 mM L-lysine(HCl); e) 50 M DTPA; f) 0.02% polysorbate 80; and optionally g) 1 mM to 20 mM L-methionine.

In another embodiment, the disclosure provides an anti-RSV antibody formulation, comprising: a) 100 mg/mL of an anti-RSV antibody, or antigen-binding fragment thereof, b) 10 mM histidine; c) 7% weight/volume (w/v) sucrose; d) a mixture of 25 mM L-arginine(HCl) and 25 mM L-lysine (HCl); e) 50 µM DTPA; and f) 0.02% polysorbate 80.

In another embodiment, the disclosure provides an anti-RSV antibody formulation consisting of: a) 100 mg/mL of an anti-RSV antibody, or antigen-binding fragment thereof, b) 10 mM histidine; c) 7% weight/volume (w/v) sucrose; d) a mixture of 25 mM L-arginine(HCl) and 25 mM L-lysine (HCl); e) 50 M DTPA; and f) 0.02% polysorbate 80.

In one aspect, the disclosure provides an anti-RSV antibody formulation comprising: a) about 50 mg/mL to about 250 mg/mL of an anti-RSV antibody, or antigen-binding fragment thereof; b) about 5 mM to about 20 mM histidine; c) about 4% to about 8% (w/v) sucrose; d) an excipient selected from the group consisting of about 25 mM to about 75 mM of L-arginine or a pharmaceutically acceptable salt of L-arginine, about 25 mM to about 75 mM of L-lysine or a pharmaceutically acceptable salt of L-lysine, a mixture of about 25 mM to about 75 mM L-arginine or a pharmaceutically acceptable salt of L-arginine and about 25 mM to about 75 mM L-glutamate or a pharmaceutically acceptable salt of L-glutamate, and a mixture of about 25 mM to about 75 mM of L-arginine or a pharmaceutically acceptable salt of L-arginine and about 25 mM to about 75 mM L-lysine or a pharmaceutically acceptable salt of L-lysine; and e) about 0.01% to about 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) about 25 mM to about 75 mM of L-arginine or a pharmaceutically acceptable salt of L-arginine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof, b) 5 mM to 20 mM histidine; c) 4% to 8% (w/v) sucrose; d) 25 mM to 75 mM of L-arginine or a pharmaceutically acceptable salt of L-arginine; and e) 0.01% to 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) about 25 mM to about 75 mM of L-lysine or a pharmaceutically acceptable salt of L-lysine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof, b) 5 mM to 20 mM histidine; c) 4% to 8% (w/v) sucrose; d) 25 mM to 75 mM of L-lysine or a pharmaceutically acceptable salt of L-lysine; and e) 0.01% to 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) a mixture of about 25 mM to about 75 mM L-arginine or a pharmaceutically acceptable salt of L-arginine and about 25 mM to about 75 mM L-glutamate or a pharmaceutically acceptable salt of L-glutamate; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof; b) 5 mM to 20 mM histidine; c) 4% to about 8% (w/v) sucrose; d) a mixture of 25 mM to 75 mM L-arginine or a pharmaceutically acceptable salt of L-arginine and 25 mM to 75 mM L-glutamate or a pharmaceutically acceptable salt of L-glutamate; and e) 0.01% to 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) a mixture of about 25 mM to about 75 mM of L-arginine or a pharmaceutically acceptable salt of L-arginine and about 25 mM to about 75 mM L-lysine or a pharmaceutically acceptable salt of L-lysine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof; b) 5 mM to 20 mM histidine; c) 4% to 8% (w/v) sucrose; d) a mixture of 25 mM to 75 mM of L-arginine or a pharmaceutically acceptable salt of L-arginine and 25 mM to 75 mM L-lysine or a pharmaceutically acceptable salt of L-lysine; and e) 0.01% to 0.10% (w/v) polysorbate 80.

In certain embodiments, the formulation has a pH between 5.5 and 6.5.

In certain embodiments, the formulation has a pH of 6.0.

Also provided herein are methods of preventing and/or treating RSV-related diseases in a human patient in need thereof comprising: administering an effective amount of the anti-RSV antibody formulations of the invention to the patient.

Also provided herein are methods of treating or preventing RSV infection in a human patient in need thereof comprising: administering an effective amount of the anti-RSV antibody formulations of the invention to the patient.

Also provided herein are methods of treating or preventing RSV infection in a human patient in need thereof comprising: administering an effective amount of the anti-RSV antibody formulations of the invention to the patient wherein the effective amount comprises a fixed dose of an anti-RSV antibody or antigen-binding fragment thereof, wherein the fixed dose ranges from about 10 to about 100 mg.

Also provided herein are methods of treating or preventing RSV infection in a human patient in need thereof comprising: administering an effective amount of the anti-RSV antibody formulations of the invention to the patient wherein the anti-RSV antibody formulations are administered by subcutaneous administration; or wherein the anti-RSV antibody formulations are administered by intravenous administration; or wherein the anti-RSV antibody formulations are administered by intramuscular administration.

Also provided herein is the use of the anti-RSV antibody formulations of the invention for the treatment or prevention of RSV infection in a human patient.

6

Figure 13A:
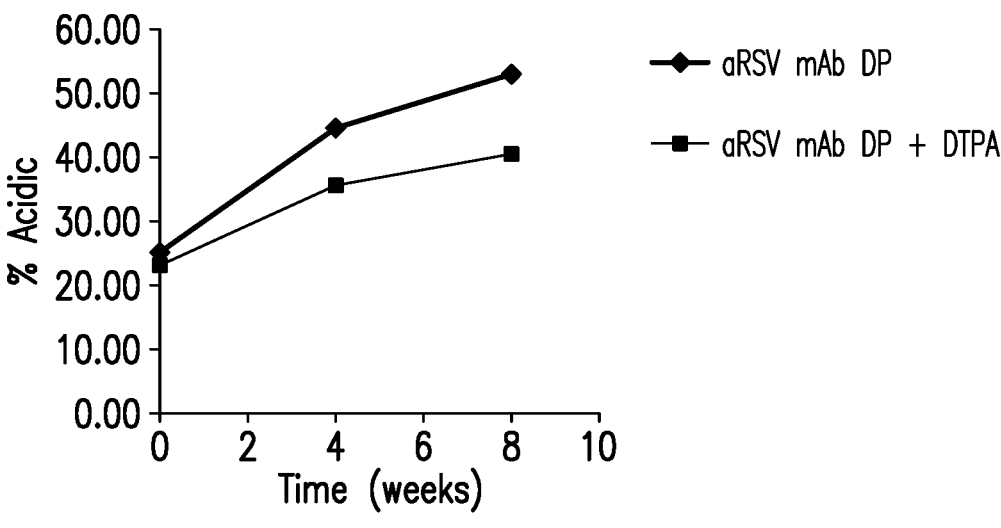
Figure 13B:
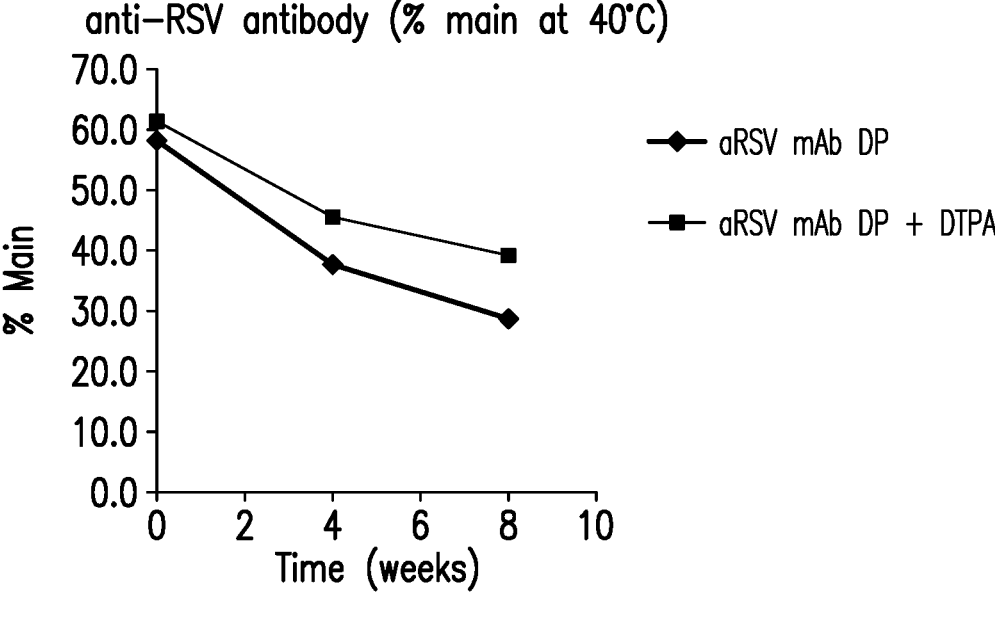

FIGS. 13A-13B show results of HP-IEX % Total Acidic Peaks and % Main Peak vs. Time of an anti-RSV antibody formulations at 40° C. storage conditions.

Figure 14:
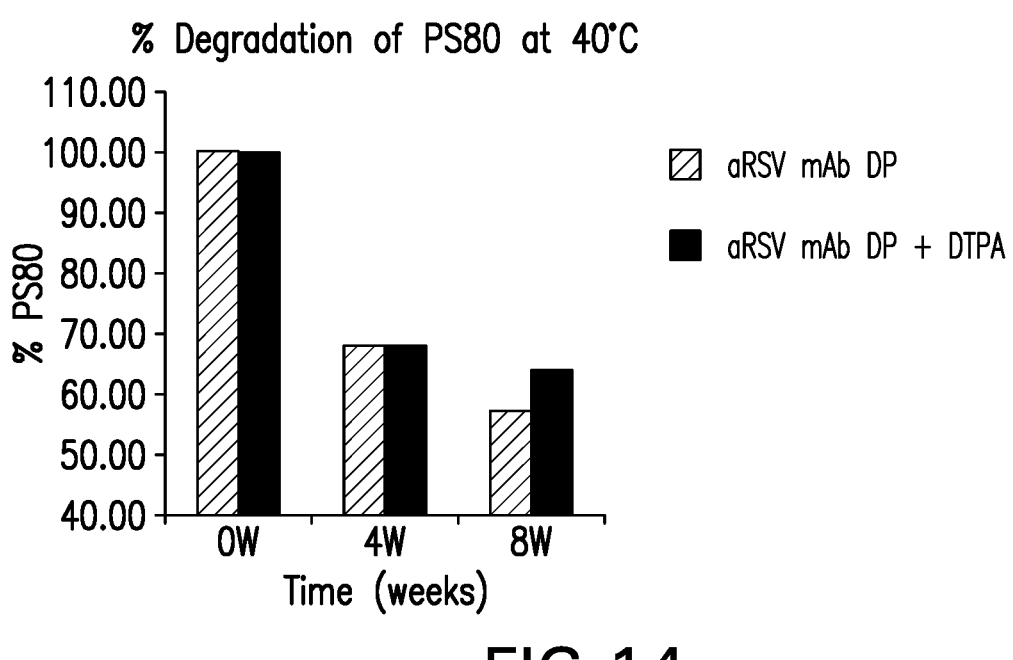

FIG. 14 shows results of the percentage degradation of PS80 at 40° C.

Figure 15:
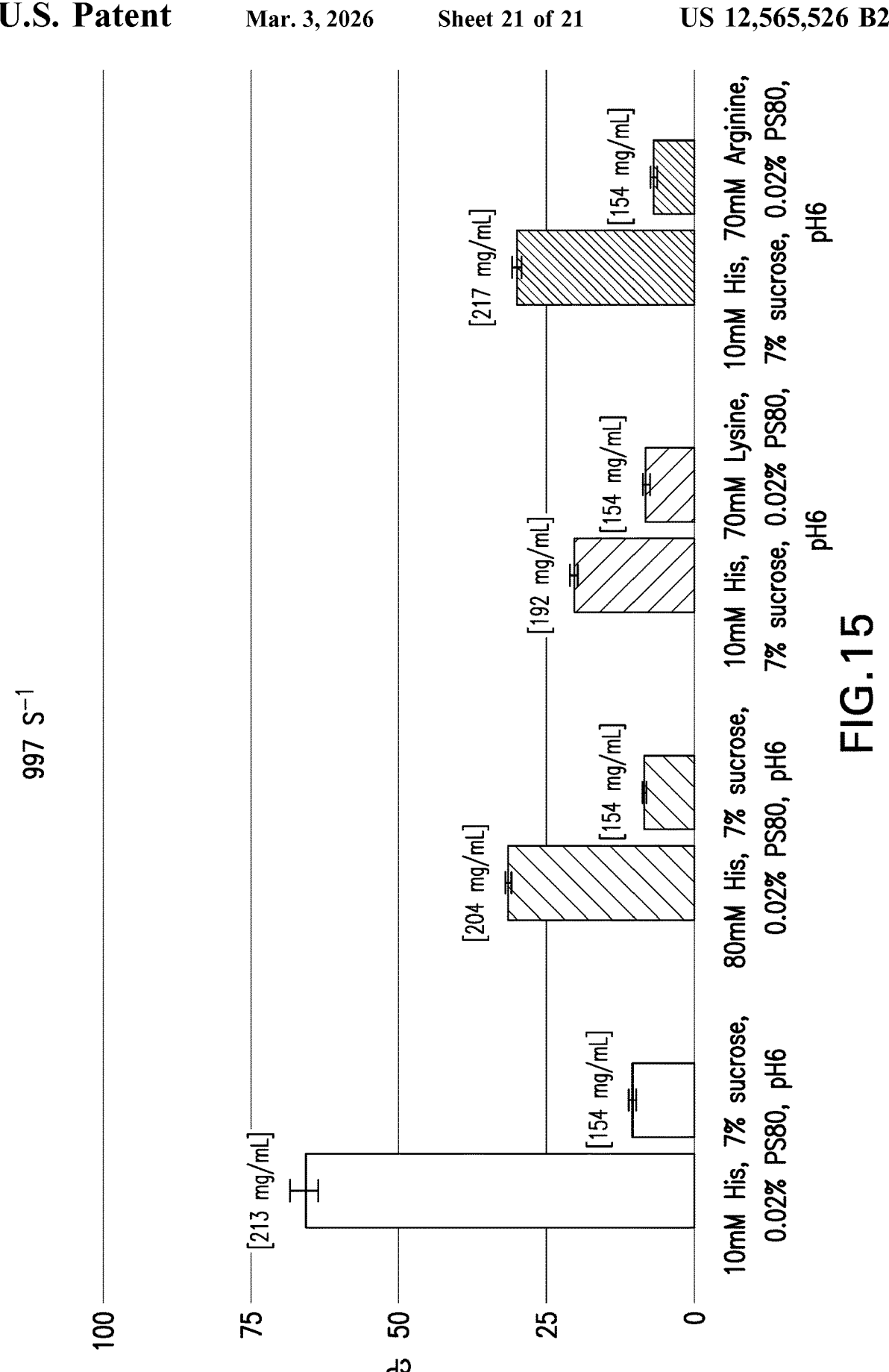

FIG. 15 shows a bar graph comparing viscosity of formulations using excipients of 80 mM histidine, 70 mM lysine or 70 mM arginine.

DETAILED DESCRIPTION OF THE INVENTION

The invention provides stable formulations comprising an anti-RSV antibody, or antigen-binding fragment thereof that binds to RSV. The invention provides stable formulations comprising an anti-RSV antibody, or antigen-binding fragment thereof that binds to human RSV F-protein, which are useful for methods of treating or preventing human RSV infection.

Antibodies useful in the formulations disclosed herein are described in U.S. Pat. No. 9,963,500. An exemplary antibody, useful in the formulations disclosed herein, is described in U.S. Pat. No. 9,963,500. This exemplary antibody comprises complementarity-determining regions (CDRs) having the amino acid sequences: SEQ ID NO: 1 (heavy chain CDR 1), SEQ ID NO: 2 (heavy chain CDR 2), SEQ ID NO: 3 (heavy chain CDR 3), SEQ ID NO: 4 (light chain CDR 1), SEQ ID NO: 5 (light chain CDR 2), and SEQ ID NO: 6 (light chain CDR 3). Further, this exemplary antibody comprises heavy and light chain variable regions having the amino acid sequences of SEQ ID NO: 7 and SEQ ID NO:8. Further, this exemplary antibody comprises a heavy and light chain immunoglobulin consisting of the amino acid sequences of SEQ ID NO: 9 and SEQ ID NO: 10.

I. Definitions and Abbreviations

Definitions are utilized throughout the specification. Abbreviations are defined throughout the specification and claims.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

When a range of values is recited, such as "an amount between 50 mg and 100 mg" the range is intended to be inclusive of the recited values.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"RSV-related disease" means any disease caused, directly or indirectly, by an infection with Respiratory Syncytial Virus (RSV) as well as diseases or conditions which predispose a patient to infection by RSV. Examples of diseases falling into the former category include pneumonia and bronchiolitis. Diseases and conditions in the latter category (i.e., those which place the patient at risk of severe RSV infection) include cystic fibrosis, congenital heart disease, cancer, age related immunosuppression, transplant recipients and, generally, any condition that causes a state of immunosuppression or decreased function of the immune system such as post-operative organ transplantation regimens or premature birth.

"Treat" or "treating" means to administer a therapeutic agent, such as a formulation containing any of the antibodies or antigen-binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. Treatment with anti-RSV antibodies could also be combined with other interventions (antibodies, nucleic acids, vaccines and small molecule compounds) to treat other respiratory pathogens.

"Prevent" or "preventing" means to administer a prophylactic agent, such as a formulation containing any of the antibodies or antigen-binding fragments of the present invention, internally or externally to a subject or patient at risk of becoming infected by RSV, for which the agent has prophylactic activity. Preventing includes reducing the likelihood or severity of a subsequent RSV infection, ameliorating symptoms associated with lower respiratory tract infection (LRI) upon RSV infection, and inducing immunity to protect against RSV infection. Typically, the agent is administered in an amount effective to neutralize RSV in the lungs and/or the nose in order block infection. The amount of a prophylactic agent that is effective to ameliorate any particular disease symptom may vary according to factors such as the age, and weight of the patient, and the ability of the agent to elicit a desired response in the subject. Whether a disease symptom has been ameliorated can be assessed by any clinical measurement typically used by physicians or other skilled healthcare providers to assess the severity or progression status of that symptom or in certain instances will ameliorate the need for hospitalization.

The term "patient" (alternatively referred to as "subject" or "individual" herein) refers to a mammal (e.g., rat, mouse, dog, cat, rabbit) capable of being treated with the formulations of the invention, most preferably a human. In some embodiments, the patient is an adult patient. In other embodiments, the patient is a pediatric patient. Those "in need of treatment" include those patients that may benefit from treatment with the formulations of the invention.

The term "pharmaceutically effective amount" or "effective amount" means an amount whereby a sufficient therapeutic formulation is introduced to a patient to treat a disease or condition. One skilled in the art recognizes that this level may vary according the patient's characteristics such as age, weight, etc.

As used herein, the phrase "fixed dose" refers to an amount (e.g. in milligrams) of active ingredient that is administered to a patient.

The term "about", when modifying the quantity (e.g., mM, or M) of a substance or formulation, the percentage (v/v or w/v) of a formulation component, the pH of a solution/formulation, or the value of a parameter characterizing a step in a method, or the like, refers to variation in the numerical quantity of plus or minus 5%. Such variation in the numerical quantity can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like.

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or formulation. As a non-limiting example, a binding compound that consists essentially of a recited amino acid sequence may also include one or more amino acids, including substitutions of one or more amino acid residues, that do not materially affect the properties of the binding compound.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

The phrase "pharmaceutical formulation" refers to preparations which are in such form as to permit the active ingredients to be effective, and which contains no additional components which are toxic to the subjects to which the formulation would be administered. The term "formulation" and "pharmaceutical formulation" are used interchangeably throughout.

The phrase "Pharmaceutically acceptable" refers to excipients (vehicles, additives) and compositions that can reasonably be administered to a subject to provide an effective dose of the active ingredient employed and that are "generally regarded as safe" e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period. For example, in one embodiment, a stable formulation is a formulation with no significant changes observed at a refrigerated temperature (2-8° C.) for at least 12 months. In another embodiment, a stable formulation is a formulation with no significant changes observed at a refrigerated temperature (2-8° C.) for at least 18 months. In another embodiment, stable formulation is a formulation with no significant changes observed at room temperature (23-27° C.) for at least 3 months. In another embodiment, stable formulation is a formulation with no significant changes observed at room temperature (23-27° C.) for at least 6 months. In another embodiment, stable formulation is a formulation with no significant changes observed at room temperature (23-27° C.) for at least 12 months. In another embodiment, stable formulation is a formulation with no significant changes observed at room temperature (23-27° C.) for at least 18 months. The criteria for stability for an antibody formulation are as follows. Typically, no more than 10%, preferably 5%, of antibody monomer is degraded as measured by SEC-HPLC. Typically, the formulation is colorless, or clear to slightly opalescent by visual analysis. Typically, the concentration, pH and osmolality of the formulation have no more than +/−10% change. Potency is typically within 60-140%, preferably 80-120%, of the control or reference. Typically, no more than 10%, preferably 5%, of clipping of the antibody is observed, i.e., % low molecular weight species as determined, for example, by HP-SEC. Typically, no more than 10%, preferably no more than 5%, of aggregation of the antibody is observed, i.e. % high molecular weight species as determined, for example, by HP-SEC.

The phrase "anti-RSV antibody" refers to a monoclonal antibody directed against the F protein or the G protein of RSV. Anti-RSV antibodies are disclosed and described in U.S. Pat. No. 9,963,500. A particular anti-RSV antibody is disclosed and described in U.S. Pat. No. 9,963,500 and comprises complementarity-determining regions (CDRs) having the amino acid sequences: SEQ ID NO: 1 (heavy chain CDR 1), SEQ ID NO: 2 (heavy chain CDR 2), SEQ ID NO: 3 (heavy chain CDR 3), SEQ ID NO: 4 (light chain CDR 1), SEQ ID NO: 5 (light chain CDR 2), and SEQ ID NO: 6 (light chain CDR 3). Further, an anti-RSV antibody is disclosed and described in U.S. Pat. No. 9,963,500 and comprises heavy and light chain variable regions having the amino acid sequences of SEQ ID NO: 7 and SEQ ID NO: 8, respectively. Further, a particular anti-RSV antibody is disclosed and described in U.S. Pat. No. 9,963,500 and comprises a heavy and light chain immunoglobulin consisting of the amino acid sequences of SEQ ID NO: 9 and SEQ ID NO: 10, respectively.

An antibody "retains its physical stability" in a pharmaceutical formulation if it shows no significant increase of aggregation, precipitation and/or denaturation upon visual examination of color and/or clarity, or as measured by UV light scattering, size exclusion chromatography (SEC) and dynamic light scattering. The changes of protein conformation can be evaluated by fluorescence spectroscopy, which determines the protein tertiary structure, and by FTIR spectroscopy, which determines the protein secondary structure.

An antibody "retains its chemical stability" in a pharmaceutical formulation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical formulation, if the biological activity of the antibody at a given time is within a predetermined range of the biological activity exhibited at the time the pharmaceutical formulation was prepared. The biological activity of an antibody can be determined, for example, by an antigen-binding assay. Formulations of the invention include antibodies and fragments thereof that are biologically active when reconstituted or in liquid form.

II. Formulations of the Invention

The formulations of the invention minimize the formation of antibody aggregates, increase stability and reduce viscosity.

The invention includes various formulations of an anti-RSV antibody, or antigen-binding fragment thereof, as described in more detail below. For example, the invention includes formulations comprising (i) an anti-RSV antibody or antigen-binding fragment thereof, (ii) a buffer (e.g., histidine), (iii) a stabilizer (e.g., a non-reducing sugar such as sucrose); (iv) a non-ionic surfactant (e.g., polysorbate 80); and (v) an antioxidant (e.g., methionine). In further embodiments, the formulations of the invention comprise a viscosity-reducer (e.g. arginine, or a pharmaceutically acceptable salt thereof; lysine, or a pharmaceutically acceptable salt thereof, a mixture of arginine and lysine or pharmaceutically acceptable salts thereof, a mixture of arginine and glutamate or pharmaceutically acceptable salts thereof, and/or histidine or pharmaceutically acceptable salts thereof) and/or a metal chelator (e.g. DTPA).

III. Anti-RSV Antibodies and Antigen-Binding Fragments Thereof

The invention provides stable biological formulations comprising an anti-RSV antibody which comprises complementarity-determining regions (CDRs) having the amino acid sequences: SEQ ID NO: 1 (heavy chain CDR 1), SEQ ID NO: 2 (heavy chain CDR 2), SEQ ID NO: 3 (heavy chain CDR 3), SEQ ID NO: 4 (light chain CDR 1), SEQ ID NO: 5 (light chain CDR 2), and SEQ ID NO: 6 (light chain CDR 3). The invention also provides stable biological formulations comprising an anti-RSV antibody which comprises heavy and light chain variable regions having the amino acid sequences of SEQ ID NO: 7 and SEQ ID NO: 8, respectively and/or comprises a heavy and light chain immunoglobulin consisting of the amino acid sequences of SEQ ID NO: 9 and SEQ ID NO: 10 respectively. The methods of making the anti-RSV antibody are disclosed and described in U.S. Pat. No. 9,963,500 and are hereby incorporated by reference in its entirety. SEQ ID NOs: 1-10 are set forth in Table A below:

TABLE A

Sequence Information

| SEQ ID NO: | SEQUENCE |
|---|---|
| 1 | DSAMS |
| 2 | FIKSKTYGGTKEYAASVKG |
| 3 | GAPYGGNSDYYYGLDV |
| 4 | RTSQDVRGALA |
| 5 | DASSLET |
| 6 | QQFLDFPFT |
| 7 | EVQLVESGGGLVRPGRSLRLSCTVSGFSFDDSAMSWVRQAPG<br>KGLEWISFIKSKTYGGTKEYAASVKGRFTISRDDSKNIAYLQ<br>MNSLKTEDTAVYYCTRGAPYGGNSDYYYGLDVWGQGTTVT |
| 8 | MTQSPSSLSASVGDRVTITCRTSQDVRGALAWYQQKPGKAPK<br>LLIFDASSLETGVPSRFSGSGSGTVFTLTISSLQPEDFAAYY<br>CQQFLDFPFTFGQGTRLEIKRT |
| 9 | EVQLVESGGGLVRPGRSLRLSCTVSGFSFDDSAMSWVRQAPG<br>KGLEWISFIKSKTYGGTKEYAASVKGRFTISRDDSKNIAYLQ<br>MNSLKTEDTAVYYCTRGAPYGGNSDYYYGLDVWGQGTTVTVS<br>SASTKGPSVFPLAPSSKSISGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPELLGGPSVFL<br>FPPKPKDTLYITREPEVTCVVVDVSHEDPEVKFNWYVDGVEV<br>HNAKTKPREEQYNSTYRVVSVLTVLHQDWLNGKEYKCKVSNK<br>ALPAPIEKTISKAKGQPREPQVYTLPPSRDELTKNQVSLTCL<br>VKGFYPSDIAVEWESNGQPENNYKTTPPVLDSDGSFFLYSKL<br>TVDKSRWQQGNVFSCSVMHEALHNHYTQKSL SLSPGK |
| 10 | DIQMTQSPSSLSASVGDRVTITCRTSQDVRGALAWYQQKPGK<br>APKLLIFDASSLETGVPSRFSGSGSGTVFTLTISSLQPEDFA<br>AYYCQQFLDFPFTFGQGTRLEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFN<br>RGEC |

In some embodiments of the formulations described herein, the API ("active pharmaceutical ingredient", i.e. the anti-RSV antibody or antigen-binding fragment thereof) is present in a concentration of about 50 mg/mL to about 250 mg/mL. In some embodiments of the formulations, the API (i.e. the anti-RSV antibody or antigen-binding fragment thereof) is present in a concentration of about 75 mg/mL to about 200 mg/mL. In some embodiments, the API is present in a concentration of about 90 mg/mL to about 110 mg/mL. In another embodiment, the API is present in a concentration of about 100 mg/mL. In another embodiment, the API is present in a concentration of 90 mg/mL to 110 mg/mL. In another embodiment, the API is present in a concentration of 100 mg/mL. In another embodiment, the API is present in a concentration of 75 mg/mL. In another embodiment, the API is present in a concentration of 50 mg/mL.

In some embodiments, the API is present in a concentration of about 125 mg/mL to about 175 mg/mL. In some embodiments, the API is present in a concentration of about 140 mg/mL to about 160 mg/mL. In another embodiment, the API is present in a concentration of about 150 mg/mL. In some embodiments, the API is present in a concentration of 125 mg/mL to 175 mg/mL. In some embodiments, the API is present in a concentration of 140 mg/mL to 160 mg/mL. In another embodiment, the API is present in a concentration of 150 mg/mL.

In some embodiments, the API is present in a concentration of about 150 mg/mL to about 200 mg/mL. In some embodiments, the API is present in a concentration of about 165 mg/mL to about 185 mg/mL. In another embodiment, the API is present in a concentration of about 175 mg/mL. In some embodiments, the API is present in a concentration of 150 mg/mL to 200 mg/mL. In some embodiments, the API is present in a concentration of 165 mg/mL to 185 mg/mL. In another embodiment, the API is present in a concentration of 175 mg/mL.

In some embodiments, the API is present in a concentration of about 175 mg/mL to about 225 mg/mL. In some embodiments, the API is present in a concentration of about 190 mg/mL to about 210 mg/mL. In another embodiment, the API is present in a concentration of about 200 mg/mL. In some embodiments, the API is present in a concentration of 175 mg/mL to 225 mg/mL. In some embodiments, the API is present in a concentration of 190 mg/mL to 210 mg/mL. In another embodiment, the API is present in a concentration of 200 mg/mL.

In some embodiments, the API is present in a concentration of about 200 mg/mL to about 250 mg/mL. In some embodiments, the API is present in a concentration of about 215 mg/mL to about 235 mg/mL. In another embodiment, the API is present in a concentration of about 225 mg/mL. In some embodiments, the API is present in a concentration of 200 mg/mL to 250 mg/mL. In some embodiments, the API is present in a concentration of 215 mg/mL to 235 mg/mL. In another embodiment, the API is present in a concentration of 225 mg/mL.

In some embodiments of the formulations disclosed herein, the API (i.e. the anti-RSV antibody or antigen-binding fragment thereof) is present in a fixed dose (e.g. an amount in milligrams). In some embodiments of the formulations disclosed herein, the API is present in a fixed dose of about 10 mg to about 150 mg. In some embodiments, the API is present in a fixed dose of 10 mg to 150 mg. In some embodiments, the API is present in a fixed dose of about 25 mg to about 125 mg. In some embodiments, the API is present in a fixed dose of 25 mg to 125 mg. In some embodiments, the API is present in a fixed dose of about 50 mg to about 100 mg. In some embodiments, the API is present in a fixed dose of 50 mg to 100 mg.

IV. Formulation Excipients

The formulations of the invention comprise at least one excipient that stabilizes the formulation.

In some embodiments of the formulations of the invention, the stabilizer is a non-reducing sugar. In embodiments of the invention, the non-reducing sugar is sucrose. In further embodiments, the non-reducing sugar is glucose. In additional embodiments, the non-reducing sugar is trehalose. In still further embodiments, the non-reducing sugar is lactose. In other embodiments, the non-reducing sugar is raffinose.

In some embodiments, the anti-RSV antibody formulations of the invention comprise a stabilizer selected from the group consisting of: about 4% to about 8% weight/volume (w/v) sucrose, glucose, trehalose, lactose or raffinose.

In some embodiments, the stabilizer is about 4% to about 8% w/v sucrose. In some embodiments, the stabilizer is 4% to 8% w/v sucrose.

In some embodiments, the stabilizer is about 6% to about 8% w/v sucrose.

In some embodiments, the stabilizer is 4% to 8% w/v sucrose.

In some embodiments, the stabilizer is about 4% to about 8% w/v trehalose. In some embodiments, the stabilizer is 4% to 8% w/v trehalose.

In some embodiments, the stabilizer is about 6% to about 8% w/v trehalose. In some embodiments, the stabilizer is 6% to 8% w/v trehalose.

In some embodiments, the stabilizer is about 6.5% to about 7.5% w/v sucrose. In some embodiments, the stabilizer is 6.5% to 7.5% w/v sucrose.

In some embodiments, the stabilizer is 6% to 8% sucrose.

In some embodiments, the stabilizer is 6.5% to 7.5% w/v sucrose.

In some embodiments, the stabilizer is 7% sucrose.

The formulations of the invention comprise arginine, e.g., L-arginine, or a pharmaceutically acceptable salt thereof, e.g., HCl; lysine, e.g., L-lysine, or a pharmaceutically acceptable salt thereof, e.g., HCl; or a combination of arginine (L-arginine), or a pharmaceutically acceptable salt (HCl) thereof and lysine (L-lysine), or a pharmaceutically acceptable salt (HCl) thereof; or a combination of arginine (L-arginine), or a pharmaceutically acceptable salt (HCl) thereof and glutamate (L-glutamate), or a pharmaceutically acceptable salt thereof; all of which may provide additional stability to the formulation, as well as control viscosity, which allows formulation at high API concentration.

In addition to an anti-RSV antibody or antigen-binding fragment thereof, and a stabilizer in the amounts/concentrations specified above, the formulations of the invention also comprise a buffer. In some embodiments, the buffer is present in an amount of about 5 mM to about 20 mM, which provides for a pH in the range of about 5 to about 7. In some embodiments, the buffer is present in an amount of 5 mM to 20 mM, which provides for a pH in the range of 5 to 7.

In some embodiments of the invention, the buffer provides the formulation a pH in the range from about 5.5 to about 6.5. In some embodiments of the invention, the buffer provides the formulation a pH in the range from 5.5 to 6.5. In some embodiments, the buffer has a pH in a range of about 6.0. In still further embodiments, the pH is 6.0.

In particular embodiments, the buffer has a pH of about 5.7, about 5.8, about 5.9, about 6.0, about 6.1, about 6.2, or about 6.3. In particular embodiments, the buffer has a pH of 5.7, 5.8, 5.9, 6.0, 6.1, 6.2, or 6.3. Examples of buffers that will control the pH in this range include succinate (sodium or potassium), histidine, sodium acetate, phosphate (sodium or potassium), Tris (tris (hydroxymethyl) aminomethane), diethanolamine, citrate (sodium) and other organic acid buffers.

In some embodiments of the invention, the buffer is histidine or acetate at a pH of about 5.5 to about 6.5. In some embodiments of the invention, the buffer is histidine or acetate at a pH of 5.5 to 6.5. In some embodiments, the buffer is an L-histidine buffer. In embodiments where the formulation is lyophilized, it is preferred that the buffer is not acetate because acetate buffer systems are not compatible with the lyophilization process.

When a range of pH values is recited, such as "a pH between 5.5 and 6.5," the range is intended to be inclusive of the recited values. Unless otherwise indicated, for lyophilized formula the pH refers to the pH after reconstitution of the lyophilized formulations of the invention. The pH is typically measured at 25° C. using standard glass bulb pH meter. As used herein, a solution comprising "histidine buffer at pH X" refers to a solution at pH X and comprising the histidine buffer, i.e. the pH is intended to refer to the pH of the solution.

In addition to an anti-RSV antibody or antigen-binding fragment thereof, a stabilizer, and a buffer in the amounts/concentrations specified above, the formulations of the invention also comprise an anti-oxidant. In embodiments of the invention, the anti-oxidant is methionine. In embodiments of the invention, the anti-oxidant is L-methionine, or a pharmaceutically acceptable salt thereof. In further embodiments, the methionine is L-methionine. In other embodiments, the anti-oxidant is L-methionine HCl. In other embodiments, the anti-oxidant is histidine.

In some embodiments, the anti-oxidant (e.g. L-methionine) is present in the formulations of the invention in an amount of about 1 mM to about 20 mM. In some embodiments, the anti-oxidant is present in an amount of about 5 mM to about 20 mM, about 5 mM to about 15 mM, about 5 mM to about 10 mM. In some embodiments, the anti-oxidant is present in an amount of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM. In some embodiments, the anti-oxidant is present in an amount of 5 mM to 20 mM, 5 mM to 15 mM, 5 mM to 10 mM. In some embodiments, the anti-oxidant is present in an amount of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM or 20 mM.

In embodiments wherein the anti-oxidant is histidine, the histidine can be present in amounts up to 100 mM. In such embodiments, histidine can serve as a buffer, an anti-oxidant, and/or to reduce viscosity in the formulations described herein. In some embodiments, histidine may be present in a concentration of about 10-20 mM, about 20-30 mM, about 30-40 mM, about 40-50 mM, about 50-60 mM, about 60-70 mM, about 70-80 mM, about 80-90 mM, or about 90-100 mM. In some embodiments, histidine may be present in a concentration of 10-20 mM, 20-30 mM, 30-40 mM, 40-50 mM, 50-60 mM, 60-70 mM, 70-80 mM, 80-90 mM, or 90-100 mM. In some embodiments, histidine may be present in a concentration of about 10 mM, about 20 mM, about 30 mM, about 40 mM, about 50 mM, about 60 mM, about 70 mM, about 80 mM, about 90 mM, or about 100 mM. In some embodiments, histidine may be present in a concentration of 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM.

In addition to an anti-RSV antibody or antigen-binding fragment thereof, a stabilizer, a buffer, and an anti-oxidant in the amounts/concentrations specified above, the formulations of the invention also comprise a surfactant. Surfactants are typically added to formulations to provide stability, reduce and/or prevent aggregation or to prevent and/or inhibit protein damage during processing conditions such as purification, filtration, freeze-drying, transportation, storage, and delivery. In some embodiments of the invention, a surfactant is useful for providing additional stability to the active ingredient(s), i.e. the anti-RSV antibody or antigen-binding fragment thereof.

Surfactants that may be useful in the formulations of the invention include, but are not limited to: nonionic surfactants such as polyoxyethylene sorbitan fatty acid esters (Polysorbates, sold under the trade name TWEEN (Uniquema Americas LLC, Wilmington, DE)) including Polysorbate-20 (polyoxyethylene sorbitan monolaurate), Polysorbate-40 (polyoxyethylene sorbitan monopalmitate), Polysorbate-60 (polyoxyethylene sorbitan monostearate), and Polysorbate-80 (polyoxyethylene sorbitan monooleate); polyoxyethylene alkyl ethers such as BRIJ 58 (Uniquema Americas LLC, Wilmington, DE) and BRIJ 35; poloxamers (e.g., poloxamer 188); TRITON X-100 (Union Carbide Corp., Houston, Tex.) and TRITON X-114; NP40; Span 20, Span 40, Span 60, Span 65, Span 80 and Span 85; copolymers of ethylene and propylene glycol (e.g., the PLURONIC series of nonionic surfactants such as PLURONIC F68, PLURONIC 10R5, PLURONIC F108, PLURONIC F127, PLURONIC F38, PLURONIC L44, PLURONIC L62 (BASF Corp., Ludwigshafen, Germany); and sodium dodecyl sulfate (SDS).

The amount of surfactant to be included in the formulations of the invention is an amount sufficient to perform the desired function, i.e. a minimal amount necessary to stabilize the active pharmaceutical ingredient (i.e. the anti-RSV antibody or antigen-binding fragment thereof) in the formulation. Typically, the surfactant is present in a concentration of from about 0.008% to about 0.1% w/v. In some embodiments of this aspect of the invention, the surfactant is present in the formulation in an amount from about 0.01% to about 0.04% w/v; from about 0.01% to about 0.03% w/v, from about 0.01% to about 0.02% w/v, from about 0.015% to about 0.04% w/v; from about 0.015% to about 0.03% w/v, from about 0.015% to about 0.02% w/v, from about 0.02% to about 0.04% w/v, from about 0.02% to about 0.035% w/v, or from about 0.02% to about 0.03% w/v. In specific embodiments, the surfactant is present in an amount of about 0.02% w/v. In alternative embodiments, the surfactant is present in an amount of about 0.01%, about 0.015%, about 0.025%, about 0.03%, about 0.035%, or about 0.04% w/v.

In exemplary embodiments of the invention, the surfactant is a nonionic surfactant selected from the group consisting of: Polysorbate 20, Polysorbate 80 and F127. In preferred embodiments, the surfactant is Polysorbate 80.

In specific embodiments, the anti-RSV antibody formulations comprise about 0.01% to about 0.04% w/v PS80. In further embodiments, the anti-RSV antibody formulations comprise PS80 in an amount of about 0.008%, about 0.01%, about 0.015%, about 0.02%, about 0.025%, about 0.03%, about 0.035%, about 0.04% or about 0.045% w/v. In particular embodiments, the anti-RSV antibody formulations comprise about 0.02% w/v PS80. In some embodiments, the anti-RSV antibody formulations comprise 0.01% to 0.04% w/v PS80. In some embodiments, the anti-RSV antibody formulations comprise PS80 in an amount of 0.008%, 0.01%, 0.015%, 0.02%, 0.025%, 0.03%, 0.035%, 0.04% or 0.045% w/v. In particular embodiments, the anti-RSV antibody formulations comprise 0.02% w/v PS80.

In specific embodiments, the anti-RSV antibody formulations of the invention comprise a chelator selected from DTPA and EDTA. In some embodiments, the chelator is DTPA. In further embodiments, the amount of DTPA is about 10 µM to about 90 µM, about 25 µM to about 75 µM, or about 50 µM. In some embodiments, the chelator is DTPA. In some embodiments, the amount of DTPA is 10 µM to 90 µM, 25 µM to 75 µM, or 50 µM.

In addition to an anti-RSV antibody or antigen-binding fragment thereof, embodiments of the formulation can contain a stabilizer, a buffer, an anti-oxidant, a surfactant, and a chelator, in the amounts/concentrations specified above.

The disclosure also provides an anti-RSV antibody formulation as described herein, wherein the formulation is contained in a glass vial or injection device (e.g. a syringe).

In further embodiments, the disclosure provides anti-RSV antibody formulations as described herein, wherein after storage of the formulation at 2-8° C. for 12 months, the percent of heavy chain and light chain measured by reducing CE-SDS is >96%.

In further embodiments, the disclosure provides anti-RSV antibody formulations as described herein, wherein after storage of the formulation at 2-8° C. for 12 months the percent of intact IgG in the formulation measured by non-reducing CE-SDS is >97%.

In further embodiments, the disclosure provides anti-RSV antibody formulations as described herein, wherein after storage of the formulation at 2-8° C. for 12 months, the percent of monomer as measured by HP-SEC is >98.5%.

In additional embodiments, the disclosure provides anti-RSV antibody formulations as described herein, wherein after storage of the formulation at 2-8° C. for 12 months, the percent of high molecular weight species as measured by HP-SEC is <1.5%.

In further embodiments, the disclosure provides anti-RSV antibody formulations as described herein, wherein after storage of the formulation at 25° C. for 12 months, the percent of monomer as measured by HP-SEC is >98.0%.

In additional embodiments, the disclosure provides anti-RSV antibody formulations as described herein, wherein after storage of the formulation at 25° C. for 6 months, the percent of high molecular weight species as measured by HP-SEC is <2%.

In further embodiments, the disclosure provides anti-RSV antibody formulations as described herein, wherein after storage of the formulation at 40° C. for 3 months, the percent of monomer as measured by HP-SEC is >94.0%, >94.5% or >95.0%.

In additional embodiments, the disclosure provides anti-RSV antibody formulations as described herein, wherein after storage of the formulation at 40° C. for 3 months, the percent of high molecular weight species as measured by HP-SEC is <5.5%, <5.0%, or <4.4%.

V. Specific Aspects and Embodiments of the Invention

In one aspect, the present disclosure provides an anti-RSV antibody formulation, comprising: a) about 50 mg/mL to about 250 mg/mL of an anti-RSV antibody, or antigen-binding fragment thereof; b) about 5 mM to about 20 mM buffer; c) a stabilizer selected from the group consisting of: (i) about 6% to about 8% weight/volume (w/v) non-reducing sugar; (ii) about 25 mM to about 75 mM of L-arginine, or a pharmaceutically acceptable salt of L-arginine; about 25 mM to about 75 mM L-proline, or a pharmaceutically acceptable salt of L-proline; about 25 mM to about 75 mM L-glutamate, or a pharmaceutically acceptable salt of L-glutamate; about 25 mM to about 75 mM L-lysine, or a pharmaceutically acceptable salt of L-lysine, or a mixture of such amino acids, and (iii) about 25 µM to 75 µM of a chelator; d) about 0.01% to about 0.10% of a non-ionic surfactant; and optionally e) about 1 mM to about 20 mM of an anti-oxidant.

In another aspect, the disclosure provides an anti-RSV antibody formulation, comprising: a) about 50 mg/mL to about 150 mg/mL of an anti-RSV antibody, or antigen-binding fragment thereof, b) about 5 mM to about 20 mM histidine; c) about 6% to about 8% weight/volume (w/v) sucrose; d) an excipient selected from about 25 mM to about 75 mM of L-arginine or a pharmaceutically acceptable salt of L-arginine, about 25 mM to about 75 mM L-lysine or a pharmaceutically acceptable salt of L-lysine, about 25 mM to about 75 mM of a mixture of L-arginine(HCl) and L-glutamate, and about 25 mM to about 75 mM of a mixture of L-arginine(HCl) and L-lysine(HCl); e) about 25 to 75 μM of DTPA; f) about 0.01% to about 0.10% polysorbate 80; and optionally g) about 1 mM to about 20 mM L-methionine.

In another aspect, the disclosure provides an anti-RSV antibody formulation, comprising: a) 100 mg/mL of an anti-RSV antibody, or antigen-binding fragment thereof, b) 10 mM histidine; c) 7% weight/volume (w/v) sucrose; d) an excipient selected from 50 mM L-arginine(HCl), 50 mM L-lysine(HCl), a mixture of 25 mM L-arginine and 25 mM L-glutamate, and a mixture of 25 mM L-arginine(HCl) and 25 mM L-lysine(HCl); e) 50 μM DTPA; f) 0.02% polysorbate 80; and optionally g) 1 mM to 20 mM L-methionine.

In another aspect, the disclosure provides an anti-RSV antibody formulation, comprising: a) 100 mg/mL of an anti-RSV antibody, or antigen-binding fragment thereof, b) 10 mM histidine; c) 7% weight/volume (w/v) sucrose; d) a mixture of 25 mM L-arginine(HCl) and 25 mM L-lysine (HCl); e) 50 μM DTPA; and f) 0.02% polysorbate 80.

In another aspect, the concentration of the anti-RSV antibody, or antigen-binding fragment thereof, is about 50 mg/mL to about 150 mg/mL. In another aspect, the concentration of the anti-RSV antibody, or antigen-binding fragment thereof, is about 75 mg/mL to about 125 mg/mL. In another aspect, the concentration of the anti-RSV antibody, or antigen-binding fragment thereof, is 50 mg/mL to 150 mg/mL. In another aspect, the concentration of the anti-RSV antibody, or antigen-binding fragment thereof, is 75 mg/mL to 125 mg/mL. In another aspect, the concentration of the anti-RSV antibody, or antigen-binding fragment thereof, is 100 mg/mL. In another aspect, the concentration of the anti-RSV antibody, or antigen-binding fragment thereof, is 75 mg/mL. In another aspect, the concentration of the anti-RSV antibody, or antigen-binding fragment thereof, is 50 mg/mL.

In another aspect, the formulation has a pH between about 5.5 and about 6.5. In another aspect, the formulation has a pH between 5.5 and 6.5. In another aspect, the formulation has a pH of 6.0.

In another aspect, the buffer is histidine. In another aspect, the concentration of histidine is from about 1 mM to about 20 mM. In another aspect, the concentration of histidine is from about 5 mM to about 15 mM. In another aspect, the concentration of histidine is 1 mM to 20 mM. In another aspect, the concentration of histidine is 5 mM to 15 mM. In another aspect, the concentration of histidine is 10 mM.

In another aspect, the instant formulation comprises a stabilizer selected from a non-reducing sugar; L-arginine, or a pharmaceutically acceptable salt of L-arginine; L-proline, or a pharmaceutically acceptable salt of L-proline; L-gluta-mate, or a pharmaceutically acceptable salt of L-glutamate; L-lysine, or a pharmaceutically acceptable salt of L-lysine; or a mixture of such amino acids. In another aspect, the instant formulation comprises an excipient selected from about 50 mM L-arginine(HCl), about 50 mM L-lysine(HCl), a mixture of about 25 mM L-arginine and about 25 mM L-glutamate, and a mixture of about 25 mM L-arginine(HCl) and about 25 mM L-lysine(HCl).

In another aspect, the instant formulation comprises a chelator which is DTPA at a concentration of about 25 μM to about 75 μM. In another aspect, the instant formulation comprises a chelator which is DTPA at a concentration of about 50 μM. In another aspect, the instant formulation comprises a chelator which is DTPA at a concentration of 50 μM.

In another aspect, the formulation comprises a non-ionic surfactant which is PS80 at a concentration of about 0.01% to about 0.10% w/v. In another aspect, the formulation comprises a non-ionic surfactant which is PS80 at a con-centration of about 0.02% w/v. In another aspect, the for-mulation comprises a non-ionic surfactant which is PS80 at a concentration of 0.02% w/v.

In another aspect, the formulation comprises an antioxi-dant which is L-methionine at a concentration of about 1 mM to about 20 mM. In another aspect, the formulation comprises an antioxidant which is L-methionine at a con-centration of about 10 mM. In another aspect, the formula-tion comprises an antioxidant which is L-methionine at a concentration of 10 mM.

In yet another aspect, the disclosure provides an anti-RSV antibody formulation comprising: a) about 50 mg/mL to about 250 mg/mL of an anti-RSV antibody, or antigen-binding fragment thereof; b) about 5 mM to about 20 mM histidine; c) about 4% to about 8% (w/v) sucrose; d) an excipient selected from the group consisting of about 25 mM to about 75 mM of L-arginine or a pharmaceutically accept-able salt of L-arginine, about 25 mM to about 75 mM of L-lysine or a pharmaceutically acceptable salt of L-lysine, a mixture of about 25 mM to about 75 mM L-arginine or a pharmaceutically acceptable salt of L-arginine and about 25 mM to about 75 mM L-glutamate or a pharmaceutically acceptable salt of L-glutamate, and a mixture of about 25 mM to about 75 mM of L-arginine or a pharmaceutically acceptable salt of L-arginine and about 25 mM to about 75 mM L-lysine or a pharmaceutically acceptable salt of L-ly-sine; and e) about 0.01% to about 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) about 25 mM to about 75 mM of L-arginine or a pharmaceutically acceptable salt of L-argi-nine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof, b) 5 mM to 20 mM histidine; c) 4% to 8% (w/v) sucrose; d) 25 mM to 75 mM of L-arginine or a pharmaceutically acceptable salt of L-arginine; and e) 0.01% to 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) about 25 mM to about 75 mM of L-lysine or a pharmaceutically acceptable salt of L-lysine; and e) about 0.01% to about 0.10% (w/v) polysorbate 80. In one embodiment, the anti-RSV antibody formulation com-prises: a) 50 mg/ml to 250 mg/ml of an anti-RSV antibody, or antigen-binding fragment thereof, b) 5 mM to 20 mM histidine; c) 4% to 8% (w/v) sucrose; d) 25 mM to 75 mM of L-lysine or a pharmaceutically acceptable salt of L-lysine; and e) 0.01% to 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) a mixture of about 25 mM to about 75 mM L-arginine or a pharmaceutically acceptable salt of L-arginine and about 25 mM to about 75 mM L-glutamate or a pharmaceutically acceptable salt of L-glutamate; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof; b) 5 mM to 20 mM histidine; c) 4% to about 8% (w/v) sucrose; d) a mixture of 25 mM to 75 mM L-arginine or a pharmaceutically acceptable salt of L-arginine and 25 mM to 75 mM L-glutamate or a pharmaceutically acceptable salt of L-glutamate; and e) 0.01% to 0.10% (w/v) polysorbate 80.

In one embodiment, the anti-RSV antibody formulation comprises: a) about 50 mg/ml to about 250 mg/ml of an anti-RSV antibody, or antigen-binding fragment thereof, b) about 5 mM to about 20 mM histidine; c) about 4% to about 8% (w/v) sucrose; d) a mixture of about 25 mM to about 75 mM of L-arginine or a pharmaceutically acceptable salt of L-arginine and about 25 mM to about 75 mM L-lysine or a pharmaceutically acceptable salt of L-lysine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof; b) 5 mM to 20 mM histidine; c) 4% to 8% (w/v) sucrose; d) a mixture of 25 mM to 75 mM of L-arginine or a pharmaceutically acceptable salt of L-arginine and 25 mM to 75 mM L-lysine or a pharmaceutically acceptable salt of L-lysine; and e) 0.01% to 0.10% (w/v) polysorbate 80.

In still another aspect, the disclosure provides an anti-RSV antibody formulation comprising: a) about 50 mg/mL to about 250 mg/mL of an anti-RSV antibody, or antigen-binding fragment thereof, b) about 5 mM to about 100 mM histidine; c) about 4% to about 8% (w/v) sucrose; and d) about 0.01% to about 0.10% (w/v) polysorbate 80. In one embodiment, the disclosure provides an anti-RSV antibody formulation comprising: a) 50 mg/mL to 250 mg/mL of an anti-RSV antibody, or antigen-binding fragment thereof, b) 5 mM to 100 mM histidine; c) 4% to 8% (w/v) sucrose; and d) 0.01% to 0.10% (w/v) polysorbate 80.

In one aspect, the anti-RSV antibody formulation comprises: a) about 50 mg/ml to about 250 mg/ml of an anti-RSV antibody, or antigen-binding fragment thereof, b) about 5 mM to about 100 mM histidine; c) about 4% to about 8% (w/v) sucrose; d) about 25 mM to about 75 mM of L-arginine or a pharmaceutically acceptable salt of L-arginine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof, b) 5 mM to 100 mM histidine; c) 4% to 8% (w/v) sucrose; d) 25 mM to 75 mM of L-arginine or a pharmaceutically acceptable salt of L-arginine; and e) 0.01% to 0.10% (w/v) polysorbate 80.

In one aspect, the anti-RSV antibody formulation comprises: a) about 50 mg/ml to about 250 mg/ml of an anti-RSV antibody, or antigen-binding fragment thereof, b) about 5 mM to about 100 mM histidine; c) about 4% to about 8% (w/v) sucrose; d) about 25 mM to about 75 mM of L-lysine or a pharmaceutically acceptable salt of L-lysine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof, b) 5 mM to 100 mM histidine; c) 4% to 8% (w/v) sucrose; d) 25 mM to 75 mM of L-lysine or a pharmaceutically acceptable salt of L-lysine; and e) 0.01% to 0.10% (w/v) polysorbate 80.

In one aspect, the anti-RSV antibody formulation comprises: a) about 50 mg/ml to about 250 mg/ml of an anti-RSV antibody, or antigen-binding fragment thereof, b) about 5 mM to about 100 mM histidine; c) about 4% to about 8% (w/v) sucrose; d) a mixture of about 25 mM to about 75 mM L-arginine or a pharmaceutically acceptable salt of L-arginine and about 25 mM to about 75 mM L-glutamate or a pharmaceutically acceptable salt of L-glutamate; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof, b) 5 mM to 100 mM histidine; c) 4% to about 8% (w/v) sucrose; d) a mixture of 25 mM to 75 mM L-arginine or a pharmaceutically acceptable salt of L-arginine and 25 mM to 75 mM L-glutamate or a pharmaceutically acceptable salt of L-glutamate; and e) 0.01% to 0.10% (w/v) polysorbate 80.

In one aspect, the anti-RSV antibody formulation comprises: a) about 50 mg/ml to about 250 mg/ml of an anti-RSV antibody, or antigen-binding fragment thereof, b) about 5 mM to about 100 mM histidine; c) about 4% to about 8% (w/v) sucrose; d) a mixture of about 25 mM to about 75 mM of L-arginine or a pharmaceutically acceptable salt of L-arginine and about 25 mM to about 75 mM L-lysine or a pharmaceutically acceptable salt of L-lysine; and e) about 0.01% to about 0.10% (w/v) polysorbate 80. In one embodiment, the anti-RSV antibody formulation comprises: a) 50 mg/ml to 250 mg/ml of an anti-RSV antibody, or antigen-binding fragment thereof, b) 5 mM to 100 mM histidine; c) 4% to 8% (w/v) sucrose; d) a mixture of 25 mM to 75 mM of L-arginine or a pharmaceutically acceptable salt of L-arginine and 25 mM to 75 mM L-lysine or a pharmaceutically acceptable salt of L-lysine; and e) 0.01% to 0.10% (w/v) polysorbate 80.

In certain embodiments of any of the foregoing aspects and embodiments, the histidine concentration is between about 70 mM and about 90 mM. In some embodiments, the histidine concentration is between 70 mM and 90 mM. In some embodiments, the histidine concentration is about 80 mM. In some embodiments, the histidine concentration is 80 mM.

In some embodiments of the above aspects and embodiments, the anti-RSV antibody formulation comprises about 125 mg/mL to about 175 mg/mL of the anti-RSV antibody, or antigen-binding fragment thereof. In one embodiment, the anti-RSV antibody formulation comprises 125 mg/mL to 175 mg/mL of the anti-RSV antibody, or antigen-binding fragment thereof. In one embodiment, the anti-RSV antibody formulation comprises about 150 mg/ml of the anti-RSV antibody, or antigen-binding fragment thereof. In one embodiment, the anti-RSV antibody formulation comprises 150 mg/ml of the anti-RSV antibody, or antigen-binding fragment thereof.

In some embodiments of the above aspects and embodiments, the anti-RSV antibody formulation comprises about 150 mg/mL to about 200 mg/mL of the anti-RSV antibody, or antigen-binding fragment thereof. In some embodiments, the anti-RSV antibody formulation comprises 150 mg/mL to 200 mg/mL of the anti-RSV antibody, or antigen-binding fragment thereof. In some embodiments, the anti-RSV antibody formulation comprises about 175 mg/ml of the anti-RSV antibody, or antigen-binding fragment thereof. In some embodiments, the anti-RSV antibody formulation comprises 175 mg/ml of the anti-RSV antibody, or antigen-binding fragment thereof.

In some embodiments of the above aspects and embodiments, the anti-RSV antibody formulation comprises about 175 mg/mL to about 225 mg/mL of the anti-RSV antibody, or antigen-binding fragment thereof. In some embodiments, the anti-RSV antibody formulation comprises 175 mg/mL to 225 mg/mL of the anti-RSV antibody, or antigen-binding fragment thereof. In some embodiments, the anti-RSV antibody formulation comprises about 200 mg/ml of the anti-RSV antibody, or antigen-binding fragment thereof. In some embodiments, the anti-RSV antibody formulation comprises 200 mg/ml of the anti-RSV antibody, or antigen-binding fragment thereof.

In some embodiments of the above aspects and embodiments, the anti-RSV antibody formulation further comprises about 25 to about 75 µM diethylenetriaamine pentaacetate (DTPA). In some embodiments, the anti-RSV antibody formulation further comprises 25 to 75 µM diethylenetriamine pentaacetate (DTPA).

In some embodiments of the above aspects and embodiments, the anti-RSV antibody formulation further comprises about 1 mM to about 20 mM L-methionine. In some embodiments, the anti-RSV antibody formulation further comprises 1 mM to 20 mM L-methionine.

In some embodiments, the pH of the anti-RSV antibody formulation is 5.5 to 6.5. In some embodiments, the pH of the anti-RSV antibody formulation is about 6.0. In some embodiments, the pH of the anti-RSV antibody formulation is 6.0.

In some embodiments, the anti-RSV antibody comprises CDRs having the amino acid sequences of SEQ ID NOs: 1-6. In some embodiments, the anti-RSV antibody comprises a heavy chain variable region having the amino acid sequence of SEQ ID NO: 7 and a light chain variable region having the amino acid sequence of SEQ ID NO: 8. In some embodiments, the anti-RSV antibody comprises a heavy chain immunoglobulin consisting of the amino acid sequence set forth in SEQ ID NO: 9 and a light chain immunoglobulin consisting of the amino acid sequence set forth in SEQ ID NO: 10.

In one aspect, the disclosure provides a method of treating or preventing RSV infection in a human patient in need thereof comprising: administering an effective amount of the anti-RSV antibody formulation of any one of the above aspects and embodiments to the patient.

In some embodiments of the foregoing method, the effective amount of the anti-RSV antibody formulation comprises a fixed dose of anti-RSV antibody or antigen-binding fragment thereof, of about 10 mg to about 150 mg. In some embodiments, the effective amount of the anti-RSV antibody formulation comprises a fixed dose of anti-RSV antibody or antigen-binding fragment thereof of 10 mg to 150 mg. In some embodiments, the effective amount of the anti-RSV antibody formulation comprises a fixed dose of anti-RSV antibody or antigen-binding fragment thereof between about 25 mg and about 125 mg. In some embodiments, the effective amount of the anti-RSV antibody formulation comprises a fixed dose of anti-RSV antibody or antigen-binding fragment thereof between 25 mg and 125 mg. In some embodiments, the effective amount of the anti-RSV antibody formulation comprises a fixed dose of anti-RSV antibody or antigen-binding fragment thereof between about 50 mg and about 100 mg. In some embodiments, the effective amount of the anti-RSV antibody formulation comprises a fixed dose of anti-RSV antibody or antigen-binding fragment thereof between 50 mg and 100 mg. In some embodiments, the effective amount of the anti-RSV antibody formulation comprises a fixed dose of anti-RSV antibody or antigen-binding fragment thereof of about 100 mg. In some embodiments, the effective amount of the anti-RSV antibody formulation comprises a fixed dose of anti-RSV antibody or antigen-binding fragment thereof of about 100 mg.

In some embodiments of the foregoing method, the anti-RSV antibody formulation is administered by intramuscular administration.

In some embodiments, the disclosure provides an anti-RSV antibody formulation of any one of the foregoing aspects or embodiments for use in a method for treating or preventing RSV infection in a human patient.

In some embodiments, the disclosure provides for use of the anti-RSV antibody formulation of any one of the foregoing aspects or embodiments in the manufacture of a medicament for treating or preventing RSV infection in a human patient.

In some embodiments of the invention, any of the formulations described herein is in an aqueous solution. In alternative embodiments, the invention provides lyophilized formulations made by lyophilizing an aqueous formulation to provide a reconstituted formulation of the invention, as discussed more fully, infra.

VI. Lyophilized Pharmaceutical Compositions

Lyophilized formulations of therapeutic proteins (e.g., anti-RSV antibody, or an antigen-binding fragment thereof) provide several advantages. Lyophilized formulations in general offer better chemical stability than solution formulations, and thus increased half-life. A lyophilized formulation may also be reconstituted at different concentrations depending on clinical factors, such as route of administration or dosing. For example, a lyophilized formulation may be reconstituted at a high concentration (i.e. in a small volume) if necessary for subcutaneous administration, or at a lower concentration if administered intravenously. High concentrations may also be necessary if high dosing is required for a particular subject, particularly if administered subcutaneously where injection volume must be minimized. One such lyophilized antibody formulation is disclosed at U.S. Pat. No. 6,267,958, which is hereby incorporated by reference in its entirety. Lyophilized formulations of another therapeutic protein are disclosed at U.S. Pat. No. 7,247,707, which is hereby incorporated by reference in its entirety.

Typically, the lyophilized formulation is prepared in anticipation of reconstitution at high concentration of drug product (DP, in an exemplary embodiment an anti-RSV antibody, or antigen-binding fragment thereof), i.e. in anticipation of reconstitution in a low volume of water. Subsequent dilution with water or isotonic buffer can then readily be used to dilute the DP to a lower concentration. Typically, excipients are included in a lyophilized formulation of the invention at levels that will result in a roughly isotonic formulation when reconstituted at high DP concentration, e.g. for subcutaneous administration. Reconstitution in a larger volume of water to give a lower DP concentration will necessarily reduce the tonicity of the reconstituted solution, but such reduction may be of little significance in non-subcutaneous, e.g. intravenous, administration. If isotonicity is desired at lower DP concentration, the lyophilized powder may be reconstituted in the standard low volume of water and then further diluted with isotonic diluent, such as 0.9% sodium chloride.

In an embodiment of the invention, an anti-RSV antibody (or antigen-binding fragment thereof) is formulated as a lyophilized powder for reconstituting and utilizing for intravenous, subcutaneous, or intramuscular administration. In certain embodiments, the antibody (or antigen-binding fragment thereof) is provided at about 50 mg/vial, and is reconstituted with sterile water for injection prior to use. If desired, the reconstituted antibody may be aseptically diluted with 0.9% sodium chloride Injection USP in a sterile IV container. In some embodiments, the target pH of the reconstituted formulation is 5.5±0.5. In various embodiments, the lyophilized formulation of the invention enables reconstitution of the anti-RSV antibody to high concentrations, such as about 20, 25, 30, 40, 50, 60, 75, 100, 125, 150, 175 or more mg/mL.

Lyophilized formulations are by definition essentially dry, and thus the concept of concentration is not useful in describing them. Describing a lyophilized formulation in the terms of the weight of the components in a unit dose vial is more useful, but is problematic because it varies for different doses or vial sizes. In describing the lyophilized formulations of the invention, it is useful to express the amount of a component as the ratio of the weight of the component compared to the weight of the drug substance (DS) in the same sample (e.g. a vial). This ratio may be expressed as a percentage. Such ratios reflect an intrinsic property of the lyophilized formulations of the invention, independent of vial size, dosing, and reconstitution protocol.

In other embodiments, the lyophilized formulation of anti-RSV antibody, or antigen-binding fragment, is defined in terms of the pre-lyophilization solution used to make the lyophilized formulation, such as the pre-lyophilization solution. In one embodiment the pre-lyophilization solution comprises antibody, or antigen-binding fragment thereof, at a concentration of about 10 mg/mL, about 25 mg/mL, or about 50 mg/mL. Such pre-lyophilization solutions may be at pH 4.4-5.2 (including about 4.4, 4.5, 4.6, 4.7, 4.8, 4.9, 5.0, 5.1. and 5.2), e.g. preferably about pH 4.8, or about pH 5.5.

In yet other embodiments, the lyophilized formulation of anti-RSV antibody, or antigen-binding fragment, is defined in terms of the reconstituted solution generated from the lyophilized formulation.

Reconstituted solutions may comprise antibody, or antigen-binding fragment thereof, at concentrations of about 50, 60, 75, 80, 90 or 100 mg/mL or higher concentrations such as 150 mg/mL, 167 mg/mL, 200 mg/mL, or up to about 250 mg/mL. Such reconstituted solutions may be at about pH 5.5, or range from about pH 5.0 to 6.0.

The lyophilized formulations of the invention are formed by lyophilization (freeze-drying) of a pre-lyophilization solution. Freeze-drying is accomplished by freezing the formulation and subsequently subliming water at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will dictate the time required for drying, which can range from a few hours to several days (e.g. 40-60 hrs). A secondary drying stage may be carried out at about 0-40° C., depending primarily on the type and size of container and the type of protein employed. The secondary drying time is dictated by the desired residual moisture level in the product and typically takes at least about 5 hours. Typically, the moisture content of a lyophilized formulation is less than about 5%, and preferably less than about 3%. The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial.

The lyophilized formulations of the invention are reconstituted prior to administration. The protein may be reconstituted at a concentration of about 10, 15, 20, 25, 30, 40, 50, 60, 75, 80, 90 or 100 mg/mL or higher concentrations such as 150 mg/mL, 200 mg/mL, 250 mg/mL, or 300 mg/mL up to about 500 mg/mL. High protein concentrations are particularly useful where subcutaneous delivery of the reconstituted formulation is intended. However, for other routes of administration, such as intravenous administration, lower concentrations of the protein may be desired (e.g. from about 5-50 mg/mL).

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution.

The disclosure provides a liquid anti-RSV antibody formulation that is reconstituted from a lyophilized formulation wherein the reconstituted solution comprises: a) about 50 mg/mL to about 150 mg/mL of an anti-RSV antibody, or antigen-binding fragment thereof, b) about 5 mM to about 20 mM histidine; c) about 6% to about 8% weight/volume (w/v) sucrose; d) an excipient selected from about 25 mM to about 75 mM of L-arginine or a pharmaceutically acceptable salt of L-arginine, about 25 mM to about 75 mM of L-proline or a pharmaceutically acceptable salt of L-proline, about 25 mM to about 75 mM of L-glutamate or a pharmaceutically acceptable salt of L-glutamate, about 25 mM to about 75 mM L-lysine or a pharmaceutically acceptable salt of L-lysine, about 25 mM to about 75 mM of a mixture of L-arginine and L-glutamate, and about 25 mM to about 75 mM of a mixture of L-arginine(HCl) and L-lysine(HCl); e) about 25 µM to 75 M DTPA; f) about 0.01% to about 0.10% polysorbate 80; and optionally g) about 1 mM to about 20 mM L-methionine.

The disclosure provides a liquid anti-RSV antibody formulation that is reconstituted from a lyophilized formulation wherein the reconstituted solution comprises: a) 100 mg/mL of an anti-RSV antibody, or antigen-binding fragment thereof, b) 10 mM histidine; c) 7% weight/volume (w/v) sucrose; d) an excipient selected from 50 mM L-arginine (HCl), 50 mM L-lysine(HCl), a mixture of 25 mM L-arginine and 25 mM L-glutamate, and a mixture of 25 mM L-arginine(HCl) and 25 mM L-lysine(HCl); e) 50 µM DTPA; f) 0.02% polysorbate 80; and optionally g) 1 mM to 20 mM L-methionine.

The disclosure provides a liquid anti-RSV antibody formulation that is reconstituted from a lyophilized formulation wherein the reconstituted solution comprises: a) 100 mg/mL of an anti-RSV antibody, or antigen-binding fragment thereof, b) 10 mM histidine; c) 7% weight/volume (w/v) sucrose; d) a mixture of 25 mM L-arginine(HCl) and 25 mM L-lysine(HCl); e) 50 µM DTPA; and f) 0.02% polysorbate 80.

The disclosure also provides a liquid anti-RSV antibody formulation that is reconstituted from a lyophilized formulation wherein the reconstituted solution comprises: a) about 50 mg/mL to about 250 mg/mL of an anti-RSV antibody, or antigen-binding fragment thereof, b) about 5 mM to about 20 mM histidine; c) about 4% to about 8% (w/v) sucrose; d) an excipient selected from the group consisting of about 25 mM to about 75 mM of L-arginine or a pharmaceutically acceptable salt of L-arginine, about 25 mM to about 75 mM of L-lysine or a pharmaceutically acceptable salt of L-lysine, a mixture of about 25 mM to about 75 mM L-arginine or a pharmaceutically acceptable salt of L-arginine and about 25 mM to about 75 mM L-glutamate or a pharmaceutically acceptable salt of L-glutamate, and a mixture of about 25 mM to about 75 mM of L-arginine or a pharmaceutically acceptable salt of L-arginine and about 25 mM to about 75 mM L-lysine or a pharmaceutically acceptable salt of L-lysine; and e) about 0.01% to about 0.10% (w/v) polysorbate 80.

VII. Liquid Pharmaceutical Compositions

A liquid antibody formulation can be made by taking the drug substance (e.g., anti-RSV antibody) which is in liquid form and buffer exchanging it into the desired buffer as the last step of the purification process. There is no lyophilization step in this embodiment. The drug substance in the final buffer is concentrated to a desired concentration. Excipients such as sucrose, methionine and polysorbate 80 are added to the drug substance and it is diluted using the appropriate buffer to final protein concentration. The final formulated drug substance is filtered, e.g. using 0.22 m filters, and filled into a final container (e.g. glass vials or syringes). Such a liquid formulation is exemplified by a final liquid formulation comprising a) 100 mg/mL of an anti-RSV antibody, or antigen-binding fragment thereof; b) 10 mM histidine; c) 7% weight/volume (w/v) sucrose; d) a mixture of 25 mM L-arginine(HCl) and 25 mM L-lysine(HCl); e) 50 μM DTPA; and f) 0.02% polysorbate 80.

VIII. Methods of Use

The invention also relates to a method of preventing or treating RSV infection in a subject, the method comprising administering an effective amount of any of the formulations of the invention; i.e., any formulation described herein, to the subject. In some embodiments of this method, the formulation is administered to the subject via intravenous administration. In other embodiments, the formulation is administered to the subject via subcutaneous administration. In other embodiments, the formulation is administered via intramuscular administration.

In a specific embodiment, a mammal, preferably a human, is administered a prophylactic, therapeutic or pharmaceutical formulation of the present invention for the treatment, prevention or amelioration of one or more symptoms associated with a RSV infection in an amount effective for decreasing RSV titers. In accordance with this embodiment, an effective amount of an anti-RSV antibody or antibody fragment reduces the RSV titers in the lung as measured, for example, by the concentration of RSV in sputum samples or a lavage from the lungs from a mammal. In another embodiment, a mammal, preferably a human, is administered a prophylactic, therapeutic or pharmaceutical formulation comprising an anti-RSV antibody of the present invention or fragments thereof for the treatment, prevention or amelioration of symptoms associated with a RSV infection in an amount effective for neutralizing RSV and/or blocking RSV infection in the mammal.

The formulations of the instant invention can also be used immunotherapeutically for RSV disease in both humans and other animals. The term, "immunotherapeutically" or "immunotherapy" as used herein in conjunction with the anti-RSV antibody or antigen-binding fragments thereof of the invention denotes both prophylactic as well as therapeutic administration and both passive immunization with substantially purified polypeptide products, as well as gene therapy by transfer of polynucleotide sequences encoding the product or part thereof. Passive immunization includes transfer of active humoral immunity or providing antibodies to a subject in need thereof. Accordingly, in certain embodiments of the invention, the present invention provides methods for transfer of active humoral immunity and methods of providing RSV antibodies or antigen-binding fragments thereof, such as IgG antibodies, to a patient at risk of RSV infection. Thus, the monoclonal antibodies or antigen-binding fragments thereof can be administered to high-risk subjects in order to lessen the likelihood and/or severity of RSV disease or administered to subjects already evidencing active RSV infection.

The present invention also provides a method for modulating or treating at least one adult or pediatric RSV related disease, in a cell, tissue, organ, animal, or patient including, but not limited to, lower respiratory infections, pneumonia, tracheobronchitis, bronchiolitis, bronchitis, and any related infections or inflammatory disorders, such as but not limited to at least one of, or at least one inflammation related to, systemic inflammatory response syndrome, sepsis syndrome, gram positive sepsis, gram negative sepsis, culture negative sepsis, fungal sepsis, neutropenic fever, urosepsis, meningococcemia, adult respiratory distress syndrome, allergic rhinitis, perennial rhinitis, asthma, systemic anaphylaxis, receptor hypersensitivity reactions, chronic obstructive pulmonary disease (COPD), hypersensitivity pneumonitis, granulomas due to intracellular organisms, drug sensitivity, cachexia, cystic fibrosis, neonatal chronic lung disease; at least one infectious disease in a cell, tissue, organ, animal or patient, including, but not limited to, at least one of: acute or chronic bacterial infection, acute and chronic parasitic or infectious processes, including bacterial, viral and fungal infections, HIV infection, HIV neuropathy, meningitis, hepatitis (A, B or C, or the like), septic arthritis, peritonitis, pneumonia, epiglottitis, *E. coli* 0157:h7, hemolytic uremic syndrome, thrombolytic thrombocytopenic purpura, malaria, dengue hemorrhagic fever, leishmaniasis, leprosy, toxic shock syndrome, streptococcal myositis, gas gangrene, Mycobacterium tuberculosis, Mycobacterium avium intracellulare, Pneumocystis carinii pneumonia, pelvic inflammatory disease, orchitis, epididymitis, legionella, lyme disease, influenza A, Epstein-Barr virus, vital-associated hemophagocytic syndrome, vital encephalitis, aseptic meningitis, and the like. Such a method can optionally comprise administering an effective amount of a composition or pharmaceutical composition comprising at least one RSV antibody or antigenic fragment thereof to a cell, tissue, organ, animal or patient in need of such modulation, treatment or therapy.

In one embodiment, prophylactic, therapeutic or pharmaceutical formulation comprising an anti-RSV antibody of the invention or fragments thereof are administered to a mammal, preferably a human, to treat, prevent or ameliorate one or more symptoms associated with RSV infection. In another embodiment, prophylactic, therapeutic or pharmaceutical formulations comprising an anti-RSV antibody of the invention or fragments thereof are administered to a human with cystic fibrosis, bronchopulmonary dysplasia, congenital heart disease, congenital immunodeficiency or acquired immunodeficiency, or to a human who has had a transplant (e.g., bone marrow, lung, or hematopoietic stem cell transplantation (HSCT)) to treat, prevent or ameliorate one or more symptoms associated with RSV infection.

In another embodiment, prophylactic, therapeutic or pharmaceutical formulations comprising an anti-RSV antibody of the invention or fragments thereof are administered to a human infant, preferably a human infant born prematurely or a human infant at risk of hospitalization for RSV infection to treat, prevent or ameliorate one or more symptoms associated with RSV infection. In yet another embodiment, prophylactic, therapeutic or pharmaceutical formulations of the instant invention are administered to the elderly or people in group homes (e.g., nursing homes or rehabilitation centers) or immunocompromised individuals.

In another embodiment, the present invention provides a method of preventing respiratory infection caused by RSV. In another embodiment, the present invention provides a method of preventing lower respiratory infection caused by RSV. In another embodiment, the present invention provides a method of preventing lower respiratory infection caused by RSV A and B strains. In another embodiment, the present invention provides a method of preventing medically attended lower respiratory infection caused by RSV A and B strains in infants born >29 weeks of gestation and <8 months of age at time of dosing. In another embodiment, the present invention provides a method of preventing lower respiratory tract infection caused by RSV in all infants entering their first RSV season and children with chronic lung disease or congenital heart disease entering their first and second RSV season.

IX. General Methods

Standard methods in molecular biology are described Sambrook, Fritsch and Maniatis (1982 & 1989 2$^{nd}$ Edition, 2001 3d Edition) *Molecular Cloning, A Laboratory Manual*, Cold Spring Harbor Laboratory Press, Cold Spring Harbor, N.Y.; Sambrook and Russell (2001)*Molecular Cloning, 3$^{rd}$ ed., Cold Spring Harbor Laboratory Press, Cold Spring Harbor, NY; Wu (1993) *Recombinant DNA*, Vol. 217, Academic Press, San Diego, CA). Standard methods also appear in Ausubel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001)*Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, NY; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, NY, pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272: 10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, New York; Kay et al. (1996) *Phage Display of Peptides and Proteins: A Laboratory Manual*, Academic Press, San Diego, CA; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, NJ; Givan (2001) *Flow Cytometry, 2$^{nd}$ ed.; Wiley-Liss, Hoboken, NJ; Shapiro (2003) *Practical Flow Cytometry*, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, OR; Sigma-Aldrich (2003) *Catalogue*, St. Louis, MO).

Standard methods of histology of the immune system are described (see, e.g., Muller-Harmelink (ed.) (1986) *Human Thymus: Histopathology and Pathology*, Springer Verlag, New York, NY; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, NY).

Software packages and databases for determining, e.g., antigenic fragments, leader sequences, protein folding, functional domains, glycosylation sites, and sequence alignments, are available (see, e.g., GenBank, Vector NTI Suite (Informax, Inc, Bethesda, MD); GCG Wisconsin Package (Accelrys, Inc., San Diego, CA); DECYPHER (TimeLogic Corp., Crystal Bay, Nevada); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

X. Analytical Methods

Analytical methods suitable for evaluating the product stability include size exclusion chromatography (SEC), dynamic light scattering test (DLS), differential scanning calorimetery (DSC), iso-asp quantification, potency, UV at 340 nm, UV spectroscopy, and FTIR. SEC (J. Pharm. Scien., 83:1645-1650, (1994); Pharm. Res., 11:485 (1994); J. Pharm. Bio. Anal., 15:1928 (1997); J. Pharm. Bio. Anal., 14:1133-1140 (1986)) measures percent monomer in the product and gives information of the amount of soluble aggregates. DSC (Pharm. Res., 15:200 (1998); Pharm. Res., 9:109 (1982)) gives information of protein denaturation temperature and glass transition temperature. DLS (American Lab., November (1991)) measures mean diffusion coefficient, and gives information of the amount of soluble and insoluble aggregates. UV at 340 nm measures scattered light intensity at 340 nm and gives information about the amounts of soluble and insoluble aggregates. UV spectroscopy measures absorbance at 278 nm and gives information of protein concentration. FTIR (Eur. J. Pharm. Biopharm., 45:231 (1998); Pharm. Res., 12:1250 (1995); J. Pharm. Scien., 85:1290 (1996); J. Pharm. Scien., 87:1069 (1998)) measures IR spectrum in the amide one region, and gives information of protein secondary structure.

The iso-asp content in the samples is measured using the Isoquant Isoaspartate Detection System (Promega). The kit uses the enzyme Protein Isoaspartyl Methyltransferase (PIMT) to specifically detect the presence of isoaspartic acid residues in a target protein. PIMT catalyzes the transfer of a methyl group from S-adenosyl-L-methionine to isoaspartic acid at the .alpha.-carboxyl position, generating S-adenosyl-L-homocysteine (SAH) in the process. This is a relatively small molecule, and can usually be isolated and quantitated by reverse phase HPLC using the SAH HPLC standards provided in the kit.

The potency or bioidentity of an antibody can be measured by its ability to bind to its antigen. The specific binding of an antibody to its antigen can be quantitated by any method known to those skilled in the art, for example, an immunoassay, such as ELISA (enzyme-linked immunosorbant assay).

All publications mentioned herein are incorporated by reference for the purpose of describing and disclosing methodologies and materials that might be used in connection with the invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

Anti-RSV Antibody Formulation Stability at Different pH

This study was performed with a 100 mg/mL anti-RSV antibody concentration in 10 mM histidine buffer. Seven % (w/v) sucrose was added to the formulation to increase the bulk stability (as stabilizer and nonionic tonicity modifier) of the molecule. Briefly, the drug substance (DS) was formulated at 100 mg/mL in 10 mM histidine, 7% sucrose at pH 5.5, pH 6.0 and pH 6.5. Formulated DS was filled into vials and staged on stability at 5° C. (ambient humidity), 25° C. (60% relative humidity), and 40° C. (75% relative humidity) for three months protected from light.

Samples were assessed by size exclusion chromatography (SEC) for purity in which the percentage of monomer was determined, as well as the percentages of high molecular weight species (HMW) and late eluting peaks (LMW species). Ultra Performance—Size Exclusion Chromatography (UP-SEC) was performed by diluting the samples (anti-RSV antibody) to 1.0 mg/mL in mobile phase (100 mM sodium phosphate and 100 mM sodium chloride, pH 7.0); flow rate of 0.5 mL/min. The diluted samples were injected (5 μL) into a UPLC equipped with a Waters BEH200 column and a UV detector. Proteins in the sample were separated by size and detected by UV absorption at 214 nm.

This study was conducted to study the effect of pH on stability of an anti-RSV antibody formulation. Based on the results from the thermal stability study for up to 3 months, there was no measurable difference between the stability of 100 mg/mL formulations at pH 5.5, 6.0, and 6.5 for any of the conditions. No change was noticed in UP-SEC % Monomer levels at 5° C.; however, a slight drop (~2%) was noticed at 25° C. and a more significant drop (~20%) at 40° C. Based on the results, a pH of 6.0 was selected for further development (see Table 1).

TABLE 1

| Formulation Number | Description | | | | |
|---|---|---|---|---|---|
| A1 | Anti-RSV antibody (100 mg/mL) | 10 mM Histidine | 7% Sucrose (w/v) | 0.02% PS80 (w/v) | pH = 5.5 |
| A2 | Anti-RSV antibody (100 mg/mL) | 10 mM Histidine | 7% Sucrose (w/v) | 0.02% PS80 (w/v) | pH = 6.0 |
| A3 | Anti-RSV antibody (100 mg/mL) | 10 mM Histidine | 7% Sucrose (w/v) | 0.02% PS80 (w/v) | pH = 6.5 |

31 | 32

Example 2

Anti-RSV Antibody Formulation Excipient (Amino Acids and Mixtures Thereof) Screening (to Reduce Aggregation)

This study compared the stability of an anti-RSV antibody in 10 mM histidine (pH=6), 0.02% PS80, 7% sucrose in the presence of (i) 50 mM L-Arg·HCl or (ii) 50 mM L-Lys·HCl or (iii) mixture of 25 mM L-Arg and 25 mM L-Glu or (iv) mixture of 25 mM L-Arg·HCl and 25 mM L-Lys·HCl.

These four excipients were tested to reduce aggregation, improve chemical stability (see Example 3) and reduce viscosity (see Example 4). The four tested excipients were:

(i) 50 mM L-Arg·HCl;
(ii) 50 mM L-Lys·HCl;
(iii) a mixture of 25 mM L-Arg and 25 mM L-Glu; and
(iv) a mixture of 25 mM L-Arg·HCl and 25 mM L-Lys·HCl.

The first two excipients were examined to understand the effects of the positively charged lysine and arginine in the presence of the chloride counteranion. The third excipient was tested to understand the effect of arginine in the presence of another counteranion (glutamate). The fourth excipient was a mixture of the first two excipients to determine if the two excipients can play a complementary role. It was hypothesized that this mixture may play a better role than the individual excipients, as the mixture of excipients have different pKa and differentially shield the surface change distribution of the mAb, thereby increasing repulsive interactions, which in turn would reduce aggregation and viscosity.

To evaluate the stability of the formulations, the five formulations were filled into vials and staged on stability at 5° C. (ambient humidity), 25° C. (60% relative humidity), and 40° C. (75% relative humidity) for eight weeks protected from light. The five formulations are listed in Table 2 below.

TABLE 2

| Formulation Number | Description | | | | |
|---|---|---|---|---|---|
| 1 | Anti-RSV antibody (100 mg/mL) | 10 mM Histidine (pH = 6) | 7% Sucrose (w/v) | 0.02% PS80 (w/v) | N/A |
| 2 | Anti-RSV antibody (100 mg/mL) | 10 mM Histidine (pH = 6) | 7% Sucrose (w/v) | 0.02% PS80 (w/v) | 50 mM L-Arg•HCl |
| 3 | Anti-RSV antibody (100 mg/mL) | 10 mM Histidine (pH = 6) | 7% Sucrose (w/v) | 0.02% PS80 (w/v) | 50 mM L-Lys•HCl |
| 4 | Anti-RSV antibody (100 mg/mL) | 10 mM Histidine (pH = 6) | 7% Sucrose (w/v) | 0.02% PS80 (w/v) | Mixture of 25 mM L-Arg and 25 mM L-Glu |
| 5 | Anti-RSV antibody (100 mg/mL) | 10 mM Histidine (pH = 6) | 7% Sucrose (w/v) | 0.02% PS80 (w/v) | Mixture of 25 mM L-Arg•HCl and 25 mM L-Lys•HCl |

Samples were assessed by size exclusion chromatography (SEC) for purity in which the percentage of monomer was determined, as well as the percentages of high molecular weight species (HMW) and late eluting peaks (LMW species). Ultra Performance—Size Exclusion Chromatography (UP-SEC) was performed by diluting the samples to 1.0 mg/mL (anti-RSV antibody) in mobile phase (100 mM sodium phosphate and 100 mM sodium chloride, pH 7.0); flow rate of 0.5 mL/min. The diluted samples were injected (5 μL) into a UPLC equipped with a Waters BEH200 column and a UV detector. Proteins in the sample were separated by size and detected by UV absorption at 214 nm.

The UPSEC data to evaluate the levels of High Molecular Weight Species (HMW or aggregates), % monomer and Low Molecular Weight (LMW) species is shown in the Table 3. [T0=Time 0; 4 W=4 Weeks; and 8 W=8 Weeks]

TABLE 3

| | Peak | | |
|---|---|---|---|
| Sample Name | HMW | Monomer | LMW |
| Anti-RSV Antibody DP control T0 5° C. | 1.77 | 98.1 | 0.09 |
| Anti-RSV Antibody DP control T0 4W5° C. | 1.88 | 98.0 | 0.11 |
| Anti-RSV Antibody DP control T0 4W25° C. | 2.86 | 96.9 | 0.21 |
| Anti-RSV Antibody DP control T0 4W40° C. | 4.05 | 93.2 | 2.77 |
| Anti-RSV Antibody DP control T0 8W5° C. | 2.00 | 97.9 | 0.13 |
| Anti-RSV Antibody DP control T0 8W25° C. | 3.13 | 96.6 | 0.28 |
| Anti-RSV Antibody DP control T0 8W40° C. | 4.83 | 91.1 | 4.05 |
| Anti-RSV Antibody DP + L-Arg•HCl T05° C. | 1.55 | 98.3 | 0.14 |

TABLE 3-continued

| | Peak | | |
|---|---|---|---|
| Sample Name | HMW | Monomer | LMW |
| Anti-RSV Antibody DP + L-Arg•HCl 4W5° C. | 1.54 | 98.3 | 0.12 |
| Anti-RSV Antibody DP + L-Arg•HCl 4W25° C. | 2.06 | 97.8 | 0.18 |
| Anti-RSV Antibody DP + L-Arg•HCl 4W40° C. | 2.72 | 95.4 | 1.90 |
| Anti-RSV Antibody DP + L-Arg•HCl 8W5° C. | 1.66 | 98.2 | 0.13 |
| Anti-RSV Antibody DP + L-Arg•HCl 8W25° C. | 2.34 | 97.4 | 0.28 |
| Anti-RSV Antibody DP + L-Arg•HCl 8W40° C. | 3.46 | 93.1 | 3.41 |
| Anti-RSV Antibody DP + L-Lys•HCl T05° C. | 1.58 | 98.3 | 0.12 |
| Anti-RSV Antibody DP + L-Lys•HCl 4W5° C. | 1.79 | 98.1 | 0.12 |
| Anti-RSV Antibody DP + L-Lys•HCl 4W25° C. | 2.17 | 97.6 | 0.20 |
| Anti-RSV Antibody DP + L-Lys•HCl 4W40° C. | 3.01 | 95.1 | 1.87 |
| Anti-RSV Antibody DP + L-Lys•HCl 8W5° C. | 1.71 | 98.2 | 0.13 |
| Anti-RSV Antibody DP + L-Lys•HCl 8W25° C. | 2.51 | 97.2 | 0.27 |
| Anti-RSV Antibody DP + L-Lys•HCl 8W40° C. | 3.94 | 92.5 | 3.58 |
| Anti-RSV Antibody DP + L-Arg•L-Glu T05° C. | 1.80 | 98.1 | 0.10 |
| Anti-RSV Antibody DP + L-Arg•L-Glu 4W5° C. | 1.87 | 98.0 | 0.12 |
| Anti-RSV Antibody DP + L-Arg•L-Glu 4W25° C. | 2.49 | 97.3 | 0.22 |
| Anti-RSV Antibody DP + L-Arg•L-Glu 4W40° C. | 3.77 | 93.4 | 2.83 |
| Anti-RSV Antibody DP + L-Arg•L-Glu 8W5° C. | 1.90 | 98.0 | 0.13 |
| Anti-RSV Antibody DP + L-Arg•L-Glu 8W25° C. | 2.68 | 97.0 | 0.31 |
| Anti-RSV Antibody DP + L-Arg•L-Glu 8W40° C. | 4.40 | 91.8 | 3.80 |
| Anti-RSV Antibody DP + L-Arg•HCl + L-Lys•HCl T05° C. | 1.67 | 98.2 | 0.10 |
| Anti-RSV Antibody DP + L-Arg•HCl + L-Lys•HCl 4W5° C. | 2.22 | 97.6 | 0.20 |
| Anti-RSV Antibody DP + L-Arg•HCl + L-Lys•HCl 4W25° C. | 1.79 | 98.1 | 0.12 |
| Anti-RSV Antibody DP + L-Arg•HCl + L-Lys•HCl 4W40° C. | 3.03 | 94.8 | 2.19 |
| Anti-RSV Antibody DP + L-Arg•HCl + L-Lys•HCl 8W5° C. | 1.71 | 98.2 | 0.13 |
| Anti-RSV Antibody DP + L-Arg•HCl + L-Lys•HCl 8W25° C. | 2.34 | 97.4 | 0.25 |
| Anti-RSV Antibody DP + L-Arg•HCl + L-Lys•HCl 8W40° C. | 3.36 | 93.7 | 2.95 |

Figure 1A:
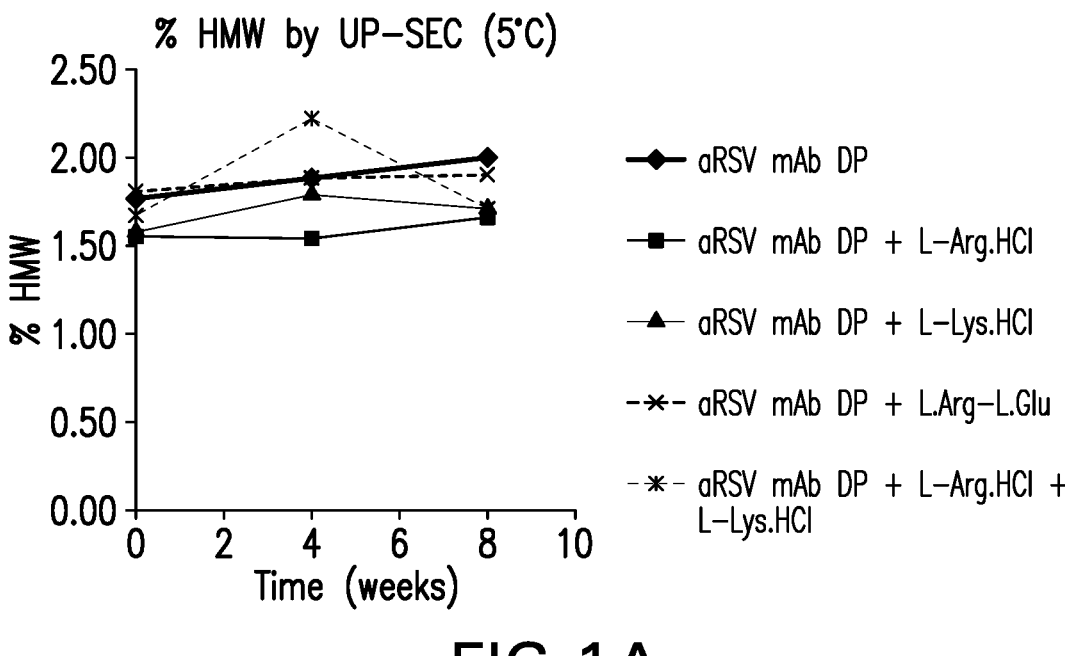
FIGS. 1A-1C show results of UPSEC % HMW, % mAb (monomer) and % LMW vs. Time Data of an anti-RSV antibody formulations at 5° C. storage conditions.
Figure 1B:
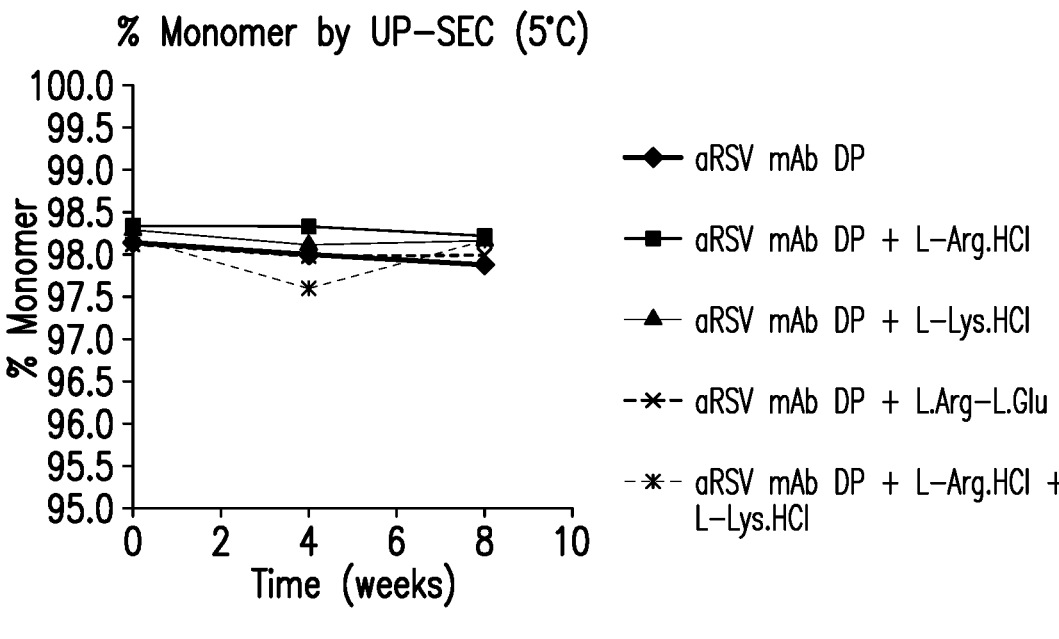
Figure 1C:
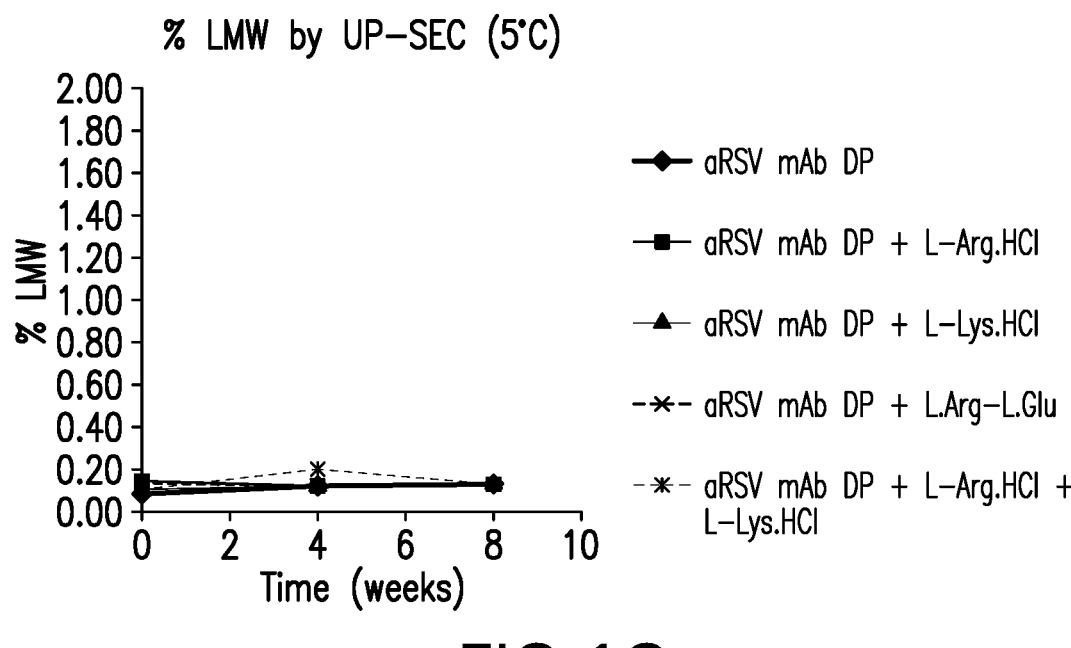
Figures 2A, 2B:
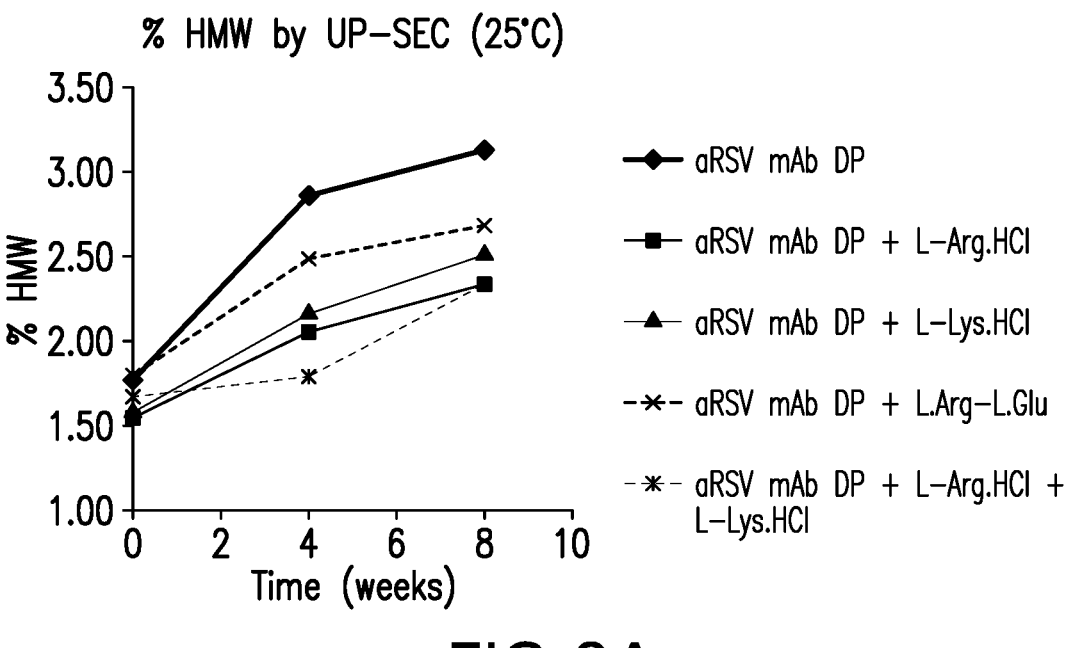
FIGS. 2A-2C show results of UPSEC % HMW, % mAb (monomer) and % LMW vs. Time Data of an anti-RSV antibody formulations at 25° C. storage conditions.
Figure 2C:
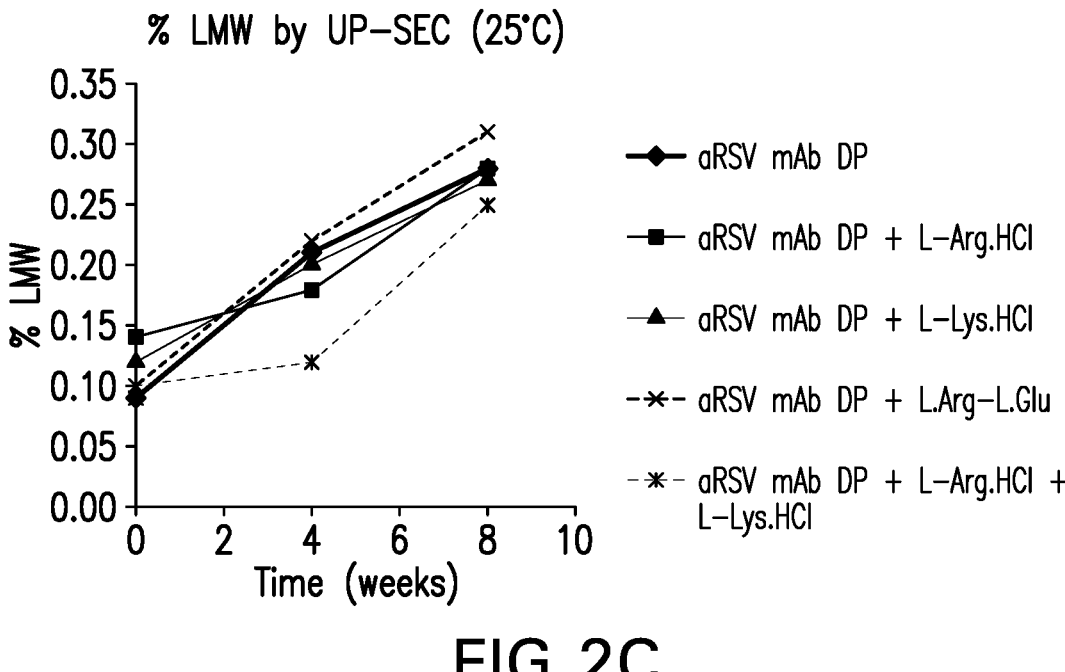
Figures 3A, 3B:
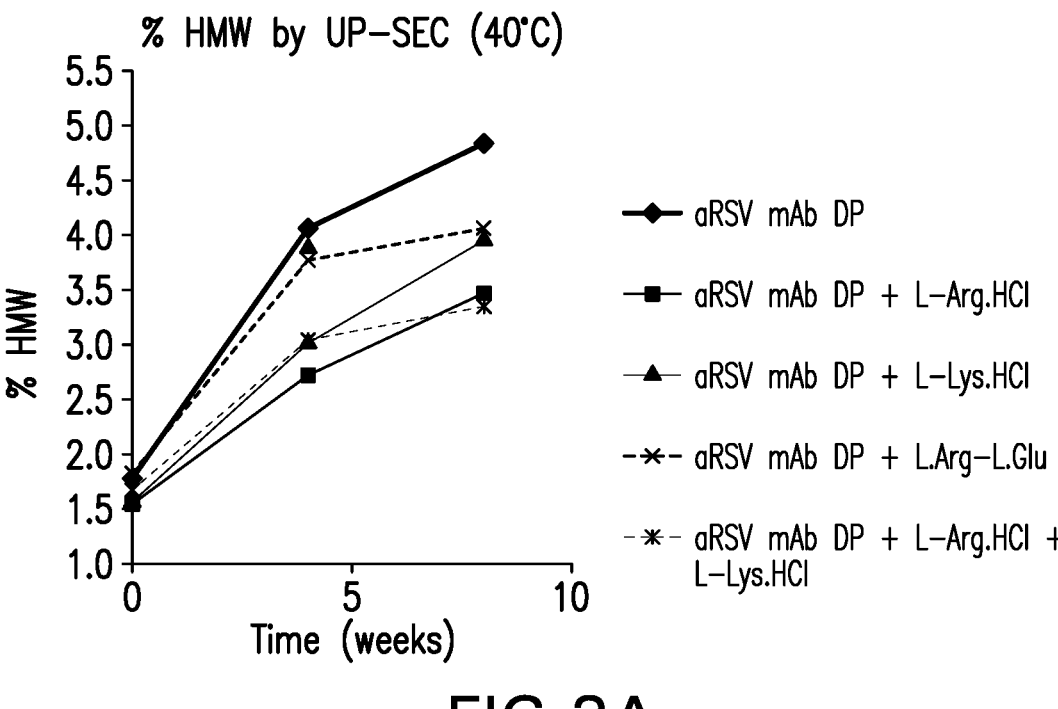
FIGS. 3A-3C show results of UPSEC % HMW, % mAb (monomer) and % LMW vs. Time Data of an anti-RSV antibody formulations at 40° C. storage conditions.
Figure 3C:
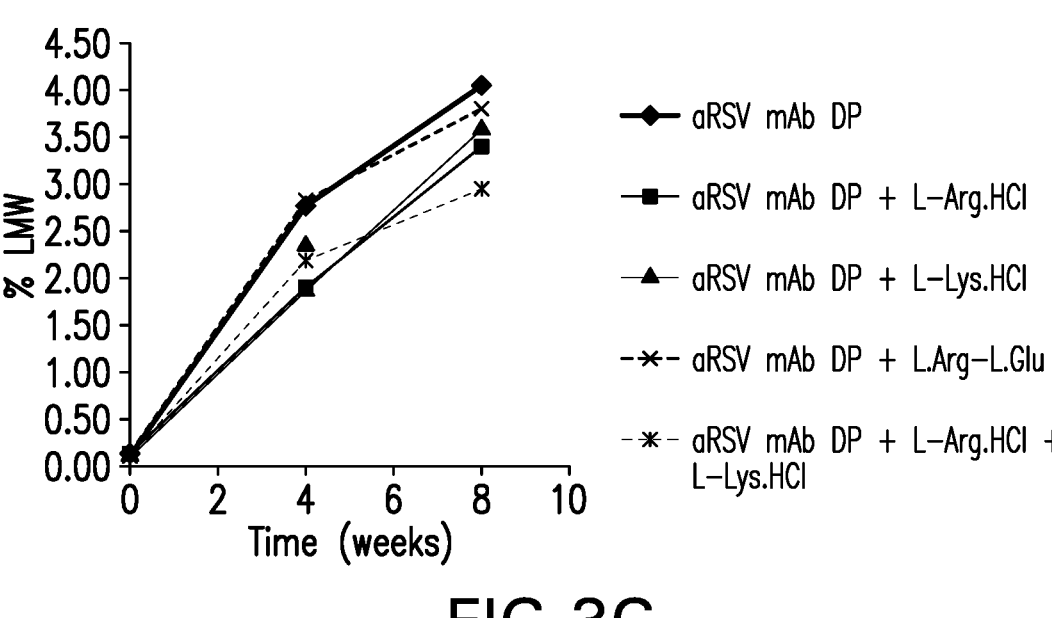

As shown in FIG. 1, FIG. 2, and FIG. 3, UP-SEC analysis of the samples to determine the percentage of HMW and percentage of monomer indicated that at 5° C., 25° C. and 40° C., all the formulations showed a trend of increase in % HMW peak and % LMW peak (and a consequent decrease in % monomer peak) up to the 8-week time point. At 25° C., all the formulations showed similar trends, but smaller changes, as compared to 40° C. At 5° C., no substantial changes were observed.

As shown in FIG. 2 and FIG. 3, formulation 1 shows a greater increase in % HMW and % LMW as compared to the other formulations. Additionally, formulation 1 showed a greater decrease of % monomer. Thus, all four sets of excipients decrease the % HMW and % LMW and thus improve the stability of the anti-RSV antibody DP.

Example 3

Anti-RSV Antibody Formulation Excipient Screening (Amino Acids and Mixtures Thereof) to Improve Chemical Stability of the Anti-RSV Antibody This study compared the stability of an anti-RSV antibody in 10 mM histidine (pH=6), 0.02% PS80, 7% sucrose in the presence of (i) 50 mM L-Arg·HCl or (ii) 50 mM L-Lys·HCl or (iii) mixture of 25 mM L-Arg and 25 mM L-Glu or (iv) mixture of 25 mM L-Arg·HCl and 25 mM Lys·HCl.

These four excipients were tested to improve chemical stability. The four tested excipients were:

(i) 50 mM L-Arg·HCl;
(ii) 50 mM L-Lys·HCl;
(iii) a mixture of 25 mM L-Arg and 25 mM L-Glu; and
(iv) a mixture of 25 mM L-Arg·HCl and 25 mM Lys·HCl.

The first two excipients were examined to understand the effects of the positively charged lysine and arginine in the presence of the chloride counteranion. The third excipient was tested to understand the effect of arginine in the presence of another counteranion (glutamate). The fourth excipient was a mixture of the first two excipients to determine whether the two excipients can play a complementary role. It was hypothesized that this mixture may play a better role than the individual excipients, as the mixture of excipients have different pKa and differentially shields the surface change distribution of the mAb, and this may impact chemical degradation of the mAb.

To evaluate the stability of the formulations, the five formulations were filled into vials and staged on stability at 5° C. (ambient humidity), 25° C. (60% relative humidity), and 40° C. (7500 relative humidity) for eight weeks protected from light. The five formulations are as shown in Example 2.

Ion exchange chromatography was performed to evaluate the chemical stability and to monitor the change in the charge variant profile over time. An ion exchange HPLC method was performed using a Dionex ProPac WCX-1 column and a UV detector at 280 nm. Samples were diluted in purified water, and 80 µg were injected for analysis. The mobile phase used for the IEX analysis of the thermal stability samples was a gradient of the following mobile phases (mobile phase A:20 mM MOPS, pH 7.2; mobile phase B: 50 mM sodium phosphate, 60 mM sodium chloride pH 8.0). The assay is performed using a mobile phase gradient from 20 mM MOPS, pH 7.2 to 50 mM sodium phosphate, 60 mM NaCl, pH 8.0. UV detection was performed at 280 nm.

The HP-IEX data to evaluate the levels of Acidic Variants, 00 Main Peak and 00 Basic Variants is shown in Table 4. [T0=Time 0; 4 W=4 Weeks; and 8 W=8 Weeks]

TABLE 4

| | Reportable % Peak Areas | | |
| Sample Name | Acidic Variants | Total Main | Basic Variants |
| --- | --- | --- | --- |
| Anti-RSV Antibody DP control T05° C. | 25.18 | 58.1 | 16.68 |
| Anti-RSV Antibody DP control T05° C. 4W5° C. | 24.97 | 58.9 | 16.10 |
| Anti-RSV Antibody DP control T05° C. 4W25° C. | 28.41 | 54.1 | 17.47 |
| Anti-RSV Antibody DP control T05° C. 4W40° C. | 44.06 | 37.5 | 18.41 |
| Anti-RSV Antibody DP control T05° C. 8W5° C. | 24.57 | 59.0 | 16.38 |
| Anti-RSV Antibody DP control T05° C. 8W25° C. | 30.62 | 52.0 | 17.38 |
| Anti-RSV Antibody DP control T05° C. 8W40° C. | 53.49 | 28.7 | 17.82 |
| Anti-RSV Antibody DP + L-Arg•HCl T05° C. | 24.23 | 59.8 | 15.92 |
| Anti-RSV Antibody DP + L-Arg•HCl 4W5° C. | 24.43 | 59.2 | 16.35 |
| Anti-RSV Antibody DP + L-Arg•HCl 4W25° C. | 26.05 | 56.6 | 17.39 |
| Anti-RSV Antibody DP + L-Arg•HCl 4W40° C. | 35.13 | 46.0 | 18.88 |
| Anti-RSV Antibody DP + L-Arg•HCl 8W5° C. | 24.00 | 59.7 | 16.34 |
| Anti-RSV Antibody DP + L-Arg•HCl 8W25° C. | 28.25 | 53.2 | 18.54 |
| Anti-RSV Antibody DP + L-Arg•HCl 8W40° C. | 48.43 | 32.6 | 18.96 |
| Anti-RSV Antibody DP + Lys•HCl T05° C. | 23.98 | 60.3 | 15.72 |
| Anti-RSV Antibody DP + Lys•HCl 4W5° C. | 24.08 | 59.8 | 16.09 |
| Anti-RSV Antibody DP + Lys•HCl 4W25° C. | 25.25 | 57.4 | 17.37 |
| Anti-RSV Antibody DP + Lys•HCl 4W40° C. | 34.94 | 45.7 | 19.36 |
| Anti-RSV Antibody DP + Lys•HCl 8W5° C. | 23.95 | 59.9 | 16.14 |
| Anti-RSV Antibody DP + Lys•HCl 8W25° C. | 27.79 | 53.6 | 18.59 |
| Anti-RSV Antibody DP + Lys•HCl 8W40° C. | 48.05 | 32.7 | 19.28 |
| Anti-RSV Antibody DP + L-Arg•L-Glu T05° C. | 24.55 | 59.5 | 15.92 |
| Anti-RSV Antibody DP + L-Arg•L-Glu 4W5° C. | 24.34 | 59.7 | 15.94 |
| Anti-RSV Antibody DP + L-Arg•L-Glu 4W25° C. | 29.80 | 52.6 | 17.63 |
| Anti-RSV Antibody DP + L-Arg•L-Glu 4W40° C. | 47.35 | 34.8 | 17.89 |
| Anti-RSV Antibody DP + L-Arg•L-Glu 8W5° C. | 24.46 | 59.4 | 16.14 |
| Anti-RSV Antibody DP + L-Arg•L-Glu 8W25° C. | 32.22 | 49.2 | 18.55 |
| Anti-RSV Antibody DP + L-Arg•L-Glu 8W40° C. | 55.41 | 26.8 | 17.77 |
| Anti-RSV Antibody DP + L-Arg•HCl + Lys•HCl T05° C. | 23.40 | 60.9 | 15.68 |
| Anti-RSV Antibody DP + L-Arg•HCl + Lys•HCl 4W5° C. | 22.84 | 61.2 | 15.93 |
| Anti-RSV Antibody DP + L-Arg•HCl + Lys•HCl 4W25° C. | 25.02 | 57.5 | 17.45 |
| Anti-RSV Antibody DP + L-Arg•HCl + Lys•HCl 4W40° C. | 36.75 | 44.0 | 19.29 |
| Anti-RSV Antibody DP + L-Arg•HCl + Lys•HCl 8W5° C. | 22.71 | 61.4 | 15.93 |
| Anti-RSV Antibody DP + L-Arg•HCl + Lys•HCl 8W25° C. | 25.97 | 56.1 | 17.97 |
| Anti-RSV Antibody DP + L-Arg•HCl + Lys•HCl 8W40° C. | 42.05 | 38.9 | 19.04 |

Figure 4A:
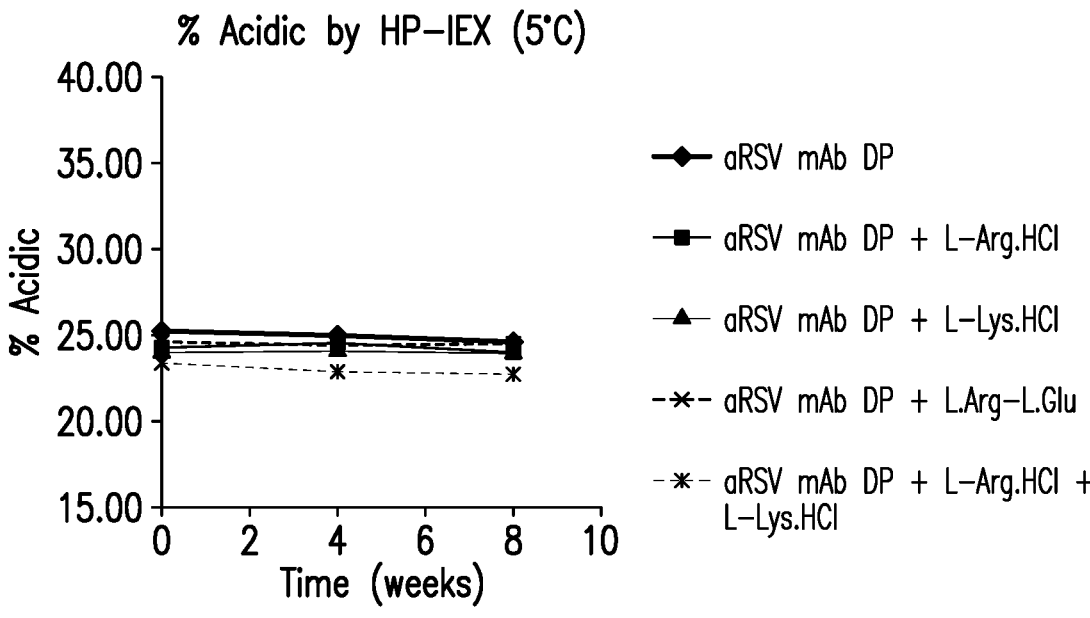
FIGS. 4A-4B show results of HP-IEX % Total Acidic Peaks and % Main Peak vs. Time of an anti-RSV antibody formulations at 5° C. storage conditions.
Figure 4B:
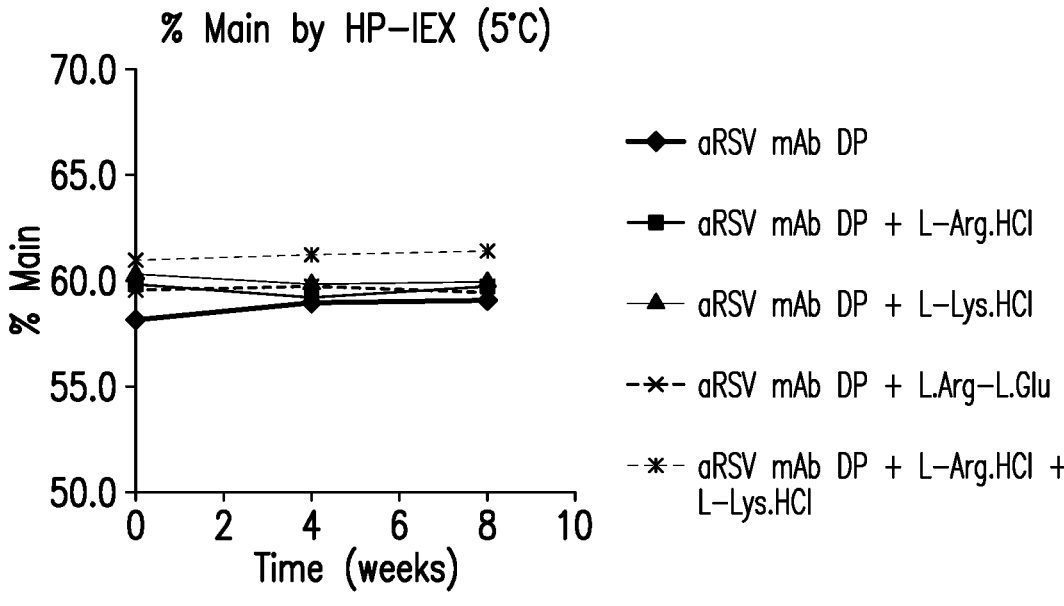
Figure 5A:
FIGS. 5A-5B show results of HP-IEX % Total Acidic Peaks and % Main Peak vs. Time of an anti-RSV antibody formulations at 25° C. storage conditions.
Figure 5A:
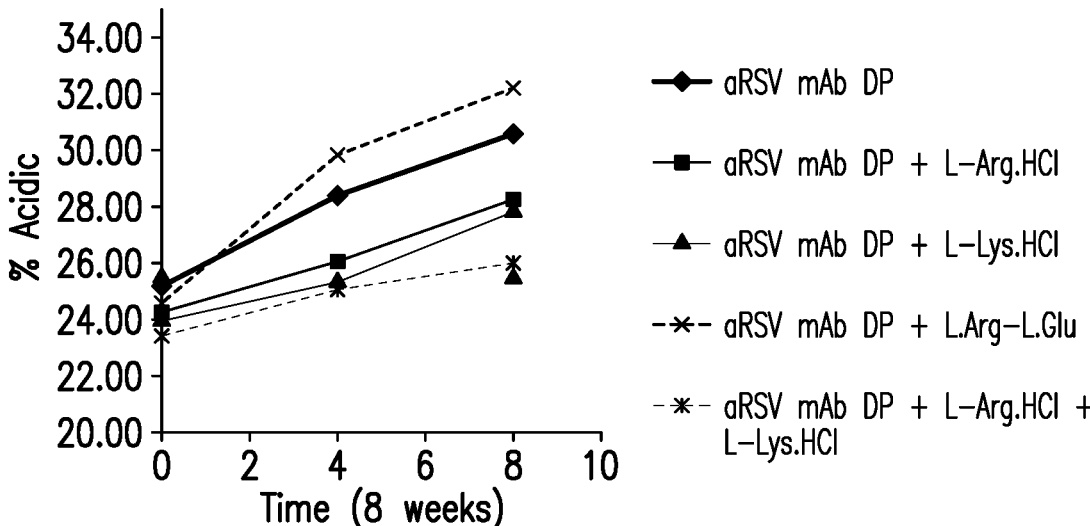
Figure 5B:
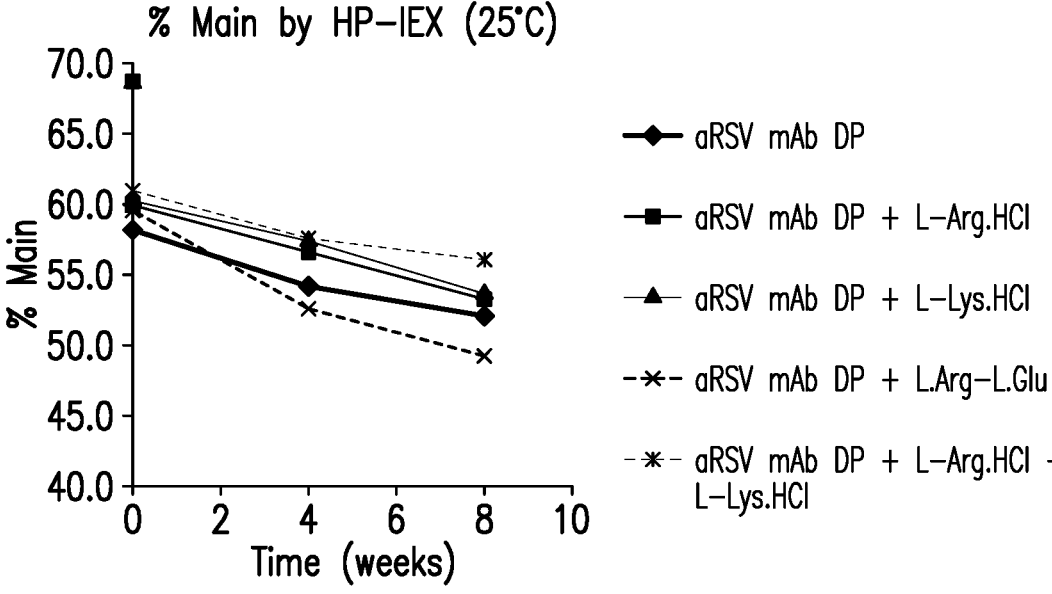
Figure 6A:
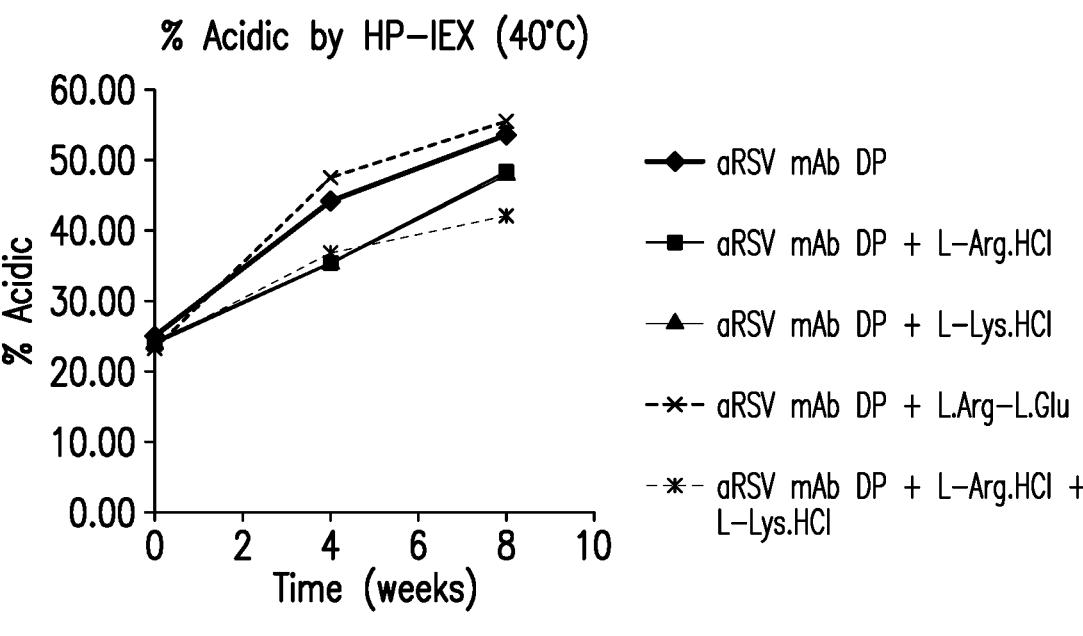
FIGS. 6A-6B show results of HP-IEX % Total Acidic Peaks and % Main Peak vs. Time of an anti-RSV antibody formulations at 40° C. storage conditions.
Figure 6B:
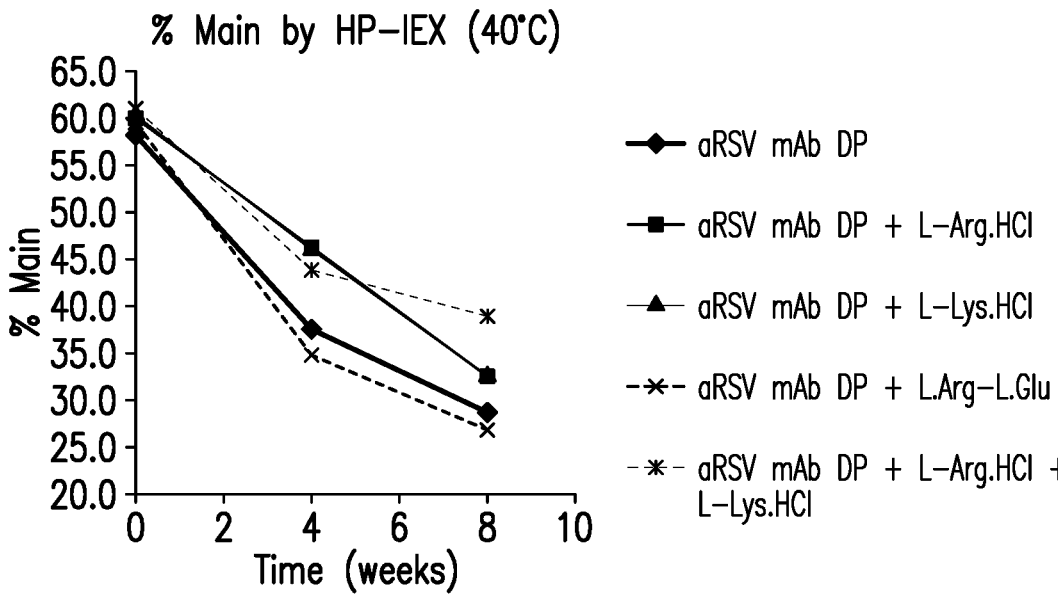

As shown in FIG. 4, FIG. 5 and FIG. 6, HIP-IEX analysis of the samples to determine the chemical stability indicated that at 5° C., 25° C. and 40° C., all the formulations showed a trend towards an increase in 00 acidic peak and a consequent decrease in 00 monomer peak up to the 8-week time point. At 25° C., all the formulations showed similar trends, but smaller changes, as compared to 40° C. At 5° C., no substantial changes were observed.

As seen in FIG. 5 and FIG. 6, formulation 1 shows a greater increase in 00 acidic peak as compared to the other formulations. Additionally, formulation 1 showed a greater decrease of % main peak as compared to the other formulations. Thus, all the four sets of excipients decrease the % acidic peak and thus improves the chemical stability of the anti-RSV antibody DP.

Example 4

Anti-RSV Antibody Formulation Excipient Screening (to Decrease Viscosity of the Anti-RSV Antibody)

This study compared the stability of an anti-RSV antibody in 10 mM histidine (pH=6), 0.02% PS80, 700 sucrose in the presence of (i) 50 mM L-Arg·HCl or (ii) 50 mM L-Lys·HCl or (iii) mixture of 25 mM L-Arg and 25 mM L-Glu or (iv) mixture of 25 mM L-Arg·HCl and 25 mM L-Lys·HCl.

These four excipients were tested for their ability to decrease viscosity of the anti-RSV antibody. The four tested excipients were:

(i) 50 mM L-Arg·HCl;
(ii) 50 mM L-Lys·HCl;

(iii) a mixture of 25 mM L-Arg and 25 mM L-Glu; and
(iv) a mixture of 25 mM L-Arg·HCl and 25 mM L-Lys·HCl.

The first two excipients were examined to understand the effects of the positively charged lysine and arginine in the presence of the chloride counteranion. The third excipient was tested to understand the effect of arginine in the presence of another counteranion (glutamate). The fourth excipient was a mixture of the first two excipients to see if the two excipients can play a complementary role. It was hypothesized that this mixture may play a better role than the individual excipients, as the mixture of excipients have different pKa and differentially shields the surface change distribution of the mAb, thereby increasing the repulsive protein-protein interaction and decreasing viscosity of the mAb.

To measure viscosity, the samples were loaded into a 500 μl syringe and viscosity was measured (five times for each sample) at 20° C. with an MVROC Viscometer. VROC sensors detected viscosity by measuring the pressure drop as samples flow through the sensor's flow channel at designated positions from the inlet. Viscosity was measured as a function of shear rate with shear rates of samples being determined by sample viscosity.

Figure 7:
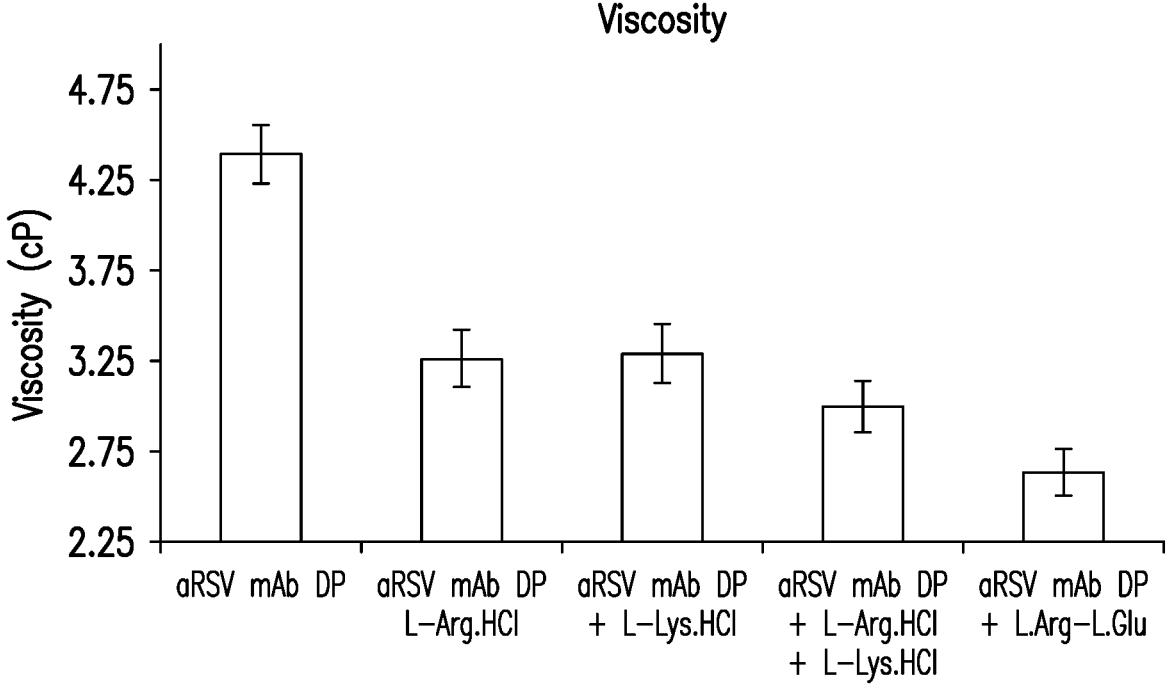
FIG. 7 shows results of excipient reducing viscosity of 100 mg/mL anti-RSV antibody (all experiments were repeated n=5 to derive a standard deviation).

As shown in Table 5 and FIG. 7, all four sets of excipients decrease the viscosity of the anti-RSV antibody DP.

TABLE 5

| Sample Number | Samples | Viscosity (cP) |
|---|---|---|
| S1 | Anti-RSV Antibody | 4.3940 ± 0.1265 |
| S2 | Anti-RSV Antibody + L-Arg•HCl | 3.2658 ± 0.1585 |
| S3 | Anti-RSV Antibody + L-Lys•HCl | 3.2916 ± 0.1633 |
| S4 | Anti-RSV Antibody + (L-Arg•HCl + L-Lys•HCl) | 2.9982 ± 0.1435 |
| S5 | Anti-RSV Antibody + (L-Arg + L-Glu) | 2.6344 ± 0.1288 |

Example 5

Addition of Chelator to Anti-RSV Antibody Formulation to Decrease Aggregation

This study compared the stability of an anti-RSV antibody in 10 mM histidine (pH=6), 0.02% PS80, 7% sucrose in the presence or absence of 50 µM DTPA (Diethylenetriamine pentaacetate).

To evaluate the stability of the formulations, two formulations were filled into vials and staged on stability at 5° C. (ambient humidity), 25° C. (60% relative humidity), and 40° C. (75% relative humidity) for eight weeks protected from light. The two formulations are shown in Table 6.

TABLE 6

| Formulation Number | Description | | | | |
|---|---|---|---|---|---|
| 1 | Anti-RSV antibody (100 mg/mL) | 10 mM Histidine (pH = 6) | 7% Sucrose (w/v) | 0.02% PS80 (w/v) | N/A |
| 2 | Anti-RSV antibody (100 mg/mL) | 10 mM Histidine (pH = 6) | 7% Sucrose (w/v) | 0.02% PS80 (w/v) | 50 µM DTPA |

Samples were assessed by size exclusion chromatography (SEC) for purity in which the percentage of monomer was determined, as well as the percentages of high molecular weight species (HMW) and late eluting peaks (LMW species). Ultra Performance—Size Exclusion Chromatography (UP-SEC) was performed by diluting the samples to 1.0 mg/mL in mobile phase (100 mM sodium phosphate and 100 mM sodium chloride, pH 7.0); flow rate of 0.5 mL/min. The diluted samples were injected (5 µL) into a UPLC equipped with a Waters BEH200 column and a UV detector. Proteins in the sample were separated by size and detected by UV absorption at 214 nm.

The UPSEC data to evaluate the levels of High Molecular Weight Species (HMW or aggregates), % monomer and LMW (Low Molecular Weight species) is shown in Table 7. [T0=Time 0; 4 W=4 Weeks; and 8 W=8 Weeks]

TABLE 7

| Sample Name | Peak | | |
|---|---|---|---|
| | HMW | Monomer | LMW |
| Anti-RSV Antibody DP control T05° C. | 1.77 | 98.1 | 0.09 |
| Anti-RSV Antibody DP control T0 4W5° C. | 1.88 | 98.0 | 0.11 |
| Anti-RSV Antibody DP control T0 4W25° C. | 2.86 | 96.9 | 0.21 |
| Anti-RSV Antibody DP control T0 4W40° C. | 4.05 | 93.2 | 2.77 |
| Anti-RSV Antibody DP control T0 8W5° C. | 2.00 | 97.9 | 0.13 |
| Anti-RSV Antibody DP control T0 8W25° C. | 3.13 | 96.6 | 0.28 |
| Anti-RSV Antibody DP control T0 8W40° C. | 4.83 | 91.1 | 4.05 |
| Anti-RSV Antibody DP + DTPA T05° C. | 1.72 | 98.2 | 0.12 |
| Anti-RSV Antibody DP + DTPA 4W5° C. | 1.81 | 98.1 | 0.11 |
| Anti-RSV Antibody DP + DTPA 4W25° C. | 2.53 | 97.3 | 0.19 |

TABLE 7-continued

| Sample Name | Peak | | |
|---|---|---|---|
| | HMW | Monomer | LMW |
| Anti-RSV Antibody DP + DTPA 4W40° C. | 3.24 | 94.7 | 2.02 |
| Anti-RSV Antibody DP + DTPA 8W5° C. | 1.87 | 98.0 | 0.12 |
| Anti-RSV Antibody DP + DTPA 8W25° C. | 2.68 | 97.1 | 0.21 |
| Anti-RSV Antibody DP + DTPA 8W40° C. | 3.50 | 93.8 | 2.68 |

Figure 8A:
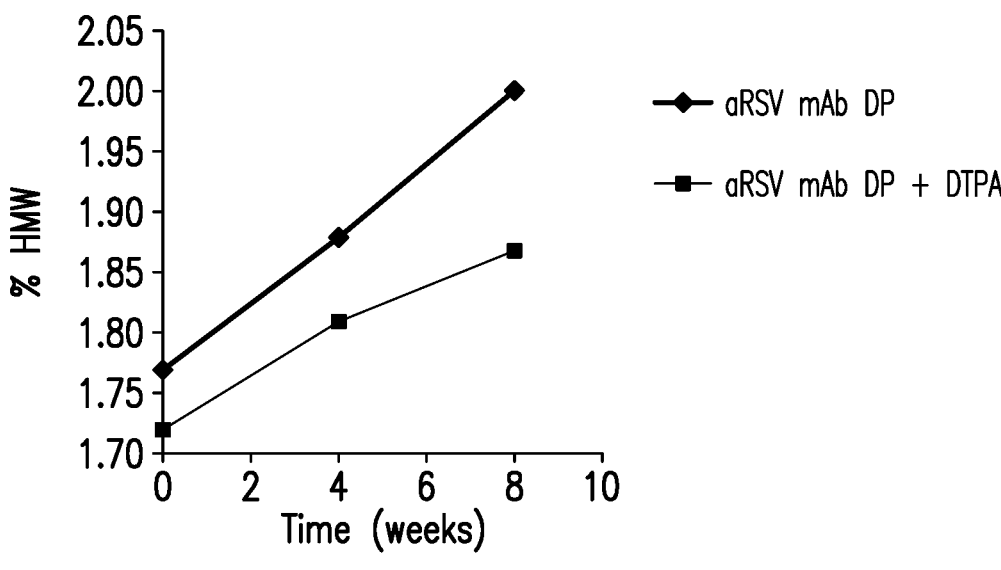
FIGS. 8A-8C show results of UPSEC % HMW, % mAb (monomer) and % LMW vs. Time Data of an anti-RSV antibody formulations at 5° C. storage conditions.
Figure 8B:
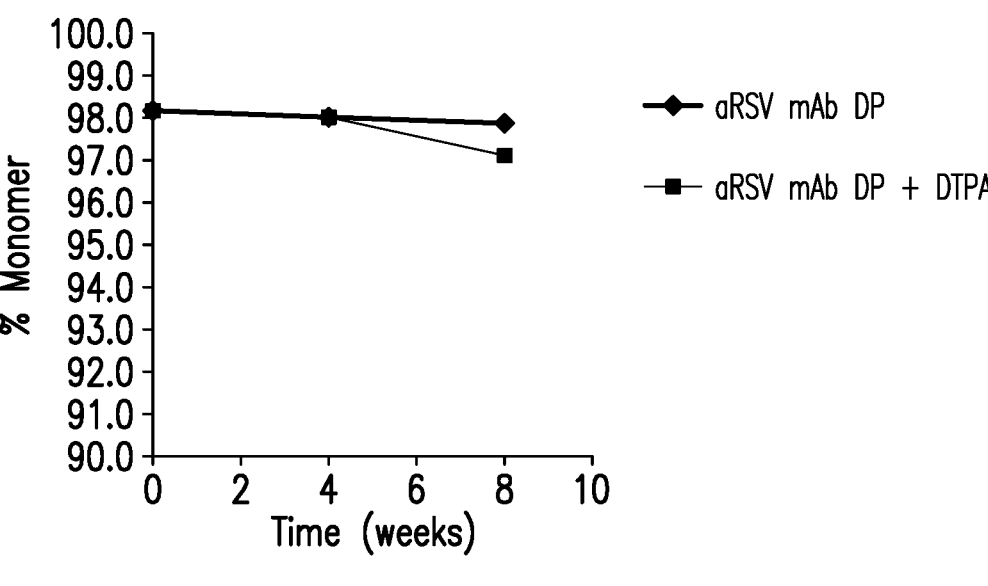
Figure 8C:
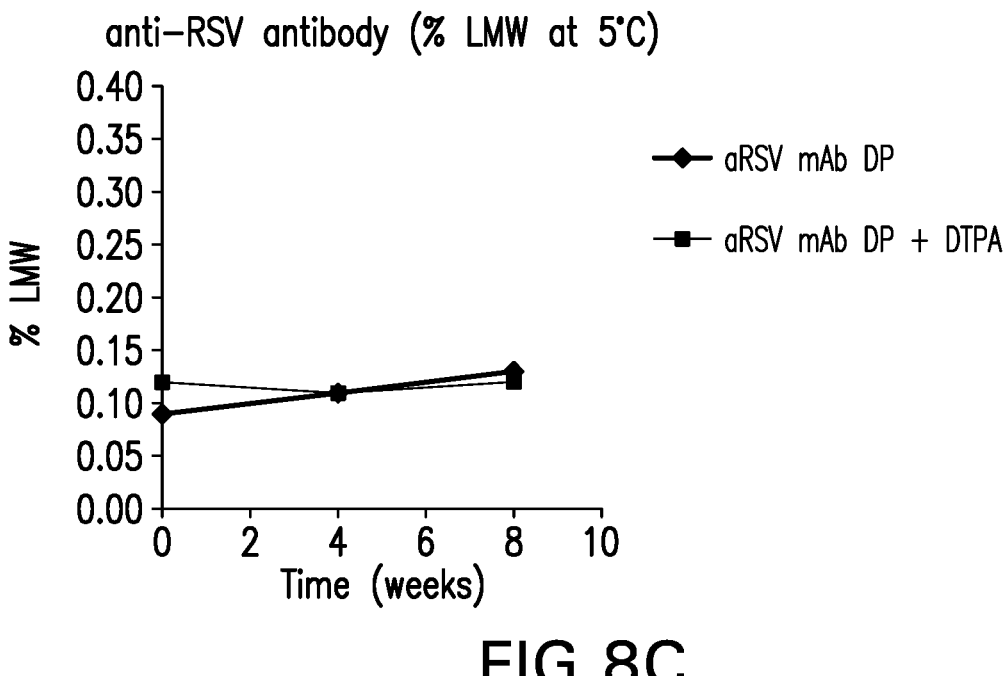
Figure 9A:
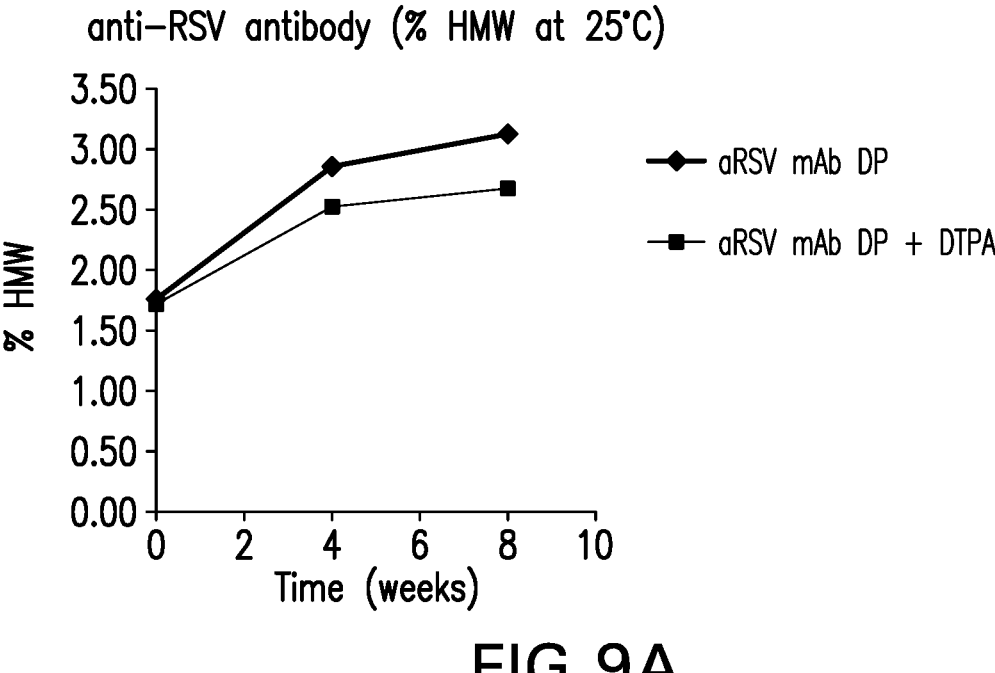
FIGS. 9A-9C show results of UPSEC % HMW, % mAb (monomer) and % LMW vs. Time Data of an anti-RSV antibody formulations at 25° C. storage conditions.
Figure 9B:
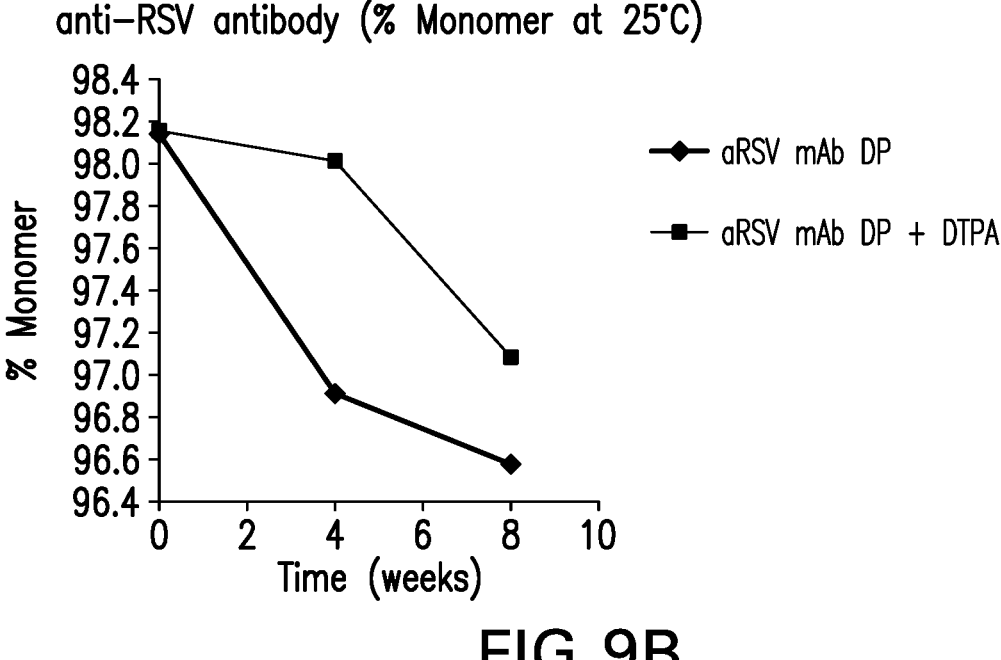
Figure 9C:
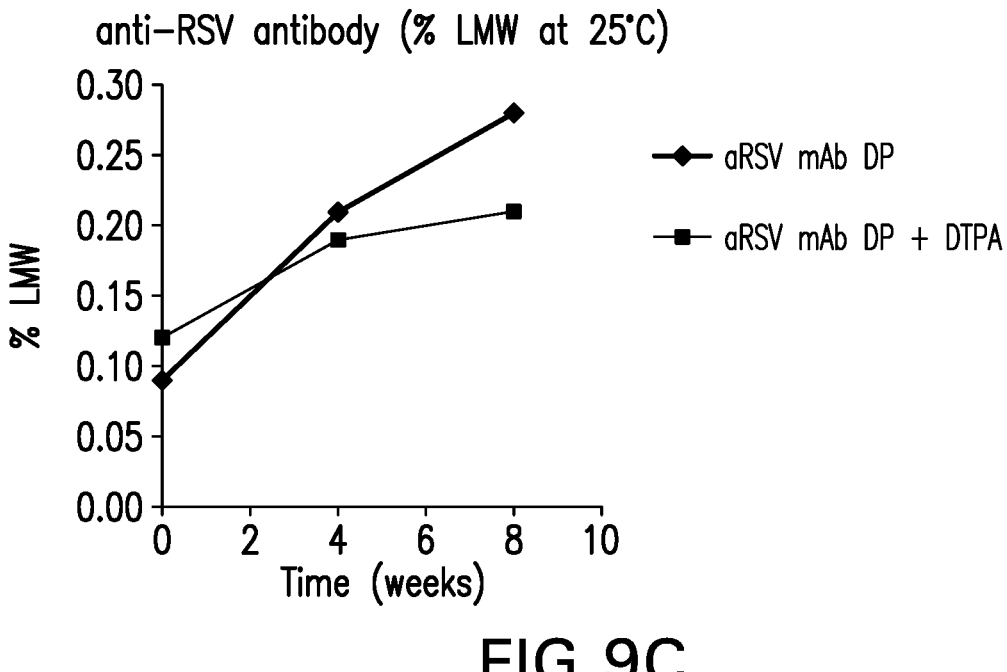
Figure 10A:
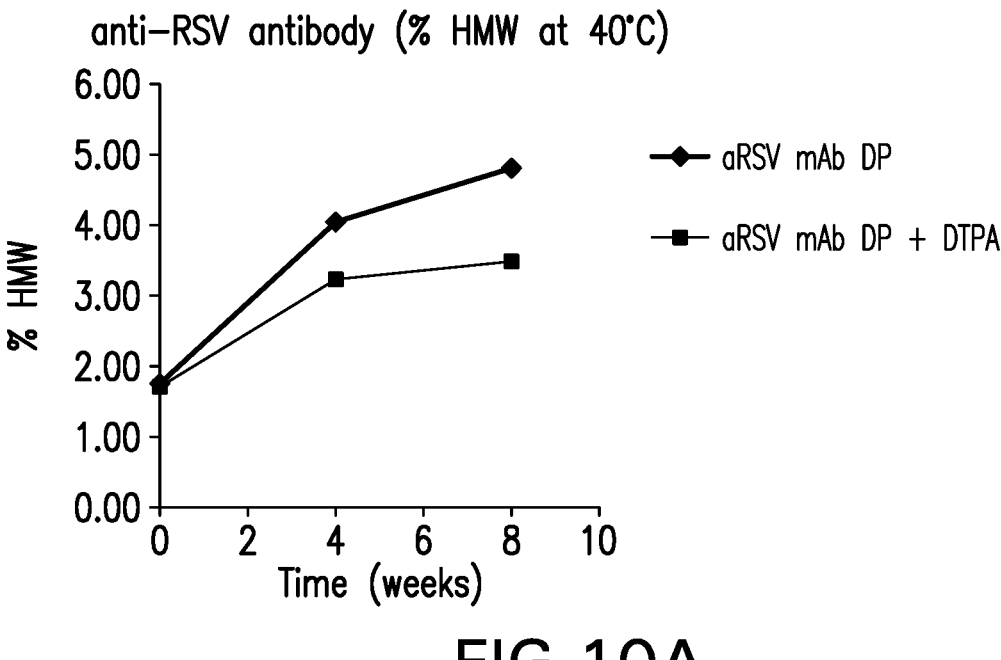
FIGS. 10A-10C show results of UPSEC % HMW, % mAb (monomer) and % LMW vs. Time Data of an anti-RSV antibody formulations at 40° C. storage conditions.
Figure 10B:
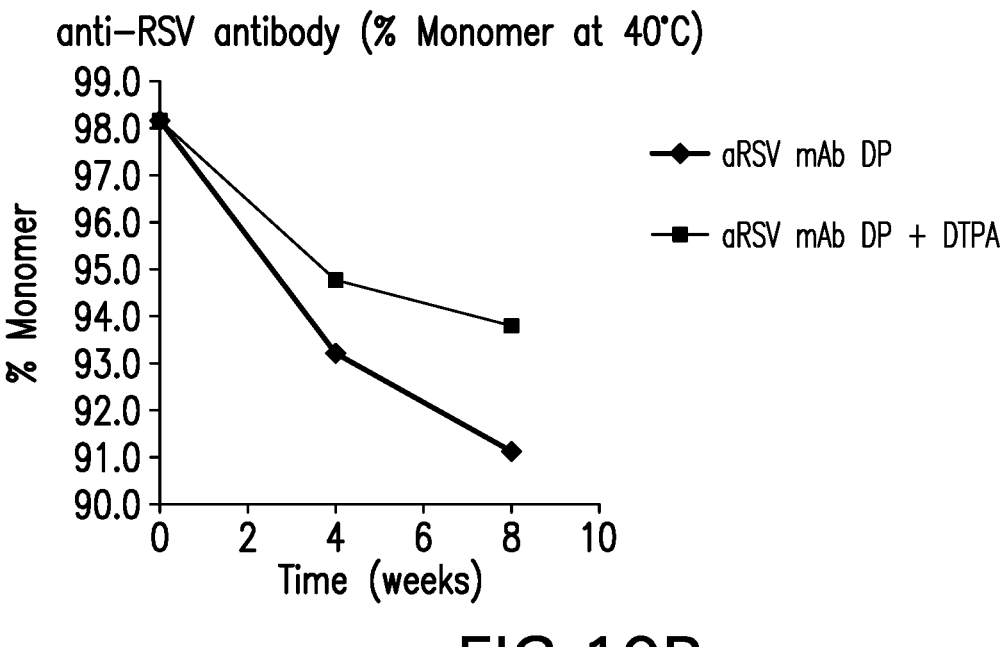
Figure 10C:
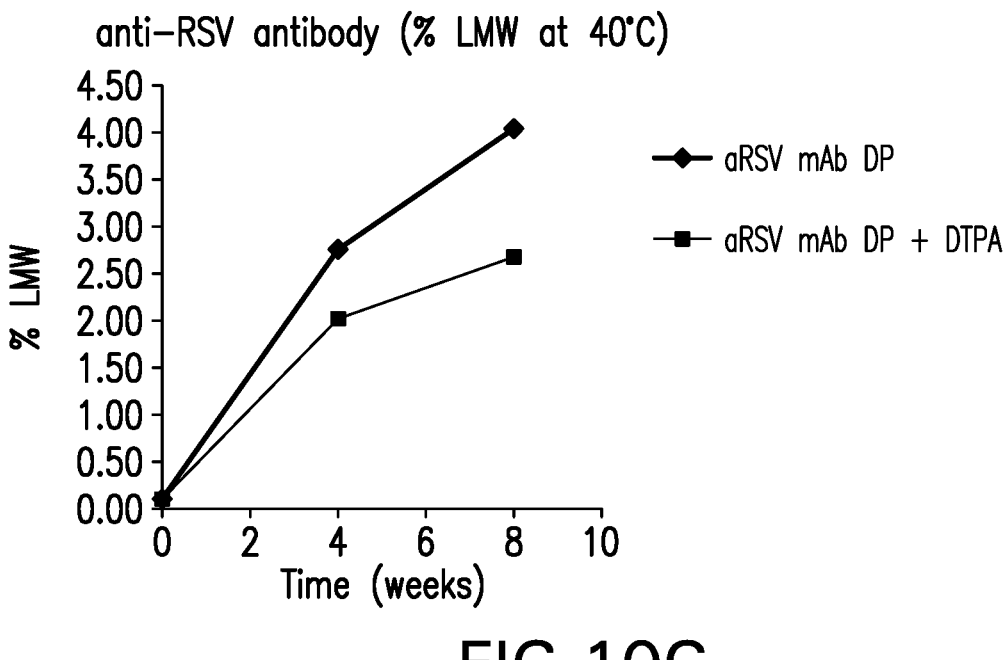

As shown in FIG. 8, FIG. 9 and FIG. 10, UP-SEC analysis of the samples to determine the percentage of HMW and percentage of monomer indicated that at 5° C., 25° C. and 40° C., both formulations showed a trend towards an increase in % HMW peak and % LMW peak (and a consequent decrease in % monomer peak) up to the 8-week time point. At 25° C., both formulations showed similar trends, but smaller changes, as compared to 40° C. At 5° C., no substantial changes were observed.

As seen in FIGS. 9 and 10, formulation 1 showed a greater increase in % HMW and % LMW as compared to formulation 2. Additionally, formulation 1 showed a greater decrease of % monomer as compared to formulation 2. Thus, DTPA (formulation 2) decreases the % HMW and % LMW and thus improves the aggregation of the anti-RSV antibody DP.

Example 6

Addition of Chelator to Anti-RSV Antibody Formulation to Improve Chemical Stability of the Anti-RSV Antibody This study compares the chemical stability of an anti-RSV antibody in 10 mM histidine (pH=6), 0.02% PS80, 7% sucrose in the presence or absence of 50 µM DTPA.

To evaluate the chemical stability of the formulations, two formulations were filled into vials and staged on stability at 5° C. (ambient humidity), 25° C. (60% relative humidity), and 40° C. (75% relative humidity) for eight weeks protected from light. The two formulations are as provided in Example 5.

Ion exchange chromatography was performed to evaluate the chemical stability and to monitor the change in the charge variant profile over time. An ion exchange HPLC method was performed using a Dionex ProPac WCX-10 column and a UV detector at 280 nm. Samples were diluted in purified water, and 80 µg were injected for analysis. The mobile phase used for the IEX analysis of the thermal stability samples was a gradient of the following mobile phases (mobile phase A:20 mM MOPS, pH 7.2; mobile phase B: 50 mM sodium phosphate, 60 mM sodium chloride pH 8.0). The assay was performed using a mobile phase gradient from 20 mM MOPS, pH 7.2 to 50 mM sodium phosphate, 60 mM NaCl, pH 8.0. UV detection was performed at 280 nm.

The HP-IEX data to evaluate the levels of Acidic Variants, % Main Peak and % Basic Variants is shown in Table 8. [T0=Time 0; 4 W=4 Weeks; and 8 W=8 Weeks]

TABLE 8

| Sample Name | Reportable % Peak Areas | | |
|---|---|---|---|
| | Acidic Variants | Total Main | Basic Variants |
| Anti-RSV Antibody DP control T05° C. | 25.18 | 58.1 | 16.68 |
| Anti-RSV Antibody DP control T05° C. 4W5° C. | 24.97 | 58.9 | 16.10 |

TABLE 8-continued

| Sample Name | Reportable % Peak Areas | | |
| | Acidic Variants | Total Main | Basic Variants |
| --- | --- | --- | --- |
| Anti-RSV Antibody DP control T05° C. 4W25° C. | 28.41 | 54.1 | 17.47 |
| Anti-RSV Antibody DP control T05° C. 4W40° C. | 44.06 | 37.5 | 18.41 |
| Anti-RSV Antibody DP control T05° C. 8W5° C. | 24.57 | 59.0 | 16.38 |
| Anti-RSV Antibody DP control T05° C. 8W25° C. | 30.62 | 52.0 | 17.38 |
| Anti-RSV Antibody DP control T05° C. 8W40° C. | 53.49 | 28.7 | 17.82 |
| Anti-RSV Antibody DP + DTPA T05° C. | 22.96 | 61.5 | 15.54 |
| Anti-RSV Antibody DP + DTPA 4W5° C. | 23.00 | 61.8 | 15.19 |
| Anti-RSV Antibody DP + DTPA 4W25° C. | 24.32 | 58.4 | 17.26 |
| Anti-RSV Antibody DP + DTPA 4W40° C. | 35.11 | 45.4 | 19.47 |
| Anti-RSV Antibody DP + DTPA 8W5° C. | 22.79 | 61.0 | 16.25 |
| Anti-RSV Antibody DP + DTPA 8W25° C. | 25.25 | 56.8 | 17.95 |
| Anti-RSV Antibody DP + DTPA 8W40° C. | 40.90 | 39.2 | 19.86 |

Figure 11A:
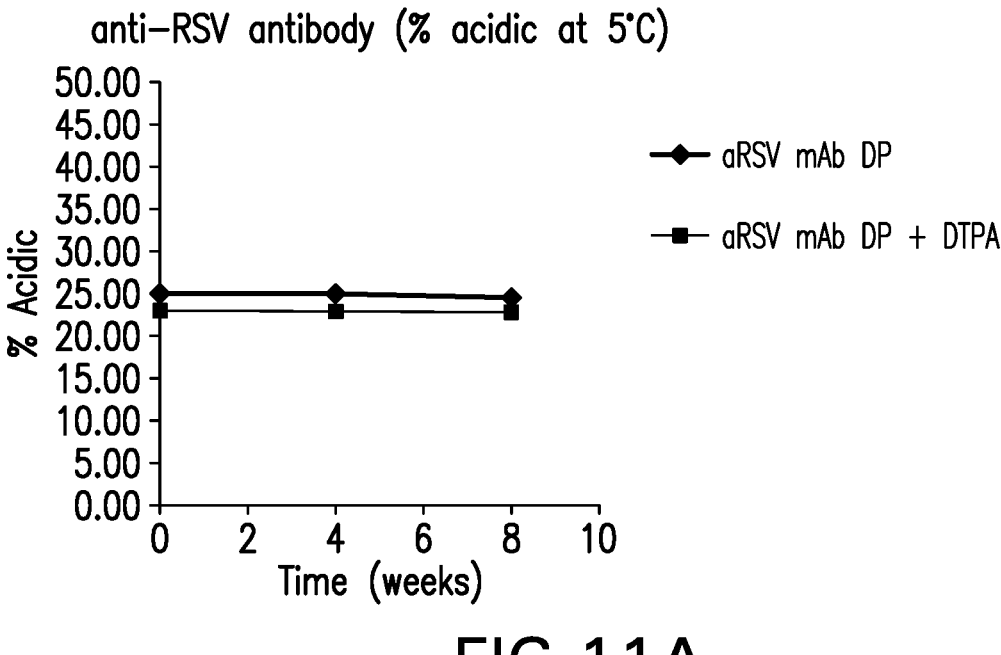
FIGS. 11A-11B show results of HP-IEX % Total Acidic Peaks and % Main Peak vs. Time of an anti-RSV antibody formulations at 5° C. storage conditions.
Figure 11B:
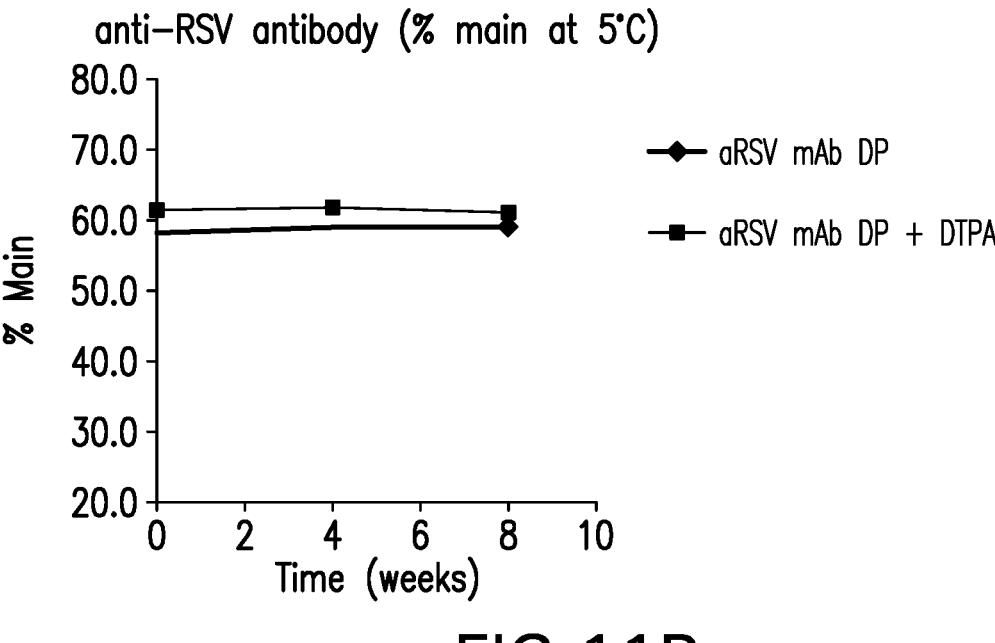
Figures 12A, 12B:
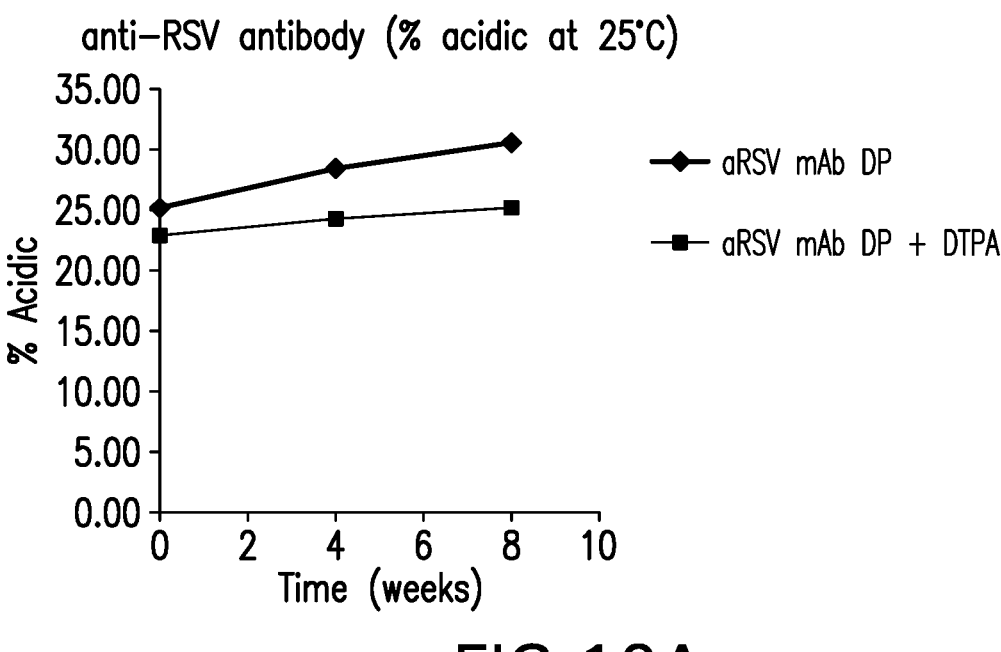
FIGS. 12A-12B show results of HP-IEX % Total Acidic Peaks and % Main Peak vs. Time of an anti-RSV antibody formulations at 25° C. storage conditions.

As shown in FIG. 11, FIG. 12 and FIG. 13, HP-IEX analysis of the samples to determine chemical stability indicated that at 5° C., 25° C. and 40° C., both formulations showed a trend towards an increase in % acidic peak and a consequent decrease in % monomer peak) up to the 8-week time point. At 25° C., both formulations showed similar trends, but smaller changes, as compared to 40° C. At 5° C., no substantial changes were observed.

As seen in FIGS. 12 and 13, formulation 1 showed a greater increase in % acidic peak as compared to formulation 2. Additionally, formulation 1 showed a greater decrease of % main peak as compared to formulation 2. Thus, DTPA (formulation 2) decreased the % acidic peak and thus improves the chemical stability of an anti-RSV antibody DP.

Example 7

Addition of Chelator to Anti-RSV Antibody Formulation to Decrease PS80 Degradation This study compared the chemical stability of PS80 in an anti-RSV antibody in 10 mM histidine (pH=6), 0.02% PS80, 7% sucrose in the presence or absence of 50 μM DTPA. Degradation of PS80 is commonly seen upon long-term storage of mAbs and the experiment was performed to determine if DTPA is compatible with PS80.

To evaluate the chemical stability of PS80 in two formulations, the two formulations were filled into vials and staged on stability at 5° C. (ambient humidity), 25° C. (60% relative humidity), and 40° C. (75% relative humidity) for eight weeks protected from light. The two formulations are as provided in Example 5.

The results in Table 9 show similar degradation profiles of PS80 for both formulations. FIG. 14 shows the % degradation of PS80 at 40° C. The % degradation was slightly less for formulation 2 (in the presence of DTPA). Thus, DTPA might protect against PS80 degradation and these two excipients (DTPA and PS80) are mutually compatible. [T0=Time 0; 4 W=4 Weeks; and 8 W=8 Weeks]

TABLE 9

| Sample Name | PS80 concentration |
| --- | --- |
| Anti-RSV Antibody DP control T05° C. | 0.28 |
| Anti-RSV Antibody DP control T05° C. 4W5° C. | 0.27 |
| Anti-RSV Antibody DP control T05° C. 4W25° C. | 0.21 |
| Anti-RSV Antibody DP control T05° C. 4W40° C. | 0.19 |

TABLE 9-continued

| Sample Name | PS80 concentration |
| --- | --- |
| Anti-RSV Antibody DP control T05° C. 8W5° C. | 0.25 |
| Anti-RSV Antibody DP control T05° C. 8W25° C. | 0.18 |
| Anti-RSV Antibody DP control° T05° C. 8W40° C. | 0.16 |
| Anti-RSV Antibody DP + DTPA T05° C. | 0.25 |
| Anti-RSV Antibody DP + DTPA 4W5° C. | 0.23 |
| Anti-RSV Antibody DP + DTPA 4W25° C. | 0.19 |
| Anti-RSV Antibody DP + DTPA 4W40° C. | 0.17 |
| Anti-RSV Antibody DP + DTPA 8W5° C. | 0.23 |
| Anti-RSV Antibody DP + DTPA 8W25° C. | 0.16 |
| Anti-RSV Antibody DP + DTPA 8W40° C. | 0.16 |

Example 8

Increasing Excipient Concentrations to Decrease Viscosity and Maintain Stability To assess the effect of increased concentrations of excipients to decrease viscosity, anti-RSV antibody was formulated at two different concentrations (around 200 mg/ml and 154 mg/mL) into four different formulations: a first formulation of 10 mM histidine, 7% sucrose and 0.02% PS80, pH6, and three formulations adding an additional high concentration of excipient: 70 mM Histidine (for a total concentration of 80 mM histidine), 70 mM Lysine, or 70 mM Arg.

To measure the viscosity of the four formulations, the samples were loaded into a 500 μl syringe and viscosity was measured (four times for each sample) at room temperature with an MVROC Viscometer. VROC sensors detected viscosity by measuring the pressure drop as samples flow through the sensor's flow channel at designated positions from the inlet. Viscosity was measured as a function of shear rate (measured in reciprocal seconds [$S^{-1}$]). The shear rate used was 997 $S^{-1}$. FIG. 15 shows a bar graph comparing the four different formulations of anti-RSV antibody at their respective concentrations (around 200 mg/ml and at 154 mg/mL).

Compared to a formulation of 10 mM histidine, 7% sucrose and 0.02% PS80, pH6, the addition of higher concentrations of histidine, lysine, and arginine showed a substantial decrease in viscosity. As shown in FIG. 15, the four formulations did not show a significantly different viscosity at an anti-RSV antibody concentration of 154 mg/mL. However, at the higher anti-RSV antibody concentrations of around 200 mg/mL, the formulations using additional 70 mM histidine, 70 mM lysine, or 70 mM arginine showed a significant decrease in mean viscosity compared with the first formulation. Anti-RSV antibody at 213 mg/mL in the formulation of 10 mM histidine, 7% sucrose and 0.02% PS80, pH6 has a mean viscosity of 64.97 centipoise (cP). Using additional excipient of 70 mM histidine (total concentration of 80 mM histidine) reduced the mean viscosity of 204 mg/mL anti-RSV antibody formulation to 30.85 cP. Using 70 mM lysine as an excipient reduced the mean viscosity of 192 mg/mL anti-RSV antibody formulation to 19.81 cP. Using 70 mM arginine as an excipient reduced the mean viscosity of 217 mg/mL anti-RSV antibody formulation to 29.27 cP.

The stability of each of the formulations was tracked for 3 months at 5° C., 25° C. and 40° C. Samples were assessed by size exclusion chromatography (SEC) for purity in which the percentage of monomer was determined, as well as the percentages of high molecular weight species (HMW) and late eluting peaks (LMW species). Ion exchange chromatography was performed as described in Example 6 to evaluate the chemical stability and to monitor the change in the charge variant profile over time. Values are listed in Table 10 below.

TABLE 10

| | 10 mM His (213 mg/mL) | 80 mM His (204 mg/mL) | 10 mM His, 70 mM Lys (192 mg/mL) | 10 mM His, 70 mM Arg (217 mg/mL) |
|---|---|---|---|---|
| Month 0, Monomer % (5° C./25° C./40° C.) | 97.2/97.2/97.2 | 98.0/98.0/98.0 | 97.7/97.7/97.7 | 97.6/97.6/97.6 |
| Month 0, High Mol. Wt. % (5° C./25° C./40° C.) | 2.4/2.4/2.4 | 1.6/1.6/1.6 | 1.8/1.8/1.8 | 1.9/1.9/1.9 |
| Month 0, Low Mol. Wt. % (5° C./25° C./40° C.) | 0.4/0.4/0.4 | 0.4/0.4/0.4 | 0.5/0.5/0.5 | 0.5/0.5/0.5 |
| Month 3, Monomer % (5° C./25° C./40° C.) | 96.9/93.4/26.5 | 97.7/96.3/36.8 | 97.3/62.4/52.2 | 97.3/94.4/3.8 |
| Month 3, High Mol. Wt. % (5° C./25° C./40° C.) | 2.4/4.0/44.2 | 1.6/2.4/40.3 | 1.9/34.6/37.2 | 1.9/2.5/65.4 |
| Month 3, Low Mol. Wt. % (5° C./25° C./40° C.) | 0.7/2.6/29.3 | 0.7/1.3/22.9 | 0.8/3.1/10.6 | 0.8/3.1/30.9 |

Compared to a formulation of 10 mM histidine, 7% sucrose and 0.02% PS80, pH6, the addition of higher concentrations of histidine, lysine, and arginine did not lead to a significant increase of high molecular weight species or low molecular weight species, and did not lead to a significant decrease in the percentage monomer.

What is claimed is:

1. An anti-RSV antibody formulation comprising:
a) about 50 mg/mL to about 250 mg/mL of an anti-RSV antibody, or antigen-binding fragment thereof,
wherein the anti-RSV antibody, or antigen-binding fragment thereof, comprises a heavy chain variable region having the amino acid sequence of SEQ ID NO: 7 and a light chain variable region having the amino acid sequence of SEQ ID NO: 8;
b) about 5 mM to about 20 mM histidine;
c) about 4% to about 8% (w/v) sucrose;
d) about 70 mM of L-arginine or a pharmaceutically acceptable salt of L-arginine; and
e) about 0.01% to about 0.10% (w/v) polysorbate 80, and wherein the formulation is free of L-glutamate.

2. The anti-RSV antibody formulation of claim 1, comprising about 125 mg/mL to about 175 mg/mL of the anti-RSV antibody, or antigen-binding fragment thereof.

3. The anti-RSV antibody formulation of claim 1, comprising about 150 mg/ml of the anti-RSV antibody, or antigen-binding fragment thereof.

4. The anti-RSV antibody formulation of claim 1, comprising about 150 mg/mL to about 200 mg/mL of the anti-RSV antibody, or antigen-binding fragment thereof.

5. The anti-RSV antibody formulation of claim 1, comprising about 175 mg/ml of the anti-RSV antibody, or antigen-binding fragment thereof.

6. The anti-RSV antibody formulation of claim 1, comprising about 175 mg/mL to about 225 mg/mL of the anti-RSV antibody, or antigen-binding fragment thereof.

7. The anti-RSV antibody formulation of claim 1, comprising about 200 mg/ml of the anti-RSV antibody, or antigen-binding fragment thereof.

8. The anti-RSV antibody formulation of claim 1, wherein the pH is 5.5 to 6.5.

9. The anti-RSV antibody formulation of claim 1, wherein the pH is 6.0.

10. The anti-RSV antibody formulation of claim 1, wherein the anti-RSV antibody comprises a heavy chain immunoglobulin consisting of the amino acid sequence set forth in SEQ ID NO: 9 and a light chain immunoglobulin consisting of the amino acid sequence set forth in SEQ ID NO: 10.

11. The anti-RSV antibody formulation of claim 1, comprising about 10-20 mM histidine.

12. The anti-RSV antibody formulation of claim 1, comprising about 10 mM histidine.

13. The anti-RSV antibody formulation of claim 1, comprising about 6.5% to about 7.5% (w/v) sucrose.

14. The anti-RSV antibody formulation of claim 1, comprising about 0.01% to about 0.04% (w/v) polysorbate 80.

15. The anti-RSV antibody formulation of claim 1, comprising about 0.02% w/v polysorbate 80.

16. An anti-RSV antibody formulation consisting of:
a) about 125 mg/mL to about 175 mg/mL of an anti-RSV antibody
wherein the anti-RSV antibody comprises a heavy chain variable region having the amino acid sequence of SEQ ID NO: 7 and a light chain variable region having the amino acid sequence of SEQ ID NO: 8;
b) about 10 mM histidine;
c) about 4% to about 8% (w/v) sucrose;
d) about 70 mM of L-arginine or a pharmaceutically acceptable salt of L-arginine; and
e) about 0.02% (w/v) polysorbate 80.

17. The anti-RSV antibody formulation of claim 16, wherein the formulation comprises about 150 mg/ml of the anti-RSV antibody.

*    *    *    *    *

SEQUENCE LISTING

<160> NUMBER OF SEQ ID NOS: 10

<210> SEQ ID NO 1
<211> LENGTH: 5
<212> TYPE: PRT
<213> ORGANISM: Homo sapiens

<400> SEQUENCE: 1

Asp Ser Ala Met Ser
1               5

<210> SEQ ID NO 2
<211> LENGTH: 19
<212> TYPE: PRT
<213> ORGANISM: Homo sapiens

<400> SEQUENCE: 2

Phe Ile Lys Ser Lys Thr Tyr Gly Gly Thr Lys Glu Tyr Ala Ala Ser
1               5                   10                  15

Val Lys Gly

<210> SEQ ID NO 3
<211> LENGTH: 16
<212> TYPE: PRT
<213> ORGANISM: Homo sapiens

<400> SEQUENCE: 3

Gly Ala Pro Tyr Gly Gly Asn Ser Asp Tyr Tyr Tyr Gly Leu Asp Val
1               5                   10                  15

<210> SEQ ID NO 4
<211> LENGTH: 11
<212> TYPE: PRT
<213> ORGANISM: Homo sapiens

<400> SEQUENCE: 4

```
Arg Thr Ser Gln Asp Val Arg Gly Ala Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Ser Leu Glu Thr
1               5

<210> SEQ ID NO 6
<211> LENGTH: 9
<212> TYPE: PRT
<213> ORGANISM: Homo sapiens

<400> SEQUENCE: 6

Gln Gln Phe Leu Asp Phe Pro Phe Thr
1               5

<210> SEQ ID NO 7
<211> LENGTH: 124
<212> TYPE: PRT
<213> ORGANISM: Artificial Sequence
<220> FEATURE:
<223> OTHER INFORMATION: RB-1 heavy chain with amino acid substitution

<400> SEQUENCE: 7

Glu Val Gln Leu Val Glu Ser Gly Gly Gly Leu Val Arg Pro Gly Arg
1               5                   10                  15

Ser Leu Arg Leu Ser Cys Thr Val Ser Gly Phe Ser Phe Asp Asp Ser
            20                  25                  30

Ala Met Ser Trp Val Arg Gln Ala Pro Gly Lys Gly Leu Glu Trp Ile
        35                  40                  45

Ser Phe Ile Lys Ser Lys Thr Tyr Gly Gly Thr Lys Glu Tyr Ala Ala
    50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Asp Tyr Tyr Tyr
            100                 105                 110

Gly Leu Asp Val Trp Gly Gln Gly Thr Thr Val Thr
        115                 120

<210> SEQ ID NO 8
<211> LENGTH: 106
<212> TYPE: PRT
<213> ORGANISM: Homo sapiens

<400> SEQUENCE: 8

Met Thr Gln Ser Pro Ser Ser Leu Ser Ala Ser Val Gly Asp Arg Val
1               5                   10                  15

Thr Ile Thr Cys Arg Thr Ser Gln Asp Val Arg Gly Ala Leu Ala Trp
            20                  25                  30

Tyr Gln Gln Lys Pro Gly Lys Ala Pro Lys Leu Leu Ile Phe Asp Ala
        35                  40                  45

Ser Ser Leu Glu Thr Gly Val Pro Ser Arg Phe Ser Gly Ser Gly Ser
    50                  55                  60
```

```
Gly Thr Val Phe Thr Leu Thr Ile Ser Ser Leu Gln Pro Glu Asp Phe
65                  70                  75                  80

Ala Ala Tyr Tyr Cys Gln Gln Phe Leu Asp Phe Pro Phe Thr Phe Gly
                85                  90                  95

Gln Gly Thr Arg Leu Glu Ile Lys Arg Thr
            100                 105

<210> SEQ ID NO 9
<211> LENGTH: 457
<212> TYPE: PRT
<213> ORGANISM: Artificial Sequence
<220> FEATURE:
<223> OTHER INFORMATION: RB1+YTE heavy chain

<400> SEQUENCE: 9

Glu Val Gln Leu Val Glu Ser Gly Gly Gly Leu Val Arg Pro Gly Arg
1               5                   10                  15

Ser Leu Arg Leu Ser Cys Thr Val Ser Gly Phe Ser Phe Asp Asp Ser
            20                  25                  30

Ala Met Ser Trp Val Arg Gln Ala Pro Gly Lys Gly Leu Glu Trp Ile
        35                  40                  45

Ser Phe Ile Lys Ser Lys Thr Tyr Gly Gly Thr Lys Glu Tyr Ala Ala
    50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Asp Tyr Tyr Tyr
            100                 105                 110

Gly Leu Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Tyr Ile Thr Arg Glu Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320
```

-continued

```
Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455
```

```
<210> SEQ ID NO 10
<211> LENGTH: 214
<212> TYPE: PRT
<213> ORGANISM: Artificial Sequence
<220> FEATURE:
<223> OTHER INFORMATION: RB1+YTE light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Val Arg Gly Ala
            20                  25                  30

Leu Ala Trp Tyr Gln Gln Lys Pro Gly Lys Ala Pro Lys Leu Leu Ile
            35                  40                  45

Phe Asp Ala Ser Ser Leu Glu Thr Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Ala Tyr Tyr Cys Gln Gln Phe Leu Asp Phe Pro Phe
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
        195                 200                 205

Phe Asn Arg Gly Glu Cys
    210
```